(12) United States Patent
Grupp

(10) Patent No.: US 12,251,344 B2
(45) Date of Patent: Mar. 18, 2025

(54) SYSTEMS AND METHODS FOR GENERATING AN AIR CURTAIN

(71) Applicant: LIFEAIR MEDICAL CORPORATION, Portland, OR (US)

(72) Inventor: Daniel Grupp, Portland, OR (US)

(73) Assignee: LifeAir Medical Corporation, Portland, OR (US)

( * ) Notice: Subject to any disclaimer, the term of this patent is extended or adjusted under 35 U.S.C. 154(b) by 0 days.

(21) Appl. No.: 18/629,349

(22) Filed: Apr. 8, 2024

(65) Prior Publication Data

US 2024/0335342 A1 Oct. 10, 2024

Related U.S. Application Data

(60) Provisional application No. 63/514,115, filed on Jul. 17, 2023, provisional application No. 63/458,347, (Continued)

(51) Int. Cl.
| | |
|---|---|
| *A61G 7/05* | (2006.01) |
| *A61L 9/20* | (2006.01) |
| *A61L 9/22* | (2006.01) |

(52) U.S. Cl.
CPC ............... *A61G 7/05* (2013.01); *A61L 9/205* (2013.01); *A61L 9/22* (2013.01); *A61L 2209/14* (2013.01)

(58) Field of Classification Search
CPC ........ A61L 9/205; A61L 9/22; A61L 2209/14; A61G 7/05
See application file for complete search history.

(56) References Cited

U.S. PATENT DOCUMENTS 3,820,536 A * 6/1974 Anspach, Jr. et al. .. F24F 3/163
128/853
4,063,495 A * 12/1977 Duvlis ................ A61G 13/108
454/191
(Continued)

FOREIGN PATENT DOCUMENTS

| CN | 210612385 U | 5/2020 |
|---|---|---|
| CN | 113262116 A | 8/2021 |
| JP | 2011247480 A | 12/2011 |

OTHER PUBLICATIONS

International Search Report re PCT/US2024/023607 dated Jun. 26, 2024 (2 pages).
(Continued)

*Primary Examiner* — George Sun
(74) *Attorney, Agent, or Firm* — Aurora Consulting LLC; Ashley Sloat; David Jackrel

(57) ABSTRACT

The present disclosure provides systems and methods for generating an air curtain. In some embodiments, a system includes an arch-shaped air outlet and an arch-shaped air inlet configured to generate an arch-shaped air curtain. The air outlet and inlet can also be configured to couple to regions of a bed, where at least a portion of one of the regions is between a head and a foot of the bed. One or more air outlet and inlet conduits can be coupled to the air outlet and inlet respectively. One or more devices that motivate air flow can be coupled to the air inlet and outlet conduits, wherein an air flow out of the air outlet is less than an air flow into the air inlet. A filter or pathogen deactivation unit configured to reduce pathogens can also be coupled to the air outlet conduit.

26 Claims, 33 Drawing Sheets

Related U.S. Application Data filed on Apr. 10, 2023, provisional application No. 63/458,159, filed on Apr. 9, 2023.

(56) References Cited

U.S. PATENT DOCUMENTS

| | | | | |
|---|---|---|---|---|
| 4,140,105 A | * | 2/1979 | Duvlis | A61G 13/108 |
| | | | | 454/191 |
| 4,422,369 A | * | 12/1983 | Smets | F24F 9/00 |
| | | | | 55/385.3 |
| 4,650,171 A | * | 3/1987 | Howorth | A61G 13/108 |
| | | | | 128/845 |
| 4,666,478 A | * | 5/1987 | Boissinot | B01D 39/00 |
| | | | | 55/470 |
| 4,742,764 A | * | 5/1988 | Duvlis | A61G 13/108 |
| | | | | 454/190 |
| 6,318,110 B1 | * | 11/2001 | Katayama | F25C 3/04 |
| | | | | 62/347 |
| 7,934,981 B2 | * | 5/2011 | Muggah | A61G 10/005 |
| | | | | 454/189 |
| 2005/0199736 A1 | * | 9/2005 | Matsushima | A47C 19/022 |
| | | | | 62/186 |
| 2006/0053554 A1 | * | 3/2006 | Acton | A61G 7/0524 |
| | | | | 5/600 |
| 2010/0005588 A1 | * | 1/2010 | Christopher | A47C 31/123 |
| | | | | 5/423 |
| 2024/0341493 A1 | * | 10/2024 | de Jong | F24F 5/0096 |

OTHER PUBLICATIONS

Written Opinion re PCT/US2024/023607 dated Jun. 26, 2024 (10 pages).

\* cited by examiner

| Condition | Ratio of Outlet:Inlet Flow Rate | Outlet Flow Rate (l/s) | Inlet Flow Rate (l/s) | Source Flow Rate (l/s) | Results: Percent of airflow collected |
|---|---|---|---|---|---|
| 1 | 1:1 | 100 | 100 | 40 | 50% |
| 2 | 1:2 | 100 | 200 | 40 | 75% |
| 3 | 1:2 | 100 | 200 | 8 | 90% |
| 4 | 1:6 | 50 | 300 | 8 | 99% |

SYSTEMS AND METHODS FOR GENERATING AN AIR CURTAIN

RELATED APPLICATIONS

This application claims the priority benefit of U.S. Provisional Patent Application No. 63/458,159, filed on Apr. 9, 2023; U.S. Provisional Patent Application No. 63/458,347, filed on Apr. 10, 2023; and U.S. Provisional Patent Application No. 63/514,115, filed on Jul. 17, 2023; the contents of each of which are hereby incorporated by reference in their entireties.

BACKGROUND

Patients in a hospital regularly become ill from illnesses they contract in the hospital. One of the major sources of these diseases is airborne pathogens. Many airborne pathogens originate with the exhalations of sick patients. Hospitals generally have filters in the air handling system of the building to remove such airborne pathogens. However, they can be inadequate. Pathogens spread in a local environment before air cleaners can gather them, and various mixing and flow patterns prevent a full cleaning of the air.

SUMMARY

The present disclosure provides systems and methods for generating an air curtain.

In some embodiments, the techniques described herein relate to a system including: an arch-shaped air outlet configured to couple to a first region of a bed and to provide air to generate an arch-shaped air curtain, the arch-shaped air outlet including an air outlet port arranged along the arch-shaped air outlet, wherein the arch-shaped air outlet is configured to allow access to a space between the arch-shaped air curtain and the bed through an inside of the arch-shaped air outlet; an arch-shaped air inlet configured to couple to a second region of a bed and capture air from the arch-shaped air curtain and from outside of the arch-shaped air curtain, the arch-shaped air inlet including an air inlet port arranged along the arch-shaped air inlet, wherein the arch-shaped air inlet is configured to allow access to a space between the arch-shaped air curtain and the bed through the inside of the arch-shaped air inlet; one or more air outlet conduits coupled to the arch-shaped air outlet; one or more air inlet conduits coupled to the arch-shaped air inlet; one or more devices that motivate air flow, coupled to the air inlet conduit and the air outlet conduit; and a filter or pathogen deactivation unit coupled to the air outlet conduit configured to reduce pathogens in the air flowing through the air outlet conduit; wherein an air flow out of the arch-shaped air outlet is less than an air flow into the arch-shaped air inlet; wherein at least a portion of the first region of the bed or at least a portion of the second region of the bed is between a head of the bed and a foot of the bed, wherein the bed includes four sides including the head, the foot, a first side extending from the head to the foot, and a second side, opposite the first side, extending from the head to the foot.

In some embodiments, the techniques described herein relate to a system including: an arch-shaped air outlet configured to provide air for an arch-shaped air curtain, the arch-shaped air outlet including: an air outlet port arranged along the arch-shaped air outlet; and a movable material arranged across the arch-shaped air outlet, wherein the movable material is configured to be movable and to allow access to a space within the arch-shaped air curtain when moved; at least one air outlet conduit coupled to the arch-shaped air outlet; and at least one device that motivates air flow coupled to the air outlet conduit; wherein the arch-shaped air outlet is configured to couple to a first region of a bed, and wherein the arch-shaped air curtain is configured to be aimed downwards towards the bed, such that the arch-shaped air curtain blocks particles from an environment from reaching a head of a patient on the bed.

In some embodiments, the techniques described herein relate to a method for generating an arch-shaped air curtain including: providing an arch-shaped air outlet configured to couple to a first region of a bed and to provide air to generate an arch-shaped air curtain, the arch-shaped air outlet including an air outlet port arranged along the arch-shaped air outlet, wherein the arch-shaped air outlet is configured to allow access to a space between the arch-shaped air curtain and the bed through an inside of the arch-shaped air outlet; providing an arch-shaped air inlet configured to couple to a second region of a bed and capture air from the arch-shaped air curtain and from outside of the arch-shaped air curtain, the arch-shaped air inlet including an air inlet port arranged along the arch-shaped air inlet, wherein the arch-shaped air inlet is configured to allow access to a space between the arch-shaped air curtain and the bed through the inside of the arch-shaped air inlet; providing one or more air outlet conduits coupled to the arch-shaped air outlet; providing one or more air inlet conduits coupled to the arch-shaped air inlet; motivating air flow using one or more devices coupled to the air inlet conduit and the air outlet conduit such that an air flow out of the arch-shaped air outlet is less than an air flow in to the arch-shaped air inlet; and filtering the air using a filter, or deactivating pathogens using a pathogen deactivation unit, wherein the filter or the pathogen deactivation unit is coupled to the air outlet conduit, wherein at least a portion of the first region of the bed or at least a portion of the second region of the bed is between a head of the bed and a foot of the bed, wherein the bed includes four sides including the head, the foot, a first side extending from the head to the foot, and a second side, opposite the first side, extending from the head to the foot.

DETAILED DESCRIPTION

Figure 1A:
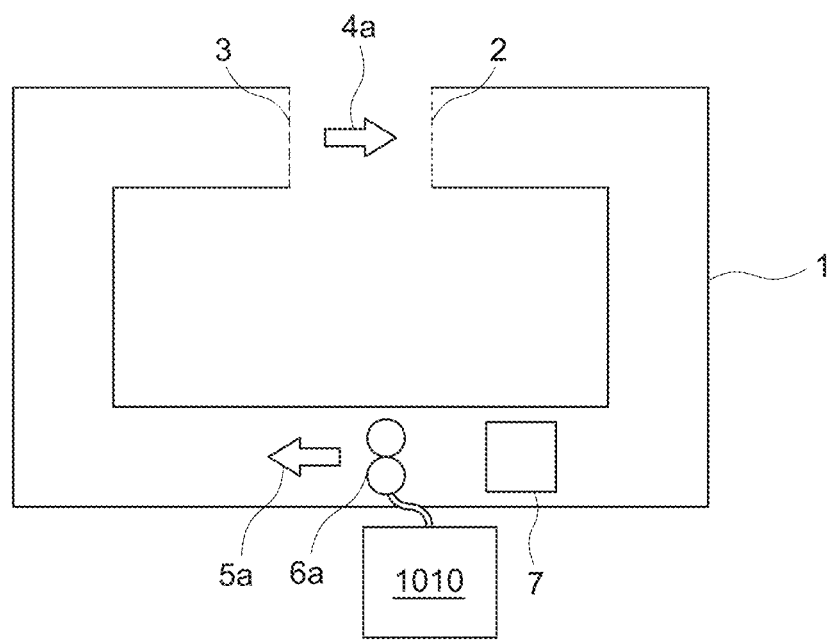
FIGS. 1A and 1B show example schematics of systems that can provide an air curtain, in accordance with some embodiments.

The present disclosure provides techniques for an air curtain for a person or a patient. In some embodiments, systems and methods for providing an air curtain for a person or a patient include an air outlet to provide air for the air curtain. An air curtain is a generally considered to be a layer of moving air. In some embodiments, the systems and methods also include air inlet to intake air from the air curtain. For example, the systems and methods described herein can be used to provide an air curtain in the proximity of a person or a patient such that an amount of unwanted species (e.g., bacteria, viruses, fungi, etc.) from the person within the air curtain can be contained by the air curtain thereby protecting other people in the environment. The systems and methods described herein can also be used to reduce the amount of unwanted species from the environment reaching the person inside of the air curtain.

The air inlet and air outlet can be coupled to one or more devices that motivate air flow, in order to output and intake the air. In some cases, the air inlet intakes more air than the air outlet, for example, such that substantially all of the air from the air curtain is captured by the air inlet, and some additional air outside of the air curtain is also captured by the air inlet. A "device that motivates air flow" is considered herein to refer to any device that motivates air to flow, such as one or more fans, blowers, roots blowers, scroll pumps, side-channel blowers (single and two-stage), regenerative blowers (also known as vortex blowers), pumps, rotary vane pumps, diaphragm pumps, piston pumps, turbomolecular pumps, disc pumps, and/or peristaltic pumps.

The air outlet and air inlet of the systems described herein include a respective air outlet port and an air inlet port, through which the air flows to form the air curtain. The air outlet port and air inlet port can include one or more holes through which the air flows. The air outlet port and air inlet port can each include holes with many different shapes and be arranged in many different patterns and have three-dimensional structures such as conduits, tubes, pipes, and arrays thereof, for directing air. For example, the holes could be shaped as one or more slots, round holes, holes with a geometric shape (e.g., square, rectangular, hexagonal, etc.), holes with a grating, or a honeycomb pattern of holes (e.g., of round holes, hexagonal holes, etc.). In some cases, the air outlet is formed in the shape of an arch. For example, the air outlet port can be formed in a line along the arch-shaped air outlet, or can be along a periphery of the arch-shaped air outlet. For example, the port can include a plurality of holes (e.g., round holes, oblong holes, or slots) that are arranged along the arch. A material can be arranged across the arch-shaped air outlet. In some cases, the material can be a non-rigid material configured to be movable and to allow access to a space within the arch-shaped air curtain when moved. In some cases, the material can be a rigid material configured to be movable and to allow access to a space within the arch-shaped air curtain when moved, for example using one or more hinges. In some cases, the material can be a mixture of rigid and non-rigid materials in different areas of the arch and be configured to be movable and to allow access to a space within the arch-shaped air curtain when moved.

In some cases, the air outlet and/or air inlet is formed in the shape of an arch. The arch-shaped air outlet can be configured to couple to a first region of a bed and to provide air to generate an arch-shaped air curtain. The arch-shaped air inlet can be configured to couple to a second region of a bed and intake air from the arch-shaped air curtain. The systems and methods described herein can be used with a flat bed, or a bed that is adjustable (e.g., that can change positions from sitting, to reclining, to lying down).

In some cases, the arch-shaped air inlet can also be configured to intake air from outside of the arch-shaped air curtain, for example, if more air is captured by the arch-shaped air inlet than is output by the arch-shaped air outlet. The arch-shaped air outlet can include an outlet port arranged along the arch-shaped air outlet, and the arch-shaped air inlet can include an air inlet port arranged along the arch-shaped air inlet. For example, the air inlet port can be arranged (or formed in a line) along the arch-shaped air inlet, or can be along a periphery of the arch-shaped air inlet. For example, the air inlet port can be arranged (or formed in a line) along the arch-shaped air inlet, or can be along a periphery of the arch-shaped air inlet.

In some cases, the air inlet and/or arch-shaped air outlet has an open space across the inside of the arch, which can allow access into an isolated space between the air curtain and a surface. For example, a caregiver can reach through the inside of the arch to interact with a person inside the isolated space between the air curtain and a surface (e.g., a bed). In another example, an arch can be arranged across a bed, and a person can lie underneath the arch, with their body or legs extending through the inside of the arch.

In some cases, a material can be arranged across the air inlet and/or arch-shaped air outlet. In some cases, the material can be a non-rigid material configured to be movable and to allow access to a space within the arch-shaped air curtain when moved. In some cases, the material can be a rigid material configured to be movable and to allow access to a space within the (arch-shaped) air curtain when moved, for example using one or more hinges. In some cases, the material can be a mixture of rigid and non-rigid materials in different areas of the arch and be configured to be movable and to allow access to a space within the arch-shaped air curtain when moved.

The systems for generating air curtains described herein can include a combination of features that can be particularly advantageous. For example, an inlet and/or outlet can be shaped like an arch, with access possible through the inside of the arch. Those features can enable the outlet and inlet to be positioned closer to one another. For example, the access through the inside of the arch can enable the inlet or outlet to be placed between the head and foot of a bed with a person lying on the bed with their body extending through the inside of the arch. It is advantageous to have the outlet and inlet of an air curtain closer together since it will improve the isolation efficiency of the air curtain, where the isolation efficiency is a measure of how well the air curtain can isolate particulates within a region, or isolate a region from particulates. In another example, the outlet and inlet arches can be placed on either side of a bed, and a caregiver can reach through the arch to a person that is between the air curtain and the bed. The access provided by the systems and methods described herein can advantageously block particles from exiting or entering a space defined by the air curtain and improve the comfort of the person and accessibility to the person by providing access into and out of the space. Another feature that can be combined with the above is a flow imbalance where an air flow out of the arch-shaped air outlet is less than an air flow into the arch-shaped air inlet, which can further improve the isolation efficiency especially when combined with other features that allow the arches to be placed close to one another (e.g., on inlet/outlet on opposite sides of a bed, or inlet at the head of a bed and outlet between the head and foot of the bed).

In some cases, the systems and methods for generating an air curtain described herein can isolate particles or prevent particles from leaving a region between the air curtain and a surface with an efficiency from about 50% to about 90%, or from about 50% to about 99%, or from about 50% to about 99.9%, or greater than about 60%, or greater than about 80%, or greater than about 90%. In some cases, the systems and methods for generating an air curtain described herein can isolate particles or prevent particles from entering a region between the air curtain and a surface with an efficiency from about 50% to about 90%, or from about 50% to about 99%, or from about 50% to about 99.9%, or greater than about 60%, or greater than about 80%, or greater than about 90%.

The systems and methods for generating an air curtain described herein can isolate particles as well as other vapors such as odors or smoke. For example, the system may be used to isolate smoke generated during surgical procedures such as electrocautery. In another example, the system may be used to isolate and contain odors from kitty litter boxes. In another example, the system may be used to contain smoke from industrial processes, such as welding. In some cases, the system may be used to isolate and protect food from becoming contaminated with pathogens in the environment, such as for use in a salad bar or food buffet, or in food preparation, such as a kitchen in a restaurant or industrial kitchen, bakery, or food processing facility. In another example, the system may be used in biotechnology applications or biological processing, such as pharmaceutical processing, genetic engineering, or in-vitro fertilization. In another example, the system may be used in place of a fume hood, or the system may be used inside a fume hood.

An air inlet conduit or duct can be coupled to the arch-shaped air inlet, and an air outlet conduit or duct coupled to the arch-shaped air outlet. For example, a conduit can be a pipe or cylinder with a circular or oval cross-section. A conduit can also be a tube or duct with a square, rectangular, hexagonal, or other shaped cross-section. The terms conduits, ducts, and tubes may be used interchangeably. The outlets and inlets, such as the arch-shaped outlets and inlets, described herein can also be hollow and elongate structures (i.e., with relatively high aspect ratios) that could be considered conduits. The outlets and inlets may also have conduits, tubes, pipes, or ducts within them. For example, the outlets and inlets can have tubes, pipes, or ducts within them that couple the port(s) of the outlet or inlet to the air outlet or air inlet conduits or ducts (which in turn are coupled to the device(s) that motive air flow).

One or more devices that motivate air flow (e.g., fans or pumps) can be coupled to the air outlet conduit or duct and the air inlet conduit or duct. The devices that motivate air flow can be controlled using a controller (e.g., with a hardware processor coupled to memory) such that an amount of air exiting the arch-shaped air outlet and an amount of air entering the arch-shaped air inlet can be controlled, either together or independently. For example, the amount of air exiting the arch-shaped air outlet can be controlled to be less than an amount of air entering the arch-shaped air inlet. In such cases, the arch-shaped air inlet can capture air from the air curtain and also from outside the air curtain. In some cases, a ratio of air flow into the air inlet to air flow out of the air outlet can be from about 1.5 to about 10, or from about 2 to about 6, or about 1.5, or about 2, or about 3, or about 4, or about 6, or about 10. In some cases, ratio of air flow into the air inlet to air flow out of the air outlet can be more than about 10, for example, when the efficiency of collection is required to be as high as possible.

The systems and methods described herein can include hardware processors coupled to memory, in some cases. Some examples of hardware processors can include central processing units (CPUs), graphics processing units (GPUs), application-specific integrated circuits (ASICs), or field-programmable gate arrays (FPGAs). These hardware processors may be interconnected through various means, including buses, networks-on-chip (NoCs), or other suitable communication channels. The memory coupled to these processors may include various types, such as volatile memory (e.g., dynamic random-access memory (DRAM), static random-access memory (SRAM)) and non-volatile memory (e.g., flash memory, phase-change memory, magnetic storage). The choice of hardware processors and memory configurations may vary depending on the system or method.

Computer simulations were performed using Computational Fluid Dynamics (CFD), and generally demonstrated that increasing levels of air-curtain isolation efficiency could be achieved by increasing the ratio of inlet to outlet flow (more air is drawn out of the air curtain by the inlet than is introduced to the air curtain by the outlet).

The efficiency of a prototype system containing an arch-shaped outlet and an arch-shaped inlet was also experimentally measured. A TSI Portacount Model 8020A particle detector was used with a Portacount Salt Particle Generator Model 8026. Two experiments were performed. In the first experiment, the particle generator was located inside a protected region formed between the arch-shaped outlet and inlet and a bed to which they were coupled, and the particle detector sampled measurements outside the protected region. In the first experiment, the system and air curtain was about 90% efficient; the amount of particulates measured was about 90% less outside of the protected region compared to the amount of particulates inside the protected region. In a second experiment, the particle detector was located outside the protected region, and the particle detector sampled measurements from inside the protected region. In the second experiment, the system and air curtain was also about 90% efficient; the amount of particulates measured was about 90% less inside of the protected region compared to the amount of particulates outside of the protected region (near the particle generator).

In some cases, one or more devices that motivate air flow (e.g., fans or pumps) can be coupled directly to the air outlet and/or air inlet instead of, or in addition to, the device(s) that motivate air flow being in the conduits. The device that motivates air flow in the air outlet and/or air inlet can be used to efficiently produce the air flow for the air curtain, and the air flow to capture air from the air curtain.

A filter and/or a pathogen deactivation unit can be coupled to the air inlet conduit or duct. The pathogen deactivation unit can include subsystems that deactivate pathogens such as UV lights, or a plasma generator. Filters can be used together with a pathogen deactivation device, in the systems and methods descried herein. For example, the filter can be configured to reduce unwanted species (e.g., dust, pathogens, odors, or chemicals) in the air traveling through the air inlet conduit or duct. Filters may be mechanical filters and/or electrostatic filters. In some applications it may be desirable to isolate a patient from particulates other than pathogens in the environment. In these cases, a filter that removes matter from the air is preferable to subsystems that deactivate pathogens but do not remove them from the air. The system may have a series of filters that are generally the same or different. Multiple filters that are the same when used in series may increase the filtration level of the system. In other embodiments, a series of filters may be used where each filter type removes a different type of material from the air, such as volatile organics for one type of filter, and viral particles for another type of filter.

A pathogen deactivation unit can be coupled to the air flow subsystem conduits to reduce infectious species in addition to, or instead of, the filters. For example, the pathogen deactivation unit can include plasma generators, ultraviolet lights (UV), photocatalysts (e.g., titanium dioxide or diatoms when used with UV light), or visible light (e.g., 405 nm light). For example, a pathogen deactivation unit can include a plasma generator, which generates a plasma in a region, and air can be forced to pass through the plasma (e.g., using a fan). UV light may for example have wavelengths in the range of about 220 nm to about 230 nm which has been shown to be harmless to humans, or about 255 nm to about 275 nm. These subsystems may not remove the particles (e.g., pathogens such as bacteria and viruses) but may be configured to inactivate the ability of a particle or pathogen to infect a person. Air that enters the pathogen deactivation unit with active (live or infectious) pathogens is configured to exit the pathogen deactivation unit with a reduced number of active pathogens. Such a reduction may be in the range of 2, 5 or 10, or 100, 1000, or 10,000 or greater.

In some cases, more than one conduit or duct can be coupled to an air inlet or an air outlet. For example, multiple conduits, each coupled to one or more devices that motivate air flow (e.g., fan, pump, or plurality of fans), can be coupled to an air outlet or an air inlet.

The systems described herein can be configured to be coupled to a bed, and provide an air curtain in the proximity of the bed. In some cases, the bed can be approximately rectangular, where the four sides can include a head, a foot, a first side extending from the head to the foot, and a second side, opposite the first side, extending from the head to the foot. In some cases, the arch-shaped air outlet of the systems described herein can be configured to be coupled to a first region of the bed, and the arch-shaped air outlet of the systems described herein can be configured to be coupled to a second region of the bed. In some cases, at least a portion of the first region of the bed or at least a portion of the second region of the bed is between a head of the bed and a foot of the bed. For example, the arch-shaped air outlet can be coupled to a first region of the bed near the head, and the arch-shaped air inlet can be coupled to a second region of the bed that is approximately halfway between the head and the foot of the bed. In some cases, the closer the spacing of the first and second regions generally the higher the protection efficiency of the air curtain is, where the protection efficiency is the ratio of particles impinging upon the air curtain to particles that pass through the air curtain.

In some cases, an air outlet can be used to provide an air curtain, and no air inlet is needed. For example, an air outlet can be used to provide an air curtain in the proximity of a bed such that an amount of unwanted species from the environment can be reduced for a person on the bed and inside of the air curtain. Such systems could be beneficial for example, to protect an immunocompromised person from unwanted pathogens in the environment.

In some cases, the systems and methods described herein include air inlet ports and/or air outlet ports including subsystems to direct the air exiting the outlet ports and/or entering the inlet ports. For example, the air could be directed upwards, downwards, left, or right relative to a nominal direction, for example, to align the air flow out of the outlet with air flow into the inlet. The subsystems to direct the air can include louvers, vents, movable tubes, air foils, flaps, or any structures inside the port (or a conduit leading to a port) or outside the port that can be used to direct the air flowing into or out of the port. For example, an air outlet port and/or air inlet port can include louvers that direct the air to generate the arch-shaped air curtain. In another example, an air outlet port and/or air inlet port can include a set of movable tubes that direct the air to generate the arch-shaped air curtain. The movable tubes can have circular or oval cross-sections, or can have square, rectangular, hexagonal, or other shaped cross-sections. In some cases, the movable tubes can be arranged in an array. For example, an array of tubes with hexagonal cross-sections can form a honeycomb structure, which can be moved to direct air flow out of the port of an outlet or into the port of an inlet. The subsystems to direct the air can be manually adjustable, or can be controlled using automated means (e.g., motors, actuators, controllers, sensors, and communication systems) to move the elements of the subsystems that are used to direct the air flow into or out of a port. In some cases, the manual adjustment or automated control of the subsystems to direct the air can cause the subsystems to direct the air to turn on or off. In some cases, the manual adjustment or automated control of the subsystems to direct the air can cause the subsystems to direct the air to change or adjust the speed or volume of air flow(s) in the system. The system may be configured to react to sensor outputs to adjust the ports in order to automatically optimize the air curtain (e.g., maximize efficiency) based on predetermined algorithms and settings.

In some cases, the components of the systems described herein, such as the air outlets, the air inlets, the conduits, the devices that motivate air flow, and a control system, are cleanable. In some cases, the components have removable access panels to allow cleaning. In some cases, a conduit may come apart in one or more sections where the interface is along the length of a conduit, such as a tube that splits in half along its length. In some cases, the components can be easily removed so that they can be cleaned, for example, by coupling them together using connectors such as snaps, magnets, or other fasteners. In some cases, conduits may be configured to couple to a cleaning system that introduces a cleaning gas such as ethylene oxide, steam, or hydrogen peroxide. For example, a subsystem that has a fan with inlet and an outlet ports may be coupled to a gas cleaning system to sterilize the surfaces of the fan in contact with air that flows through the system. In some cases, the components can be self-cleaning, for example, the conduits can contain ultraviolet (UV) lights that neutralize pathogens. In some cases, the components such as the ducts, the air outlet, and the air inlet can have antimicrobial coatings (e.g., silver or silver alloys, copper or copper alloys, or organosilanes) to prevent or inhibit the growth of microorganisms.

In some cases, the air outlets, the air inlets, and the conduits of the systems and methods described herein are disposable. For example, a system can include some disposable components and some non-disposable components. For example, a base can be non-disposable and include devices that motivate air flow (e.g., fans and pumps) and other components needed to control the system such as a processor or controller and human interface, and disposable conduits, a disposable air outlet, and a disposable air inlet can be coupled to the non-disposable base.

The control system may have settable configurations, that may be set by a user. For example, the flow rate in the air curtain may be increased or decreased, depending on desired isolation efficiency, power usage, or patient comfort, where lower flow may be, for example, quieter.

The subsystems of the patient isolation system may have structures and subsystems to minimize the sound that the system emits. A fan-containing subsystem may have an enclosure that contains sound, for example, by having walls composed of sound-damping materials, or multi-layered structures wherein the layers may alternate between rigid and pliable materials so as to form a sound-transmission impedance mismatch. The rigid layers in a multi-layered structure may be of the same or different materials, where different materials may favorably increase the impedance mismatch. Conduits may have foam on their inner surfaces which may be configured to act as a sound absorber, known in the art as a silencer. Flexible conduits may also have multi-layered structures that form the walls of the conduit, as well as structures that form flexible silencers, such as foam linings.

The systems and methods described herein can contain exhaled pathogens from infected patients. Additionally, the systems and methods described herein can block particles from entering or leaving a volume created by the systems around a living being, such as a human or an animal. The term exhale can refer to any air or particles leaving a mouth or nose of a person, and may include sneezes or coughs or other respiratory functions. The particles in the air can include pathogens, molds, fungi, microorganisms, dust, or any solid or liquid particles in the air. Pathogens as used herein are considered to be anything that causes an infection, condition, or disease in a patient, including but not limited to bacteria, fungi, molds, and viruses. Where operation of the system is described herein to stop transmission of pathogens, generally particles and pathogens may be used interchangeably, even though particles captured by the system may not be infectious. In some embodiments, the systems and methods described herein minimally interfere with patient comfort or safety, and give ready access to caregivers compared to conventional particle isolation systems that enclose the patient in a solid bubble of material (e.g., plastic). The systems and methods described herein use curtains of air through which people can access an isolated space between the air curtain and a surface (e.g., a bed). In some cases, the outlets and inlets can also be arch-shaped and allow access to the space through the arch. Improved access and a lack of a solid barrier around the person can improve their comfort, while maintaining their safety, and the safety of others around them (if they are contagious or have a communicable disease), by isolating the space of the person from the outside environment.

The systems and methods described herein use an air curtain in front of, or on a ventral side of, a patient. The various embodiments utilize a system where air is injected at a source (an outlet), and extracted at a sink (an inlet) where there is a distance through space between the source and sink. The inlet and outlet are connected in a generally closed loop where the air that goes into the inlet is drawn through a devices that motivate air flow (e.g., fan or pump) and fed to the outlet. The two systems may also be separate, where each inlet and outlet have one or more devices that motivate air flow, and filtration and/or pathogen-reducing subsystems.

Figure 1B:
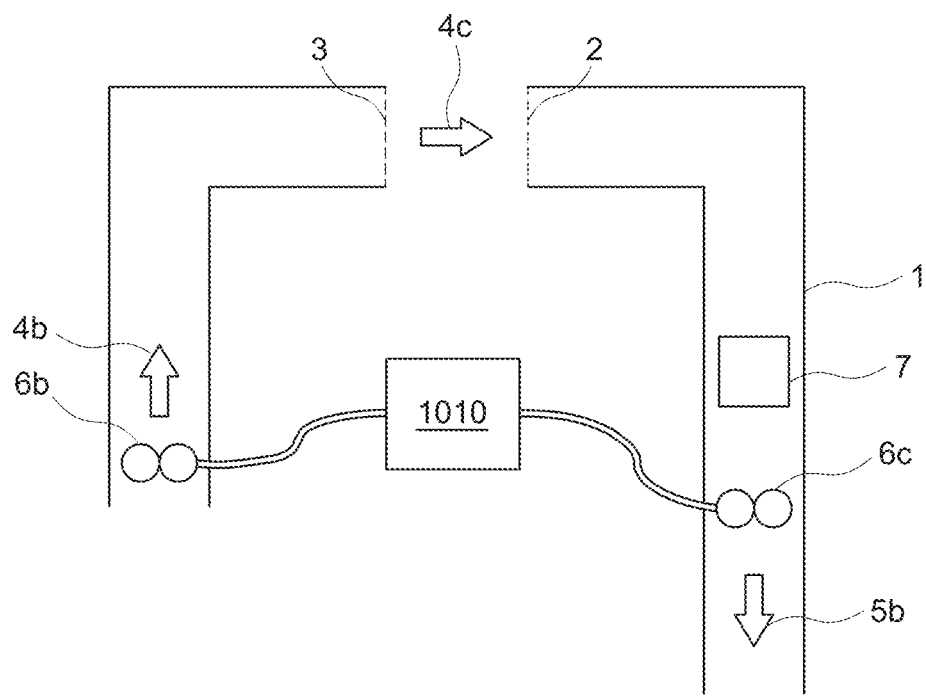

FIGS. 1A and 1B show example schematics of systems that can provide an air curtain, in accordance with some embodiments. In FIG. 1A, a conduit 1 has an inlet 2 and an outlet 3 where the inlet 2 and outlet 3 are in fluid communication. The air flows in a direction 4a and 5a motivated by a device that motivates air flow 6a (e.g., one or more fans or pumps). The air is motivated by device that motivates air flow 6a to move through the conduit 1 from the device that motivates air flow 6a towards the outlet 3, causing the air curtain 4a to be formed between the outlet 3 and the inlet 2. In FIG. 1A, device that motivates air flow 6a is optionally controlled by controller 1010, which can control the speed of the device that motivates air flow 6a based on user input or feedback from one or more sensors. The system in FIG. 1A includes an air recycling loop, wherein the air that enters the inlet 2 is directed back to the outlet 3. In FIG. 1B, there are two device that motivates air flows 6b and 6c, which motivate air in directions 4b and 5b, respectively. Device that motivates air flow 6b motivates the air to move through the conduit 1 from the device that motivates air flow 6b towards the outlet 3, causing the air curtain 4a to be formed between the outlet 3 and the inlet 2. Device that motivates air flow 6c causes air to move through the conduit 1 causing pressure in the inlet 2 to be reduced and air to be captured by the inlet 2. Devices that motivate air flow 6b and 6c are optionally controlled by controller 1010, which can control the speed of the devices that motivate air flow based on user input or feedback from one or more sensors. Controller 1010 can control the speed of devices that motivate air flow 6b and 6c such that a ratio of air flow in directions 4b and 5b is controlled. For example, controller 1010 can control the speed of devices that motivate air flow 6b and 6c such that a ratio of an air flow into inlet 2 to an air flow out of outlet 3 is from about 1.5 to about 10, or from about 2 to about 6, or about 1.5, or about 2, or about 3, or about 4, or about 6, or about 10. In some cases, controller 1010 controls the speed of devices that motivate air flow 6b and 6c based on user input, sensed air flow (using information from flow sensors in one or more of the conduits 1). In some cases, the inlets and outlets may be interchangeable, where and inlet may be used as an outlet, and an outlet may be used as an inlet, where the air-motivator subsystem may be configured to change direction of air flow.

The systems in FIGS. 1A and 1B each also include a pathogen deactivation unit 7 in series with the inlet 2 that cleans the air that flows into the inlet 2. Pathogen deactivation is the process of reducing the ability of a pathogen (e.g., a bacteria, a virus, a mold, or a fungus) to cause undesired health conditions. Pathogens can cause infectiousness, such as causing infections in or on a living creature, and the pathogen deactivation unit 7 can eliminate or reduce the infectiousness of a pathogen in or passing through the pathogen deactivation unit 7. Pathogen deactivation unit 7 can include a combination of filters and/or subsystems (e.g., plasma, UV light) that deactivate pathogens, as described herein. In some cases, the pathogen deactivation unit 7 or air cleaning subsystem cleans the air to a level of non-infectiousness in a pass or one or more passes, such as by 80%, 90%, 95%, 99%, 99.9%, 99.97%, or higher, pathogen reduction in a single pass. In some cases, the pathogen deactivation unit may sterilize the air. The pathogen deactivation unit 7 may not necessarily physically filter out the pathogens, but may kill or otherwise neutralize or deactivate pathogens while leaving dead pathogens in the air stream. For example, pathogen deactivation unit 7 or air cleaning subsystem could use UV lights, which would kill pathogens but not physically remove them from the air stream. In other cases, pathogen deactivation unit 7 or air cleaning subsystem can include filters and other subsystems to physically remove pathogens from the air stream.

In some cases, substantially all of the sourced air, leaving air outlet 3, is collected at air inlet 2. In some cases, the air flow out of air outlet 3 is less than the flow into air inlet 2. Such systems can be advantageous to create a cross-flow in front of a patient's mouth that pushes their exhaled air towards the air inlet 2. Such systems can also be advantageous to avoid blowing exhaled air from a patient into the environment, and not into the air inlet 2, where it can be cleaned by a pathogen deactivation unit 7.

Figure 2:
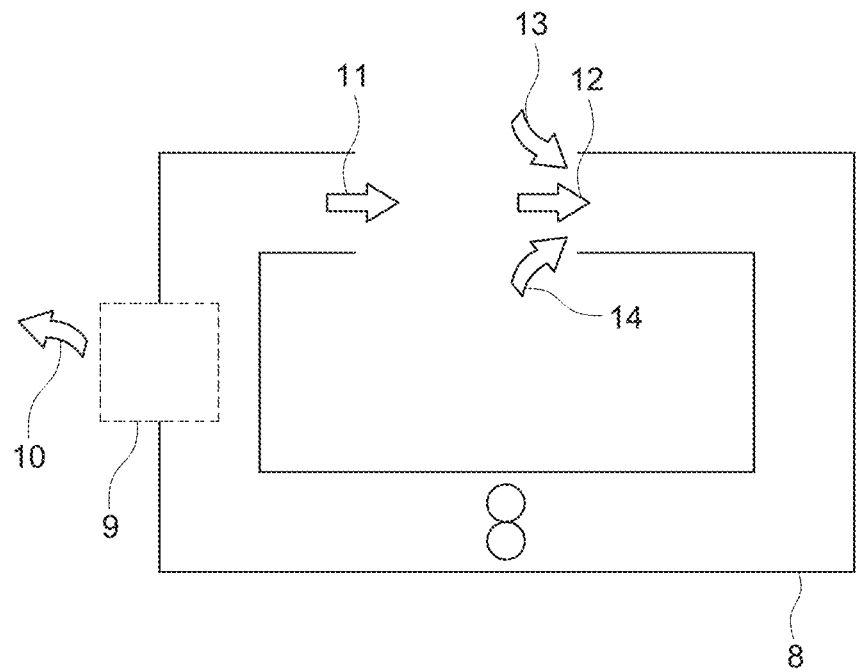
FIG. 2 shows an example schematic of a system similar to the system shown in FIG. 1A with a subsystem added to divert some of the airflow away from the outlet, in accordance with some embodiments.
Figure 3:
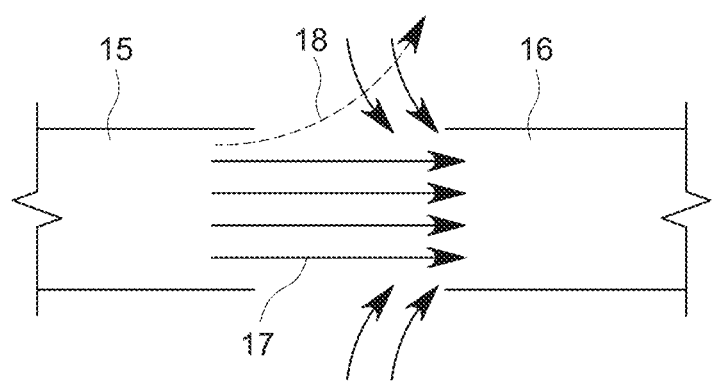
FIG. 3 shows an air curtain formed between an outlet and an inlet.

FIG. 2 shows an example schematic of a system similar to the system shown in FIG. 1A with a subsystem 9 added to divert some of the airflow away from the air outlet, in accordance with some embodiments. In this example, the air is recirculated from the air inlet to the air outlet, and there is a subsystem that diverts air such that the air flow out of air outlet 3 is less than the flow into air inlet 2. This subsystem 9 may be a valve, flap, orifice, or other subsystem for opening and letting air out of the main flow path of conduit 8. The subsystem 9 may also be an active electromechanical system that draws air out of the main flow path, such as a fan. In this manner, the airflow 11 at the air outlet may be made to be less than the airflow 12 at the air inlet, where the extra air is made up from the room with flow 13 and 14. In FIG. 3, an air curtain 17 is formed between air outlet 15 and air inlet 16. The airflow 18 (dashed line) that leaves the air outlet 15, and is not captured by the air inlet 16, can be minimized or eliminated. Thus, pathogens entering the stream 17 will be carried into the air inlet 16. An advantage of the air cleaning system for isolating patients is that it also cleans the air in the room and can be used an room-air purifier.

Figures 4A, 4B:
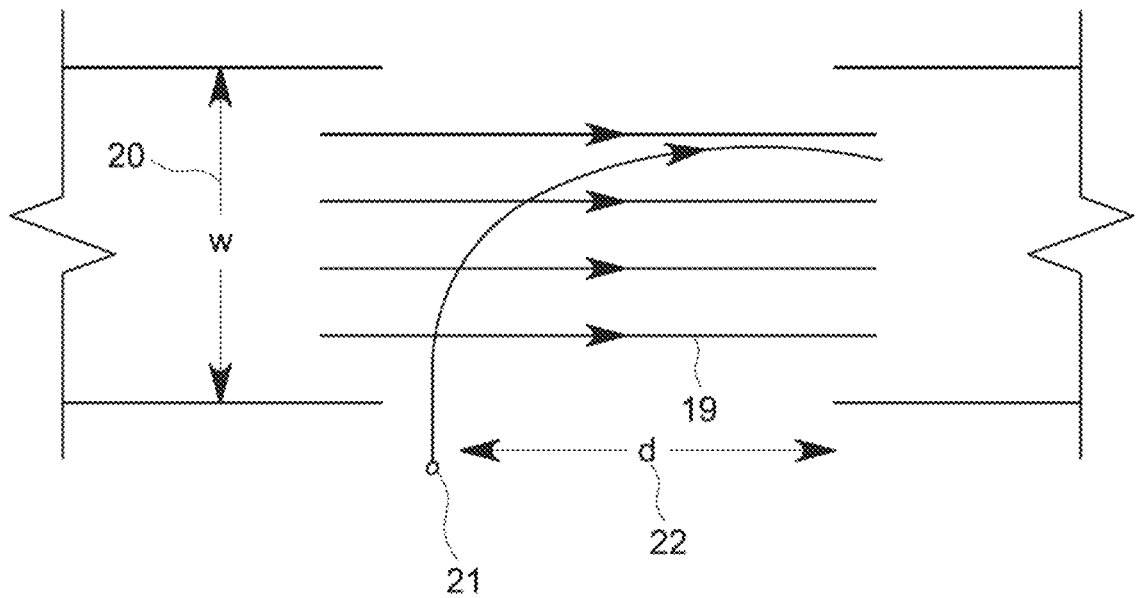
FIG. 4A shows an example schematic of an air curtain, between an outlet and an inlet, in accordance with some embodiments.
FIGS. 4B-4F show results of computational fluid dynamics (CFD) modeling that was performed for a system with an outlet and an inlet forming an air curtain, and a source within a protected region, in accordance with some embodiments.

FIG. 4A shows an example schematic of an air curtain 19, between an air outlet and an air inlet, in accordance with some embodiments. Air curtain 19 (or region of flowing air) has a sufficient thickness 20 that fast-moving matter 21 (i.e., droplets) entering the airstream have time to be diverted towards the inlet. In some cases, the thickness 20 of the air curtain is from about 2 cm to about 50 cm, or from about 2 cm to about 20 cm, or from about 20 cm to about 30 cm, or from about 30 cm to about 50 cm. The thickness 20 of the air curtain may be less than, equal to, or greater than the length 22 of the air curtain, where thicker air curtains for the same speed of moving air (higher overall flow) have generally higher protection efficiency. In some cases, the thickness 20 is about 10 times smaller than a length 22 of the air curtain. Droplets 21 may enter at a speed higher than the airflow speed, and may still get collected due to the rapid deceleration of airstreams and particles moving in air. For example, not to be limited by theory, the deceleration of particles in moving air can be described by a relationship where speed is proportional to a power of time, wherein the power can be from 2 to 4 (i.e., speed is approximately time$^{\wedge}$n, where n=2, 3, or 4).

For example, it has been found that for air flowing at a speed of approximately 3 m/s, and small droplets (~20 μm diameter) entering at about 5 m/s to 10 m/s will be drawn into the air inlet if the width is at least about 25 cm and the distance 22 from the injection of the particles into the airstream to the air inlet is about 50 cm. Other geometries are possible, since the width w and the length d depend on factors such as the speed of the air curtain 19.

The air flows in the conduits, inlets, outlets and air curtains of the systems described herein can operate in different flow regimes. For example, air flows in the air curtains, or in the conduits, or exiting the outlets, or entering the inlets of the systems described herein can have velocities from 0.05 m/s to 10 m/s, or from 0.5 m/s to 5 m/s, or from 0.5 m/s to 2 m/s, or about 0.1 m/s, or about 1 m/s, or about 5 m/s, and have volumetric flow rates from 5 to 5000 cc/s per square centimeter, or about 10 cc/s per square centimeter, or about 100 cc/s per square centimeter, or about 500 cc/s per square centimeter The overall flow rate through conduits, inlets, and/or outlets of the system can be from about 10 CFM (cubic feet per minute) to about 100 CFM (or about 17 to about 170 m$^3$/h), about 100 CFM to about 500 CFM (about 170 to about 850 m$^3$/h), or most preferably about 500 CFM to about 1000 CFM (about 850 to about 1700 m$^3$/h), or about 1000 CFM to about 5000 CFM (about 1700 to about 8500 m$^3$/h), with corresponding air curtain flow rates depending on port configurations and arch length.

Computer simulations were performed using computational fluid dynamics (CFD) to investigate different flow rates out of outlets and into inlets to form air curtains. The models were used to determine system or air-curtain isolation efficiencies to prevent an introduced source gas (e.g., containing particulates) from leaving a protected region or zone. These models showed that increasing levels of air-curtain isolation efficiency could be achieved by increasing the ratio of inlet to outlet flow (more drawn out than introduced).

FIGS. 4B-4F show the results of the CFD modeling that was performed for a system with an outlet and an inlet forming an air curtain, and a source within a protected region, in accordance with some embodiments. The modeled system shown in FIGS. 4C-4F included an inlet 1015, an outlet 1016, and a source 1017 of a gas (e.g., a gas containing particles). The model was two-dimensional. The inlet 1015 and the outlet 1016 were each 1 cm tall in the z-direction, and the source was 2 cm wide in the x-direction. The distance 1018 was 55 cm between the inlet 1015 and the outlet 1016. The distance 1019 was 45 cm, as measured from the source 1017 to a horizontal line 1020 connecting the inlet 1015 and the outlet 1016.

The table in FIG. 4B shows the Conditions that were modeled and the results. An air curtain was generated between the air outlet and the air inlet by flowing gas out of the outlet with a rate from 50 L/s to 100 L/s, and flowing air into the inlet at a rate from 100 L/s to 300 L/s.

Figure 4C:
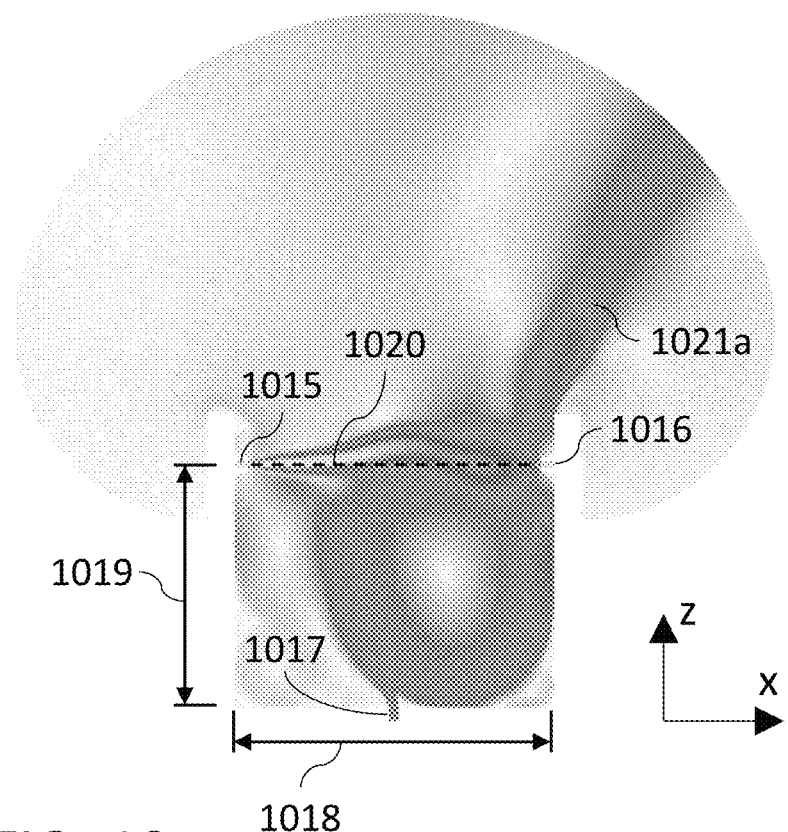
Figure 4D:
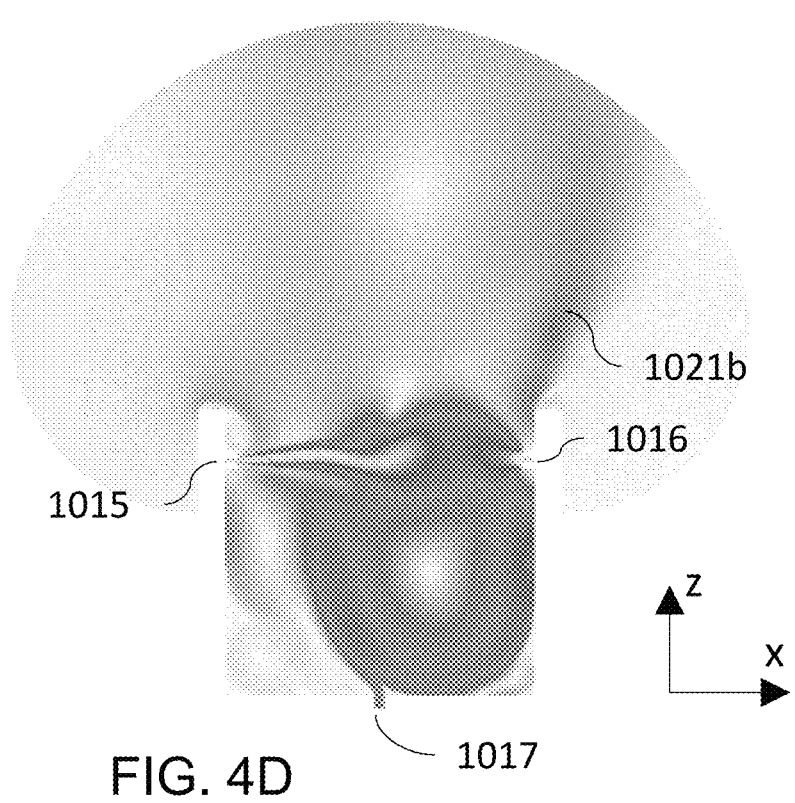
Figure 4E:
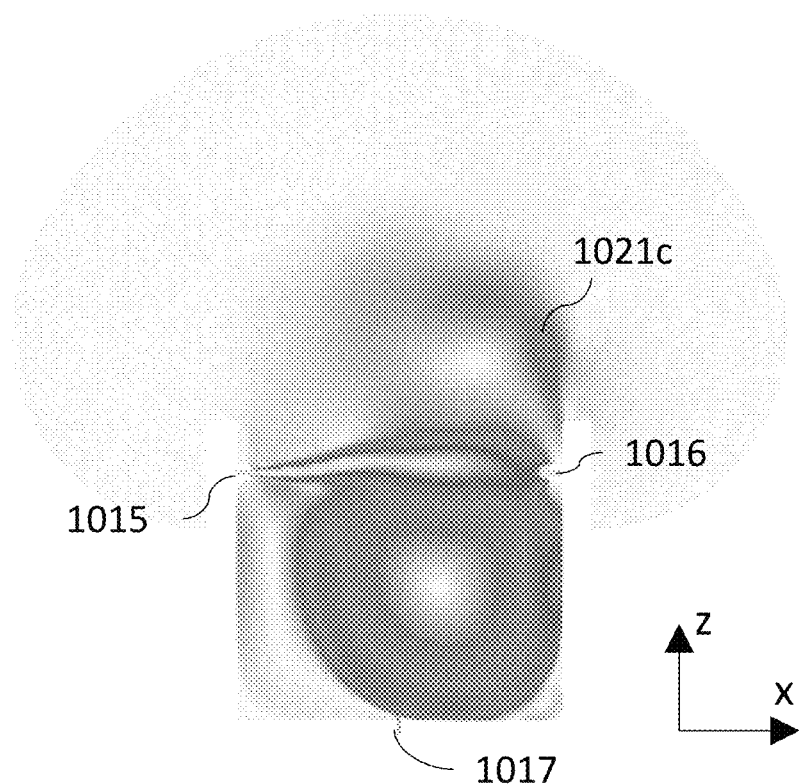
Figure 4F:
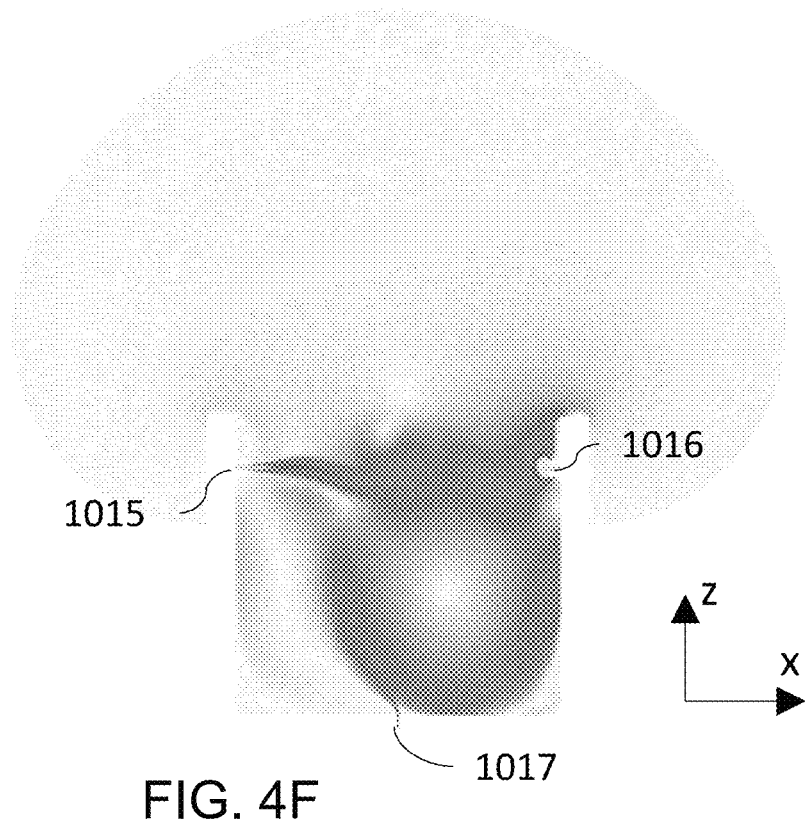

FIG. 4C shows a plot of the modeled gas flow velocity for Condition 1. FIG. 4D shows a plot of the modeled gas flow velocity for Condition 2. FIG. 4C shows a plot of the modeled gas flow velocity for Condition 3. FIG. 4C shows a plot of the modeled gas flow velocity for Condition 4. Condition 1 had the highest ratio of outlet: inlet flow rate (1:1) and was the least effective. In Condition 1, 50% of the source gas escaped past the air curtain. FIG. 4C shows a relatively large velocity of gas 1021*a* that has escaped past the air curtain. Condition 2 had an increased outlet: inlet flow ratio of 1:2 compared to Condition 1, and a 40 L/s source gas flow. The efficiency was improved in Condition 2, where 25% of the source air 1021b escaped past the air curtain as shown in FIG. 4D. Condition 3 also had an outlet: inlet flow ratio of 1:2 but a source gas flow of 8 L/s (which was lower than that of Condition 2). In Condition 3, due to the lower source gas flow rate, only 10% of the source air 1021c escaped past the air curtain, as shown in FIG. 4E. Condition 4 had the highest inlet flow rate of 300 L/s, and the ratio of outlet: inlet flow rate was 1:6, which was the most effective condition modeled. In Condition 4, 99% of the airflow out of the source was collected by the inlet, and only 1% escaped the protected region through the air curtain, as shown in FIG. 4F.

The modeling results summarized in FIGS. 4B-4F indicate that in some embodiments of the systems and methods described herein, a flow rate ratio of an air outlet flow rate to an air inlet flow rate (i.e., outlet flow rate: inlet flow rate) less than equal to 1:2 (e.g., 1:3, 1:4, 1:6, or less than 1:6) can result in the system having at least 90% isolation efficiency. In other words, a flow rate ratio of an air inlet flow rate to an air outlet flow rate (i.e., inlet flow rate: outlet flow rate) of at least 2:1 (e.g., 3:1, 4:1, 6:1, or greater than 6:1) can result in the system having at least 90% isolation efficiency. The isolation efficiency can be a metric for preventing particles from leaving a protected region and/or preventing particles from entering a protected region. In some embodiments, a flow rate ratio of an air outlet flow rate to an air inlet flow rate (i.e., outlet flow rate: inlet flow rate) less than equal to 1:6 (e.g., 1:10, or less than 1:10) can result in the system having at least 99% isolation efficiency.

Figure 5:
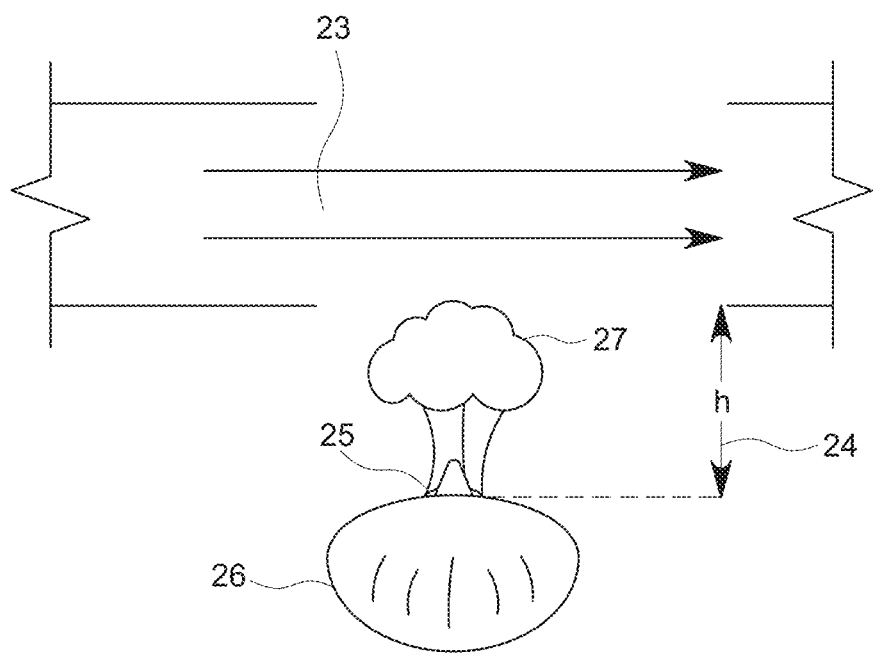
FIG. 5 shows a schematic example of an air curtain placed with a distance in front of the mouth of a person, in accordance with some embodiments.

FIG. 5 shows a schematic example of an air curtain 23 placed with a distance 24 in front of the mouth 25 of a person 26 (e.g., a patient, seen from the top of their head), in accordance with some embodiments. In this manner, there is additional time from the exhalation of particles 27 to when the particles 27 enter the moving air of air curtain 23. This gives the particles 27 time to slow down. Further, it is more comfortable for the person or patient as they are not in the direct air curtain 23. In another embodiment, the air curtain 23 may be positioned close to or inclusive of the person's mouth 25.

In some cases, the systems and methods described herein provide an air flow or air curtain to prevent a person or patient from being exposed to pathogens or other harmful species in the environment. For example, a patient may not have a communicable respiratory disease, and it may not be necessary to isolate their exhaled air, but it may be desirable to protect said patient from pathogens in their immediate environment. In some cases, the systems and methods described herein provide an air flow or air curtain to prevent a person or patient from being exposed to pathogens or other harmful species in the environment, or other harmful material in the air, such as particles or chemicals, and also to contain pathogens from the person or patient and prevent them from entering the environment. The air curtains of the systems and methods described herein can effectively capture pathogens or any particles from both inside (e.g., as shown in FIG. 5) and outside a zone within the air curtain. For example, the particle 21 in FIG. 4A can be a particle from the outside environment and the person or patient can be on the opposite side of the air curtain 19.

Figure 6:
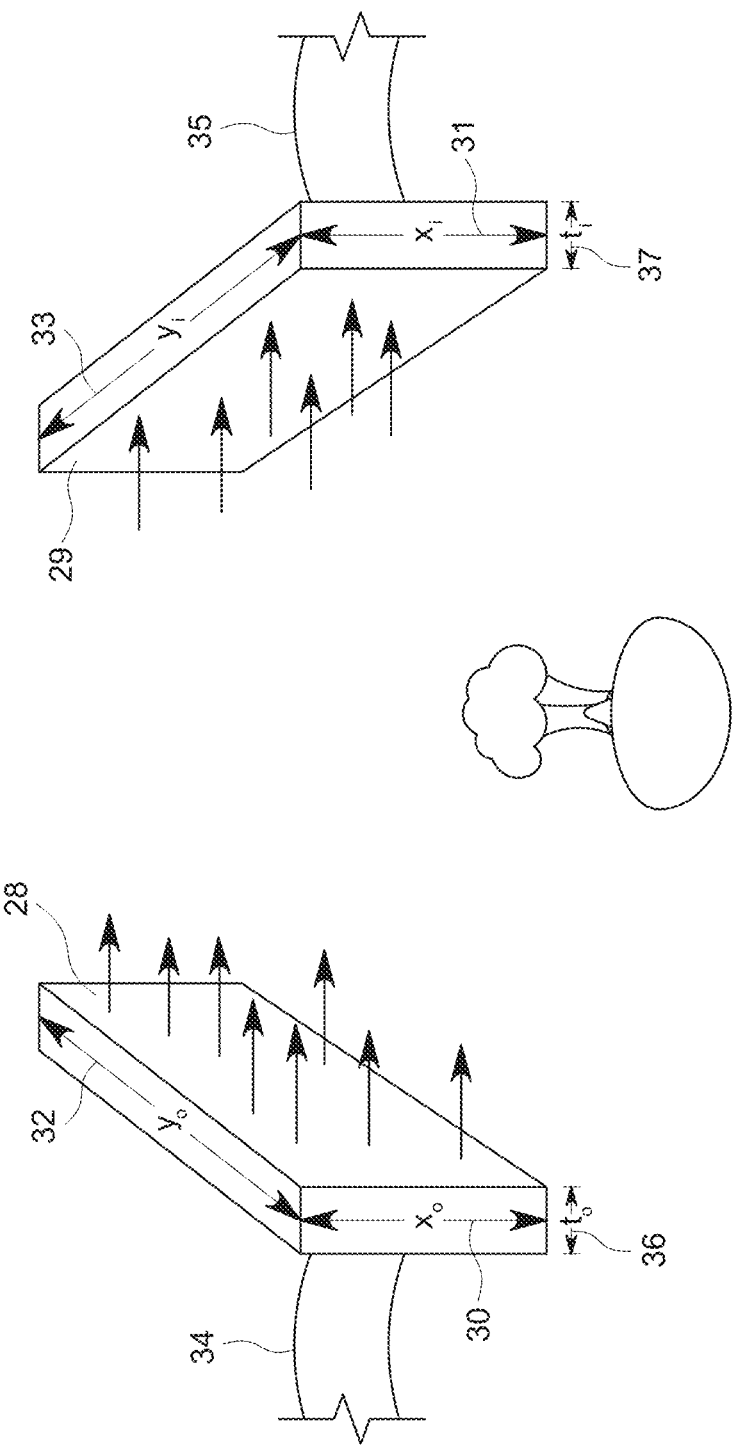
FIG. 6 shows an example wherein the outlet and the inlet are generally planar, in accordance with some embodiments.

FIG. 6 shows an example wherein the air outlet 28 and the air inlet 29 are generally planar, in accordance with some embodiments. The air outlet 28 and the air inlet 29 in this example may have an area that is generally rectangular or ovoid with dimensions 30 and 31 (labeled $x_o$ and $x_i$) in direction that are away from the person or patient, and dimensions 32 and 33 (labeled $y_o$ and $y_i$) that are along the length of the person and perpendicular to dimensions 32 and 33. Dimensions $x_o$ and $x_i$ are similar to dimension 20 (labeled w) in FIG. 4A, and represent an approximate thickness of an air curtain produced using outlet 28 and inlet 29. Dimensions $x_o$, $x_i$, $y_o$, and $y_i$ can be from about 1 cm to about 100 cm, or more than 100 cm, or about 5 cm, or about 10 cm, or about 20 cm. The airflow can be laminar as it exits the air outlet 28, and in some cases, is substantially or generally uniform across the face. The faces may present a resistance to flow to aid in spreading out the pressure inside the air outlet 28 and air inlet 29 so that the flow of air is more uniform, and uniform in collection, while supplied and collected into ducts or conduits 34 and 35. The thicknesses 36 and 37 (labeled $t_o$ and $t_i$) of the injector and collector of the air outlet and the air inlet, respectively, may be considered thin in that they are much less than $x_o$, $x_i$, $y_o$, or $y_i$. In some cases, the thicknesses 36 and 37 may be in the range of about 2 cm to about 5 cm. In some cases, the diameter of conduit 34 or 35 coupled to or feeding the outlet 28 or the inlet 29 is a factor of several (e.g., from about 2 to about 5, or from about 2 to about 10, or from about 2 to about 100) times smaller than the dimensions of the plane of the air outlet 28 or air inlet 29. In some cases, there is a relationship between the uniformity of flow, the resistance of the air leaving or entering the air outlet 28 or air inlet 29, and the thickness $t_i$ or $t_o$, where uniformity of the produced air curtain increases with increasing thickness $t_i$ or $t_o$ and increasing resistance. In such systems, for a constant uniformity, if the thickness is decreased, the resistance must increase, and vice versa.

In general, for a given air volume flow, it is preferable to have $x_o$ and $x_i$ (related to the thickness of a produced air curtain) as large as possible. While the air speed across the curtain will decrease linearly, the power law of injected particle deceleration dominates and collection ability increases. That is, in general for improved capture efficiency, it is better to have a thicker air curtain rather than a fast air curtain. If $y_o$ or $y_i$ is increased, to maintain the same capture efficiency, it is necessary to linearly increase the volume of air flow to maintain the speed of the air flow in the air curtain.

In some cases, $x_o$ can be smaller than $x_i$, such that as the airflow in the air curtain spreads out, there is more area of the air inlet 29 to capture the air.

Figure 7:
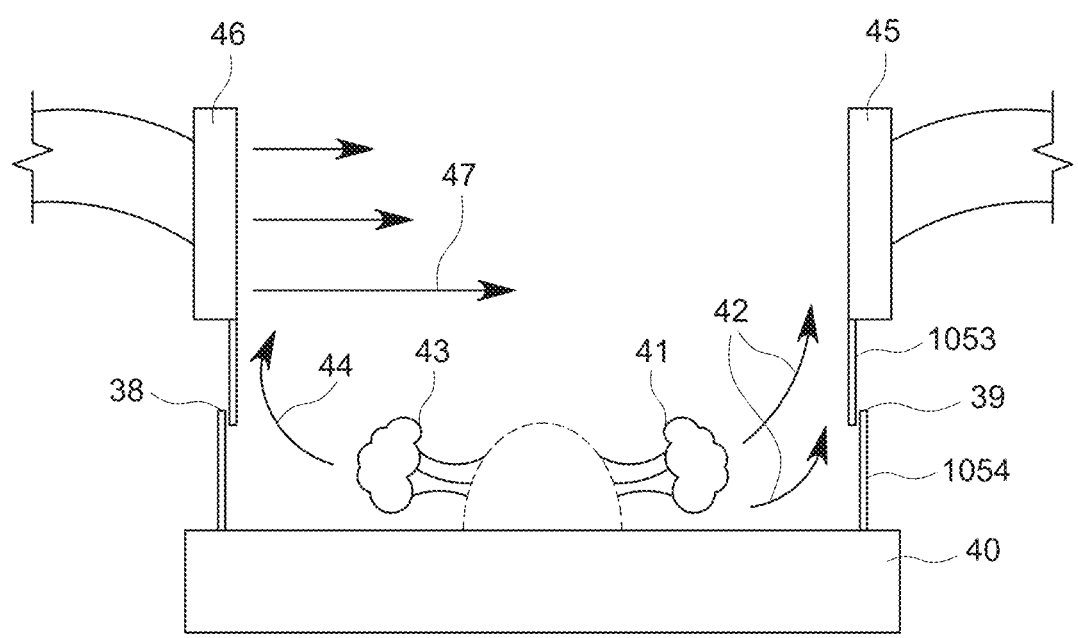
FIG. 7 shows a schematic example including shields that extend from the edge of the outlet and inlet to a fixed surface, where the shields form a generally continuous barrier to air flow, in accordance with some embodiments.

FIG. 7 shows a schematic example including shields 38 and 39 that extend from the edge of the air outlet 46 and air inlet 45 to a fixed surface 40 (e.g., a bed), in accordance with some embodiments. In this example, the shields 38 and 38 form a generally continuous barrier to air flow between the fixed surface 40 and outlet 46 or the inlet 45 respectively. When air is exhaled in a direction 41 that is sideways towards the barrier or shield 39 and perpendicular to a direction towards the air curtain 47 (e.g., when a patient's head is sideways on a bed), it may encounter the shield 39 and flow upwards 42 into the airstream 47. Similarly, when air is exhaled in a sideways direction 43 it will run into barrier or shield 38 and flow upward 44 into the airstream 47. In this manner, the shields 38 and 39 can help capture exhalations from all directions or substantially all directions (left to right) from a patient. In some cases, the shields may be expandable or include a plurality of sliding components 1053 and 1054. In some cases, the shields 38 and 39 are movable such that they allow access to the space between the air curtain 47 and the fixed surface 40 through the shields 38 and/or 39. For example, shields 38 and 39 can be made from a stretchable material, a plastic sheet, a strip curtain, an elastomeric material, or a textile material.

The systems and methods described herein can have an adjustable height between the air curtain 47 and a fixed surface 40 (e.g., a bed) bounding the isolated space inside the air curtain. For example, the air outlet 46 and the air inlet 45 in the system in FIG. 7 could be moved closer to the fixed surface 40, and shields 38 and 39 could be made shorter. In some cases, there is a trade-off where moving the air curtain 47 closer to the fixed surface improves the efficiency of the isolation but makes it harder to access the isolated space (because the air outlet and air inlet block the access), and moving the air curtain 47 farther from the fixed surface reduces the efficiency of the isolation but makes it easier to access the isolated space (e.g., through movable shields 38 and 39).

Figure 8:
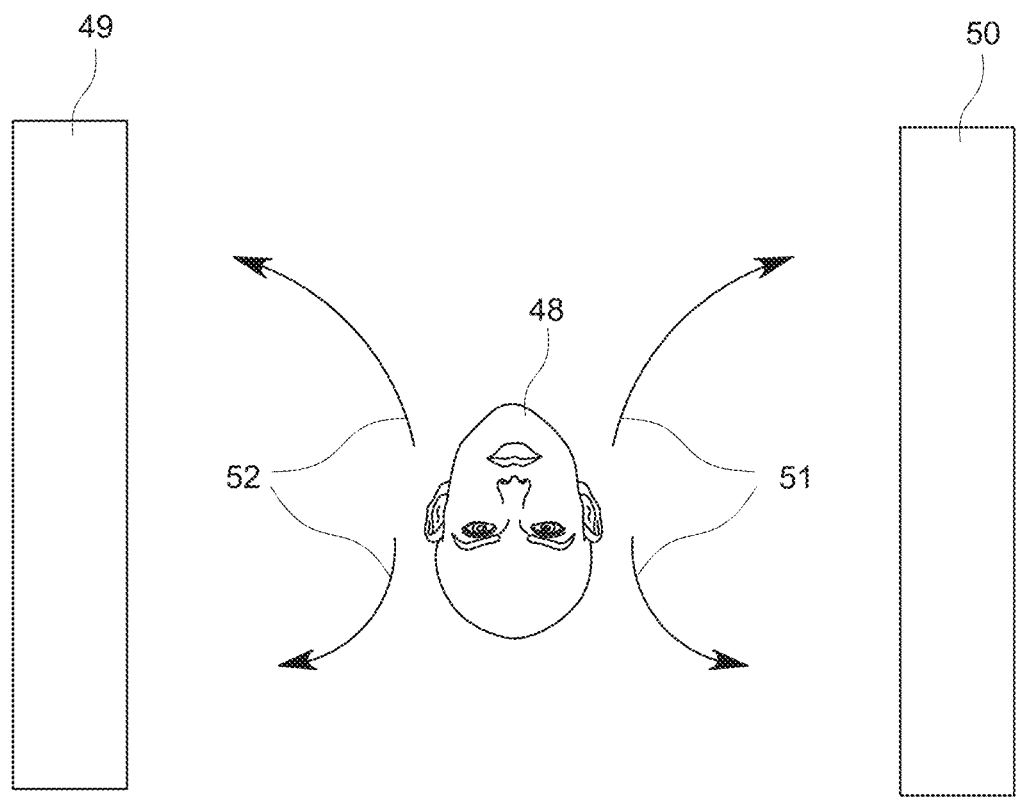
FIG. 8 shows a view of the system shown in FIG. 6 from above, looking down on a person or patient, for example when they are lying in bed, in accordance with some embodiments.

FIG. 8 shows a view of the system shown in FIG. 6 from above, looking down on a person or patient for example when they are lying in bed, in accordance with some embodiments. In this embodiment, the dimension $y_i$ and $y_o$ of the system shown in FIG. 8 of air outlet 49 and air inlet 50 are sufficiently long to capture diffusing air that is exhaled from a person 48 or patient in directions 51 and 52 before exhaled particles can enter the room towards the feet of the person 48 or above their head. In some cases, the speed of air in the directions 51 and 52 is generally much less than directions 41 and 43 shown in FIG. 7 (which are generally straight out of the mouth).

Figure 9:
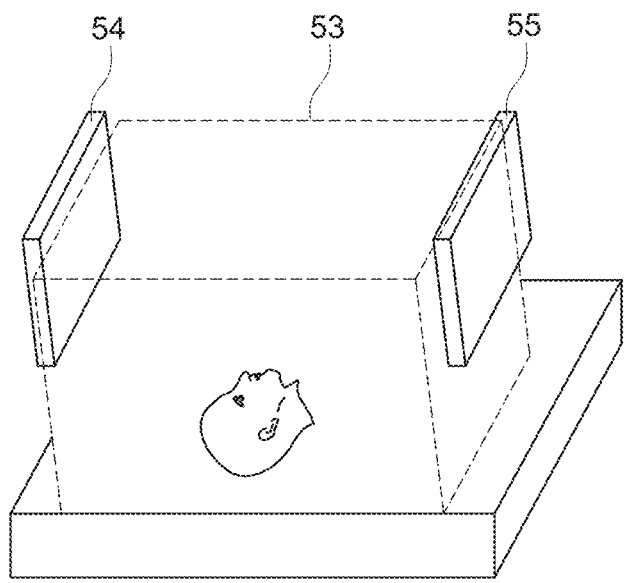
FIG. 9 shows a schematic example of an outlet and an inlet which form an air curtain between them, and effectively contain pathogens exhaled by the person in a zone, in accordance with some embodiments.

FIG. 9 shows a schematic example of an air outlet 54 and an air inlet 55 which form an air curtain between them, and effectively contain pathogens exhaled by the person in zone 53, in accordance with some embodiments.

Figure 10:
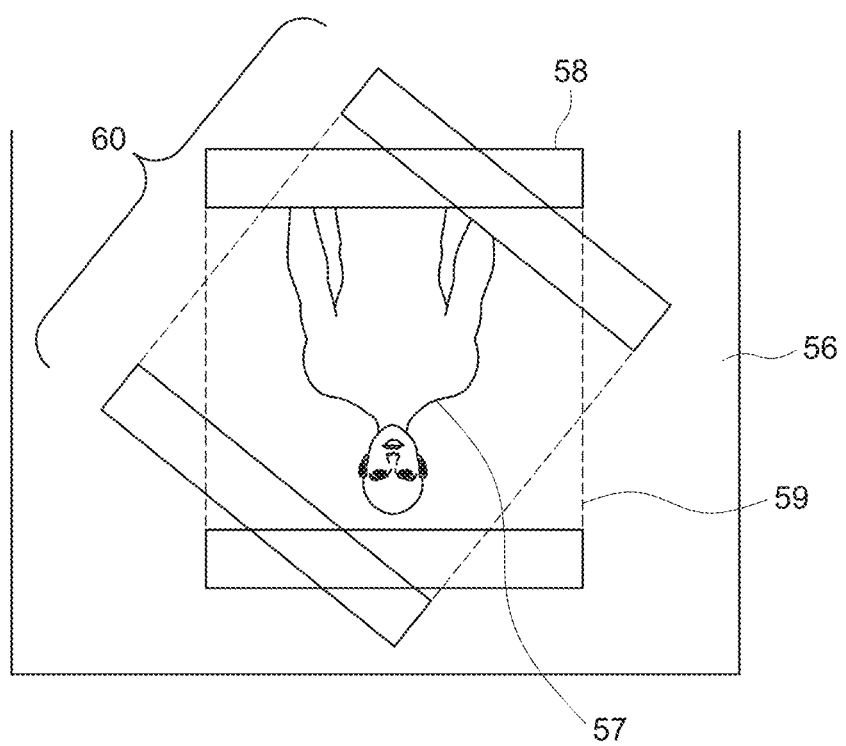
FIG. 10 shows a schematic example of a system with an air outlet and an air inlet, wherein the air curtain flows in various directions, in accordance with some embodiments.

FIG. 10 shows a schematic example of a system with an air outlet and an air inlet, wherein the air curtain flows in various directions, in accordance with some embodiments. A person 57 is shown lying on a bed 56. The outlet and the inlet can be arranged as shown in arrangement 58, such that the air curtain flows from the head of the person 57 towards the feet of the person 57. The air outlet and the air inlet can be arranged as shown in arrangement 59, such that the air curtain flows at another angle, such as a 45-degree angle to the person 57. Such alternate configurations may afford improved access or comfort to the person 57 or patient. In some cases, the systems for producing air curtains described herein may be adjustable. For example, the air outlet and air inlet relative positions can be fixed, and they can be rotatable together as shown in FIG. 10. The relative position of air inlet and air outlet may generally be the same to maintain the same effectiveness. In some cases, the air inlet and air outlet may be adjustable, such that they can be moved closer for greater effectiveness, or farther for reduced effectiveness and improved access and comfort when needed.

Figure 11:
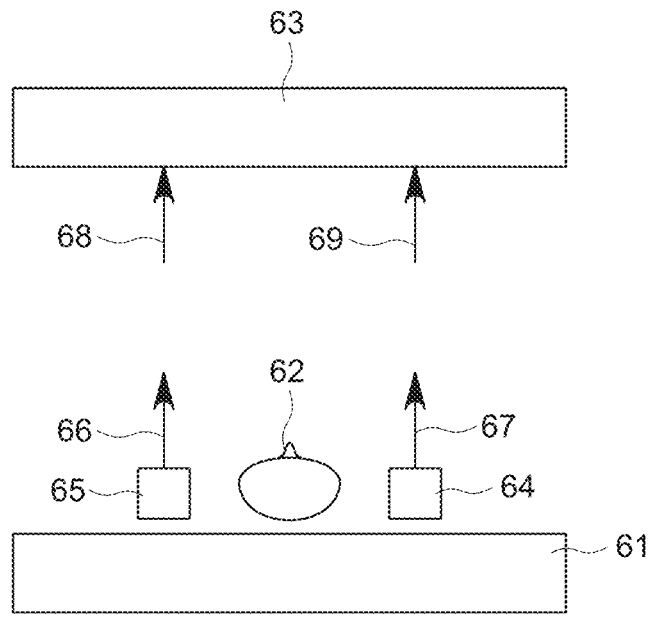
FIG. 11 shows a schematic of an example in which air flows generally up from a bed with a person, in accordance with some embodiments.

FIG. 11 shows a schematic of an example in which air flows generally up from a bed 61 in a vertical direction with a person 62 or patient, in accordance with some embodiments. Air outlets 64 and 65 provide airflow 66 and 67 to an air inlet 63, wherein airflow 66, 67, 68 and 69 create a vertical (i.e., a direction normal to a main surface of the bed) air curtain around the patient. The air outlets 64 and 65 may be in a single unit or multiple units, or may be a ring, or may be arch-shaped, or may be flexible and lie on the bed, or be held via an arm off the bed. The dimensions of the inlet 63 in the plane of the bed may be less than a lateral spacing between outlets 64 and 65 along the bed, in some cases 0.5 or 0.25 or 0.1 times the spacing between 64 and 65, where in this configuration the outlets are configured to direct air upwards and inwards to reach the smaller inlet 63. In another embodiment, the width of inlet 63 is greater than the spacing between outlets 64 and 65, with air directed outwards.

Figure 12:
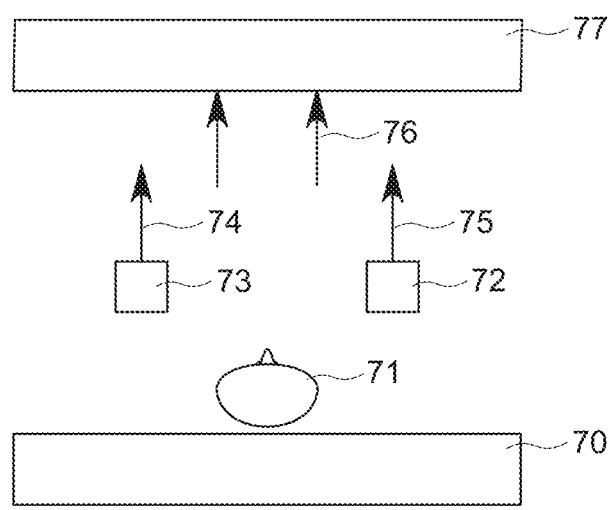
FIG. 12 shows a schematic of an example where a person lies on a bed and one or more outlets direct airflow towards an inlet, in accordance with some embodiments.

FIG. 12 shows a schematic of an example where a person 71 or patient lies on a bed 70 and air outlets 72 and 73 with airflow 74 and 75 is directed towards an air inlet 77 with airflow 76, in accordance with some embodiments. The air outlets 72 and 73 and air inlet 77 may be supported by one or more arms (not shown, which can be coupled (or mounted) to the bed, a floor unit, or a wall or ceiling. Similar coupling or mounting possibilities are disclosed for the previous embodiments herein.

The systems, subsystems, and configurations described herein may be effectively applied in various environments. A person or patient may be lying in a bed, sitting in a chair, on a couch, or on a bean bag chair, or standing, and the systems described herein can be used to form a zone wherein pathogens exhaled by a person can be effectively contained. In addition to being used in conjunction with a bed, the systems and methods described herein may be applied to a chair, such as a dental or optical chair.

Figure 13:
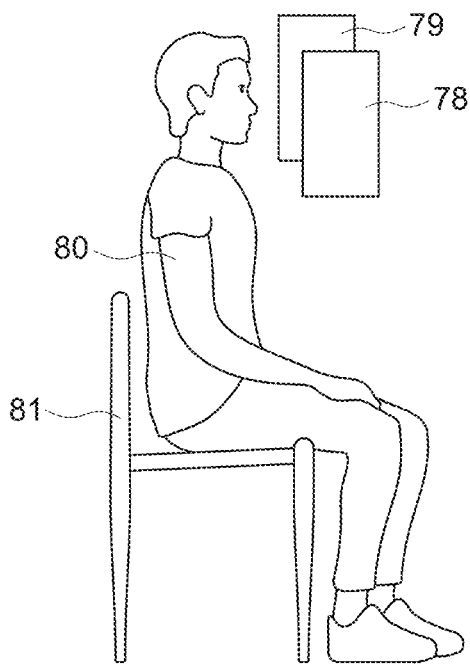
FIG. 13 shows a schematic of an example where a person is sitting in a chair, and an air inlet and outlet are used to form an air curtain, in accordance with some embodiments.

FIG. 13 shows a schematic of an example where a person 80 is sitting in a chair 81, and air inlet 78 and air outlet 79 are used to form an air curtain in accordance with some embodiments. The air inlet 78 and air outlet 79 may be mounted to a support structure (not shown) connected to, or independent of, a chair. The support structure may provide adjustability, such as an arm mounted to a portable base on the floor.

Figure 14:
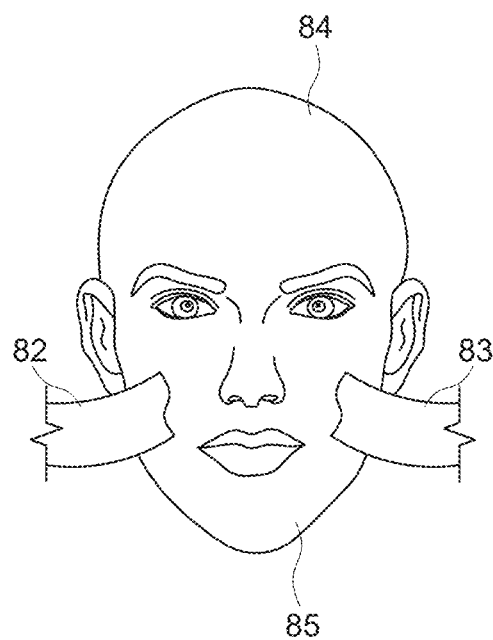
FIG. 14 shows a schematic of an example of an outlet and inlet that are placed in close proximity to a patient's mouth, in accordance with some embodiments.

FIG. 14 shows a schematic of an example of an air outlet 82 and air inlet 83 that are placed in close proximity to a patient's 84 mouth 85, and nose, in accordance with some embodiments. Such a system may be self-contained (e.g., worn by the patient) or connected to a base unit (e.g., using an arm). For example, the system in FIG. 14 can mount to the shoulders and be worn while a patient is sitting or standing.

Figures 15A, 15B:
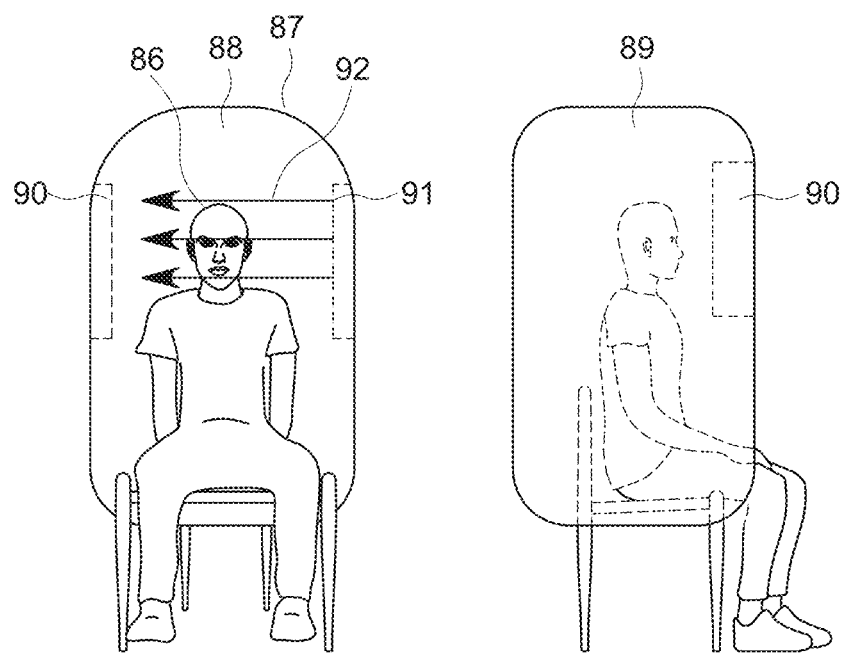
FIGS. 15a and 15b show respective front and side view schematics of an example system for forming a zone where pathogens exhaled by a person can be effectively contained, in accordance with some embodiments.

FIGS. 15a and 15b show respective front and side view schematics of an example system for forming a zone wherein pathogens exhaled by a person can be effectively contained, in accordance with some embodiments. FIGS. 15a and 15b show a containment chair system 87 where a person 86 or patient sits in a chair system 87 with an opening 88 that is otherwise closed on all other sides 89 as a barrier to air flow. The chair system has an air inlet 90 and an air outlet 91 (such as those previously described) forming an air curtain 92 across the opening 88 of the chair. The air curtain 92 may extend partially or completely from top to bottom of the opening 88 of the chair.

In some embodiments, the systems and methods for forming a zone where pathogens exhaled by a person can be effectively contained can include air handling systems, which may contain subsystems for heating and humidifying the air in the aforementioned systems. The humidifying or heating subsystems may be manually or automatically adjusted to a predetermined humidity value such as by an operator by incorporating the output from a humidity or temperature sensor. Additional subsystems may introduce liquids or solids or chemicals such as medicines into the air stream to benefit the patient or the environment.

Figure 16:
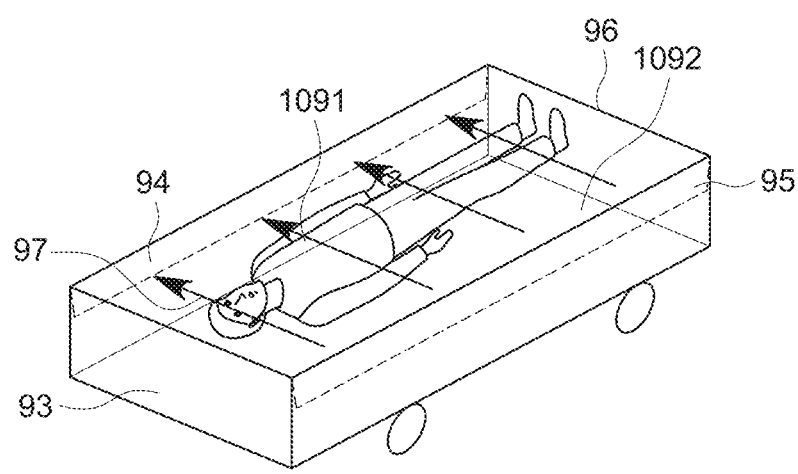
FIG. 16 shows a schematic of an example of an isolation bed system, in accordance with some embodiments.

FIG. 16 shows a schematic of an example of an isolation bed system, in accordance with some embodiments. In this example system, a patient 1091 lies on a bed 1092 surrounded by airflow barriers 93 that form a continuous or semicontinuous wall or barrier to airflow extending upwards from the bed. For example, the patient's body and members can generally be below a top edge 96 of the barrier 93. An air curtain 97 covers the opening (or substantially all, or a part of the opening) with an air inlet 94 and air outlet 95 disposed along the length of the generally top edge 96 of the barrier 93. This isolation bed system affords a pathogen containment system that has openings via an air curtain. In some cases, a portion of the opening (e.g., below the face or below the chest or below the waist of the patient) may be closed with additional barriers. For example, a portion of the opening can be covered with a rigid or soft additional barrier. For example, a blanket can be affixed to the outside or edges of two or more of the airflow barriers 93 so that it is suspended. In this manner, less air flow is needed, as it is needed only for the open parts, and the air supply can be reduced, or turned off in the region under the barrier (or cover). In some cases, the airflow barrier 93 may be flexible along its length, or be jointed, so that the bed may be repositioned (e.g., into reclining positions).

In some embodiments, the systems and methods described herein may contain alarms and alarm subsystems. The processor of the device can be coupled to sensors to detect various air flow conditions, and other events. Alarms may be triggered by events, for example, that are detected by the sensors. Some events that could trigger alarms include: airflow blockage (such as a clogged filter, or reduced fan capacity, which can be detected by one or more flow meters); misalignment of air inlet(s) and air outlet(s) (may be detected by optical sensor, camera, or other sensor subsystem to indicate relative position or distance); patient movement out of zone (may be detected by optical image analysis, e.g., by locating a marker previously affixed to the patient or their clothing, such as a fluorescent dot); filter maintenance time; low flow compared to patient exhale rate (via sneeze detector using a sound sensor, or optical turbulence measurement); or air curtain interruption (may detect an object in the path of the air curtain such as via optical sensor). Air pressure sensors may also be disposed to detect pressure in the isolation region, in an air curtain, or in a conduit. Air temperature and/or humidity sensors may also be included to detect the temperature and/or the humidity of air in the system or moving through the system. The system may also contain alarms for maintenance, such as filter changes.

In some embodiments, systems used for beds may be mountable on the bed including the subsystems such as controls, device(s) that motivate air flow, and air cleaning, along with a portable electrical power subsystem, such that the containment system can be transported with the bed. Such a system can be advantageous, for example, as a patient is moved around a hospital.

In some cases, the systems and devices described herein can be configured to be coupled to a bed, where a component of the system is in the proximity of a region of the bed. For example, coupling the systems described herein to a bed can include mounting a component of the system (e.g., an air inlet or outlet) on the floor, and positioning the component to be aligned with a region of the bed (e.g., next to an edge of the bed, over an edge of the bed, or over a central region of the bed). In another example, an air outlet can be mounted to an arm that is coupled to a base, and the arm can be used to position the air outlet over (or next to) a head, foot, or side of the bed. In some cases, coupling the systems described herein to a bed can include mounting a component of the system (e.g., an air inlet or outlet) to the bed, for example, to a frame, headboard, leg, or post of the bed. In some cases, a component of the system (e.g., an air inlet or outlet) can be coupled to the bed by mounting the component to the bed using a mounting system configured to movably couple the component to the bed, such that, for example, an arch maintains a fixed position relative to a bed component when the bed component is moved.

Figure 17:
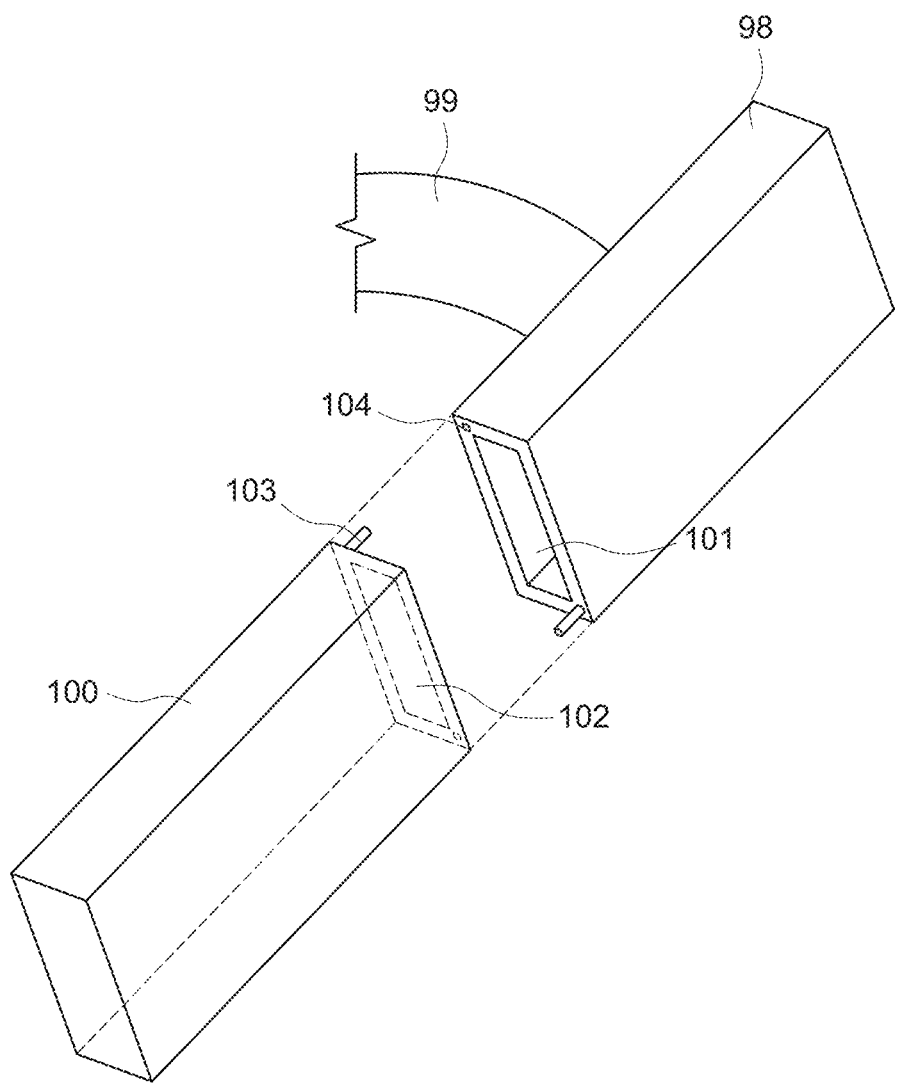
FIG. 17 shows a schematic of an example wherein an inlet or outlet can be modularly extended, in accordance with some embodiments.

FIG. 17 shows a schematic of an example wherein an air inlet or air outlet can be modularly extended, in accordance with some embodiments. In FIG. 17, an air inlet or air outlet subsystem 98 with a conduit 99 may be coupled to a second air inlet (or outlet) subsystem 100 with mating openings 101 and 102. Mating openings 101 and 102 can include doors that open when air inlet (or outlet) subsystem 98 is attached to air inlet (or outlet) subsystem 100. In other cases, mating openings 101 and 102 can have covers that are manually removed prior to coupling air inlet (or outlet) subsystem 98 to air inlet (or outlet) subsystem 100. The two units may have coupling locking mechanisms and alignment mechanisms, such as a pin 103 and a corresponding hole 104. The pin and hole may be any shape, where the pin and hole are a generally matching shape, such as a ridge and a slot, or the pin may be a protrusion with an asymmetrical outline such that it only enters a matching shaped hole in a pre-determined orientation. There may be a plurality of such coupling subsystems at a coupling interface.

The systems and methods described herein include air inlets and air outlets that provide an air curtain. The air that flows out of the air outlet and into the air inlet flows through openings or ports in the air outlet and air inlet, respectively. The openings (or ports) in the air inlets and air outlets that allow air to flow through may be adjustable in any system described herein. For example, the size of the openings or the shape of the openings can be adjusted, for example, using a valve.

The air inlets and air outlets of the systems and methods described herein can be shapes other than rectilinear, for example, they may contain arcuate edges and surfaces. The air inlets and outlets may be adjustable, for example to form an arch that may be configured into different shapes. For example, arch-shaped inlets and/or outlets may contain flexible segments and rigid segments, or be composed of a flexible material, or be composed of rigid segments with hinges between segments, or a combination of these. The arches may also be extensible and compressible, so as to form longer or shorter arches, where segments may telescope into each other, or segments may stretch or extend such as by conduits that have a zigzag and flexible structure along their length, as in common flexible plastic drinking straws.

Figure 18:
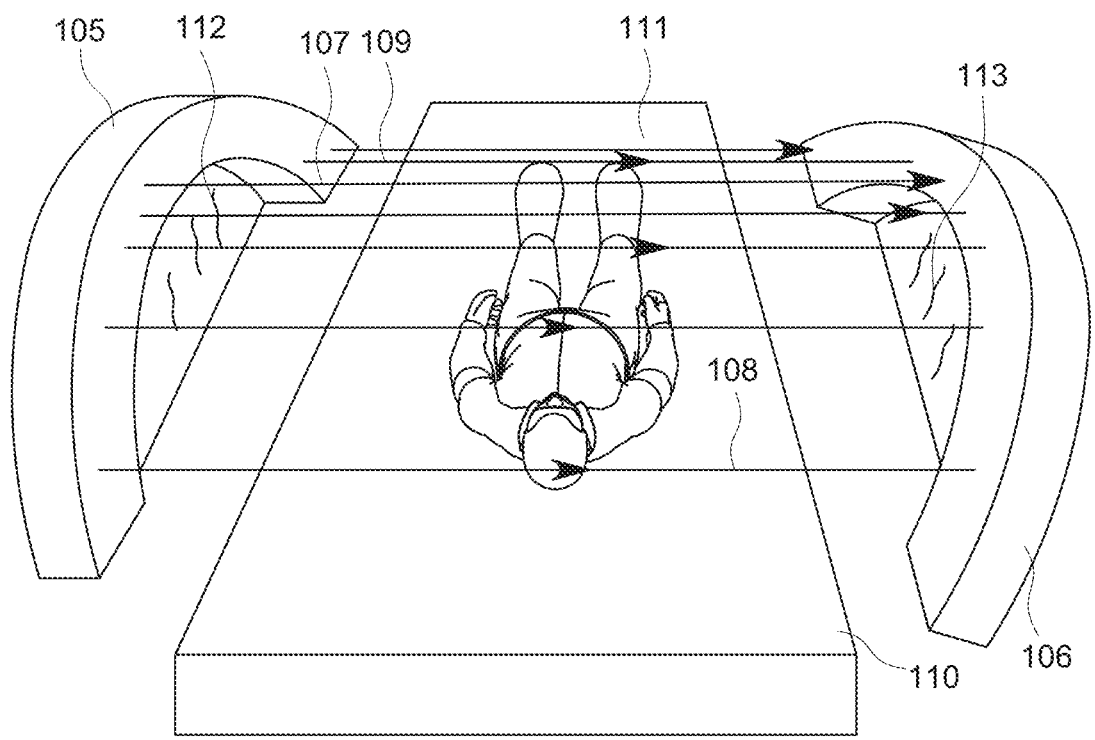
FIGS. 18 and 19 show schematics of an example wherein the outlet and the inlet are arch-shaped, in accordance with some embodiments.
Figure 19:
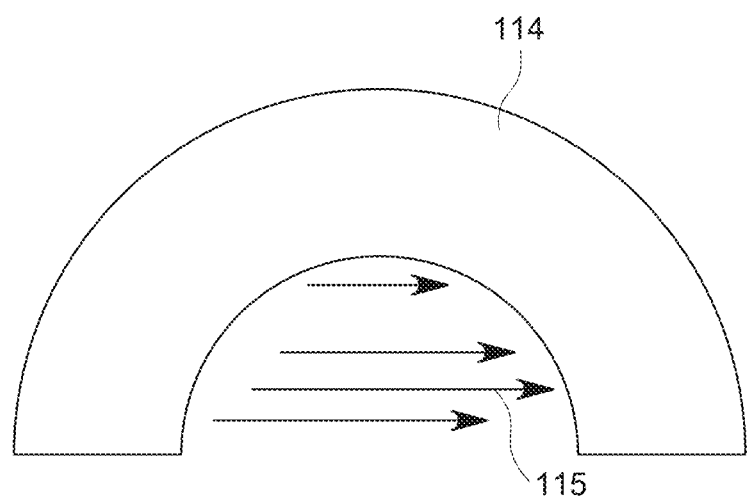
Figure 20:
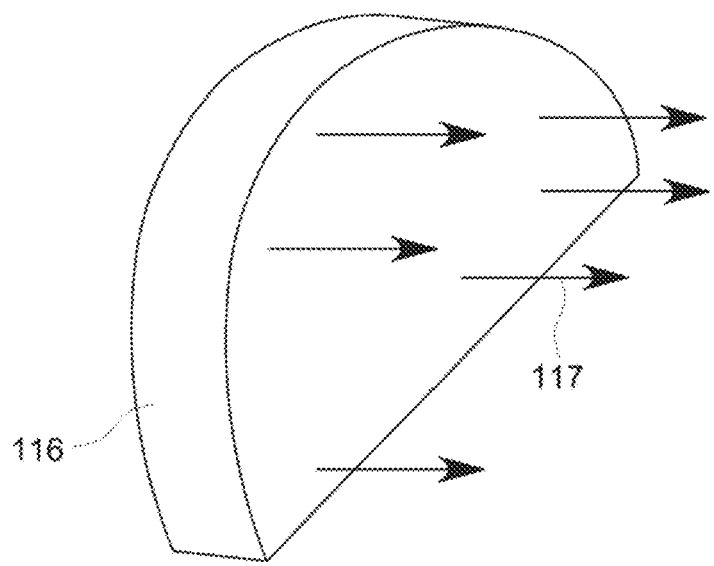
FIG. 20 shows a schematic of an example where the outlet emits air generally across its surface, in accordance with some embodiments.

FIG. 18 shows a schematic of an example wherein the air outlet 105 and the air inlet 106 are arch-shaped, in accordance with some embodiments. The arch-shaped air outlet 105 and the arch-shaped air inlet 106 are shaped generally in ares in this example, where the air curtain 107 at one end 108 is in close proximity to a fixed surface 110 (such as a bed or a wall) and a second end 109 is also in close proximity to a second surface 111 (such as the lower part of a bed). The air inlet and air outlet of the systems and methods described herein may be arch-shaped (i.e., they may have a cross-section that is arch-shaped), for example, be an arc of a circle, a section of an oval, three sides of a rectangle, composed of sides of a polygon, or other shape that forms an arch. Likewise, the profile of the air curtain 107 may be arch-shaped, for example, be an arc of a circle, a section of an oval, three sides of a rectangle, composed of sides of a polygon, or other shape that forms an arch. In some cases, the air curtain 107 forms a generally (or substantially) complete enclosure in concert with an air barrier surface (e.g., a wall, bed, or other solid surface). The inside of the arch-shaped outlet 105 and inlet 106 may be a barrier 112 and 113, respectively, that may be transparent, translucent, or other light transmissive value. Barrier 112 and/or 113 can be solid barriers, non-rigid barriers, movable barriers. The inside of an arch-shaped inlet or outlet 114 is shown in FIG. 19, where it includes an air curtain 115 in place of an air barrier. The air curtain 115 within the arch-shaped inlet or outlet may be in the plane of the arc. The inside of the arc of an inlet or outlet may be filled and also be a source of air. FIG. 20 shows a schematic of an example where the air outlet 116 emits air 117 generally across its whole surface, in accordance with some embodiments.

The systems and methods described herein can include arch-shaped air inlets and air outlets, with barriers (e.g., barrier 112 and 113 in FIG. 18) across an inside of the arch-shaped air inlet or outlet. The barriers can be solid barriers, made from a material such as a piece of rigid plastic, to block the flow of air through the inside of the arch-shaped air inlet or outlet. The barriers can also be non-rigid barriers, made from a material such as a stretchable material, a flexible plastic sheet, a strip curtain, an elastomeric material, or a textile material. The lower edges of a non-rigid barrier may have weights to hold the barrier down to conform to a surface such as a patient.

In some embodiments, the barriers (e.g., barrier 112 and 113 in FIG. 18) can also be movable barriers. Movable barriers can be either made from rigid materials that are movably coupled to the arch-shaped air inlet or air outlet, or they are made from non-rigid materials that can be moved (e.g., a flexible plastic, a strip curtain, or a textile material). For example, a movable barrier can include a rigid material coupled to the arch-shaped air inlet or air outlet using one or more hinges (or any movable mount) such that the barrier can be swung open (like a door) to allow access through the arch-shaped air inlet or air outlet. In another example, a movable barrier can include a strip curtain made of plastic or textile strips coupled to the arch-shaped air inlet or air outlet such that the strips can be independently moved out of the way to allow access through the arch-shaped air inlet or air outlet. In another example, the barrier can be made from a rigid material that is removably coupled to the arch-shaped air inlet or air outlet (e.g., using magnets), such that the barrier can be removed from the arch-shaped air inlet or air outlet to allow access through the arch-shaped air inlet or air outlet. The movable barriers can be advantageous to both improve isolation of a region between the air curtain and a surface (e.g., a bed) and allow access to the space when needed.

In some cases, the air outlets and/or air inlets of the systems described herein can be movable, or repositionable. For example, the arch-shaped air outlet 105 and/or arch-shaped air inlet 106 could be mounted using a mounting system configured to movably couple to the arch-shaped air outlet such that a position of the arch-shaped air outlet with respect to the bed is maintained. The mounting systems for the systems described herein can include a floor standing base, or can be configured to mount to another object such as a wall, or a table, or the bed to which the system is coupled. Accordingly, the movable or repositionable mechanisms of the mounting systems can also be floor mounted, or can be mounted to another object such as a wall, or a table, or the bed to which the system is coupled. The mounting may have subsystems that allow the arches to be moved into positions that disrupt the air curtain but improve patient access, such as sliding down towards the floor, swinging outwards rotating about an end of the arch, sliding horizontally towards the head or foot of the bed, lifting up in the plane of the arch hinging around an end of the arch, sliding along a path that extends from the curve of the arch, folding inwards or outwards with both ends of the arch having hinges, segments of the arches having hinges such as for example an arch having a hinge in the middle of the arch such that half an arch can move rotatably inwards or outwards, or both arches may readily rotate such that both arches remain upright with respect to the bed, and remain in the same position relative to each other.

For storing the arches, the arches may be composed of segments that connect end to end and are separable or hinged. The arches may also have segments that fit inside one another so that the arch may telescope.

In some embodiments, the mounting system can be configured such that the arch-shaped air outlet 105 and/or arch-shaped air inlet 106 retracts below the surface of the bed (like the movement of a car window). For example, the mounting system could include guiding elements (e.g., rails, or tracks, or linear gears, or screws, or any linear movement mechanism), and the arch-shaped air outlet 105 and/or arch-shaped air inlet 106 could be moveably coupled to the guiding elements, for example, using one or more mating elements (e.g., protruding tabs, rails, wheels, and/or gears) that are guided by the guiding elements.

In some embodiments, the mounting system can enable the arch-shaped air outlet 105 and/or arch-shaped air inlet 106 to rotate with respect to the bed. Such a mounting system could include one or more rotation elements (e.g., a hinge, a pivot, a swivel joint, a slotted ball joint, a universal ball joint, or any rotating movement mechanism) coupled to the arch-shaped air outlet 105 and/or arch-shaped air inlet 106 to enable them to rotate with respect to the bed. For example, the arch-shaped air outlet 105 and/or arch-shaped air inlet 106 could rotate along a vertical rotation axis and swing out from the edge of the bed (like the movement of a car door). In another example, the arch-shaped air outlet 105 and/or arch-shaped air inlet 106 could rotate along a horizontal rotation axis and rotate orientation so that one side moves up away from the bed (like the motion of a gull-wing car door).

Figure 21A:
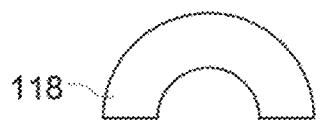
FIGS. 21A-21G show examples of arch-shaped inlets or outlets with different cross-sectional profiles, in accordance with some embodiments.
Figure 21E:
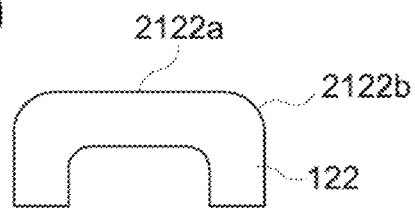
Figure 21B:
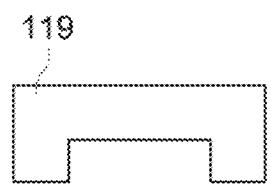
Figure 21F:
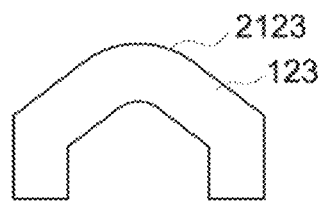
Figure 21C:
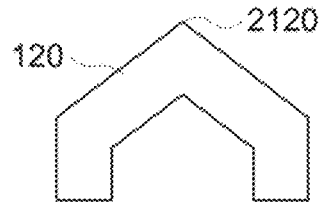
Figure 21G:
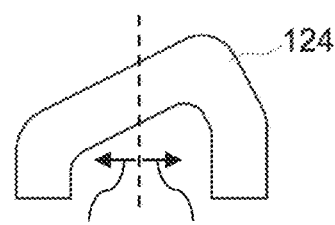
Figure 21D:
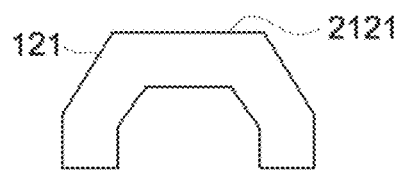

Various embodiments of arch-shape inlets or outlets with different cross-sectional profiles are illustrated in FIG. 21A-21G. FIG. 21A shows an example of an arch-shaped inlet or outlet with a cross-section 118 that is arcuate. FIG. 21B shows an example of an arch-shaped inlet or outlet with a cross-section 119 that is rectilinear. FIG. 21C shows an example of an arch-shaped inlet or outlet with a cross-section 120 that is a multi-angled polygon, where angles at vertices may vary, and there may be an apex 2120. FIG. 21D shows an example of an arch-shaped inlet or outlet with a cross-section 121 that is a polygon, where different sides may have different lengths, and there may be a generally flat or horizontal high point 2121. FIG. 21E shows an example of an arch-shaped inlet or outlet with a cross-section 122 that is a rounded-vertex polygon, where the profile may contain a combination of straight section 2122*a* and arcuate sections 2122*b*. FIG. 21F shows an example of an arch-shaped inlet or outlet with a cross-section 123 that is a combination of arcuate and angled vertices, where there may be an arcuate apex 2123. FIG. 21G shows an example of an arch-shaped inlet or outlet with a cross-section 124 that is an asymmetric shape. For example, an arch-shaped inlet or outlet may have a cross-section that is asymmetric such that there may be more space near where a person's head may be under the arch-shaped air curtain. The example in FIG. 21G has an asymmetric shape such that a first side or portion 2124*a* of the arch-shaped air outlet or inlet is farther away from a top surface of the bed than a second side or portion 2124*b* of the arch-shaped air outlet or inlet, such that there may be more space under the arch-shaped air curtain on the first side or portion 2124a than the second side or portion 2124b.

The term arcuate, as used herein, means any path that contains curves, and may contain straight segments. The term barrier is used to mean any surface with a material that limits or prevents air from passing through the surface (as contrasted with an air curtain, which also limits or prevents air from passing through, but has no solid material in it).

In some cases, the outlets and inlets of the systems and methods described herein are configurable to source or vacuum air. For example, the system may include pathogen deactivation subsystems on both of the outlet and inlet conduits or ducts, so that the direction of the air flow can be reversed. This may be particularly useful if one of the sides needs to be moved to a position out of the way of the person or patient. The system may include subsystems that allow repositioning of the inlets or outlets. To continue effective pathogen collection when one side is moved out of the way, that side may be turned off, and the remaining side be configured to vacuum air as an inlet, or expel air for a one-sided air curtain. It may be preferable to increase the flow rate in such configurations to a high level. Such sufficient flow rates may create sound at a level that is undesirable, but may be acceptable for short procedures such as repositioning or replacing the inlet and/or outlet.

The arched inlets and outlets may be configured with the flow in a direction other than across a bed, but in another direction, at any angle between 0 degrees (across the bed) to 90 degrees (along the length of the bed). This latter position is a preferred position as may allow the greatest access to the patient.

Figure 22:
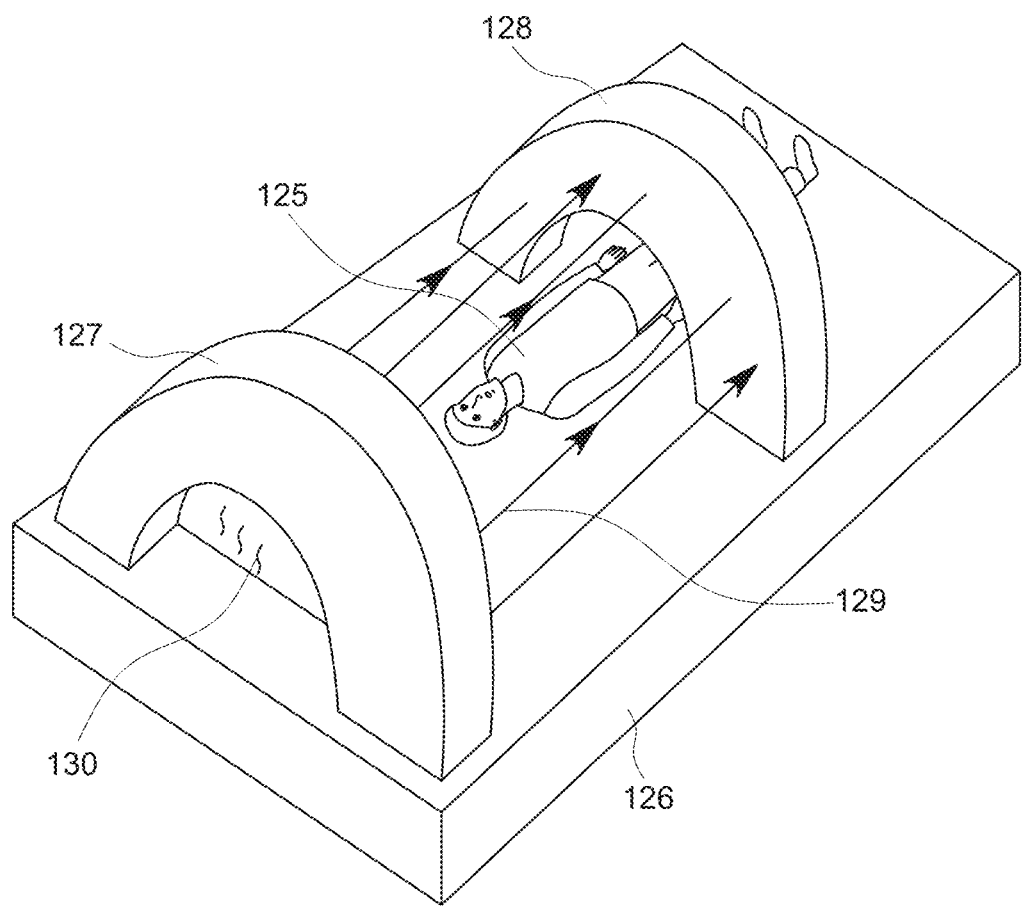
FIG. 22 shows a schematic of an example where a patient lies on a bed, with an arch-shaped air outlet and an arch-shaped air inlet forming an air curtain, in accordance with some embodiments.

FIG. 22 shows a schematic of an example where a patient 125 lies on a bed 126, with an arch-shaped air outlet 127 and an arch-shaped air inlet 128 forming an air curtain 129, in accordance with some embodiments. The region inside (or under) the arch-shaped air inlet 128 over the body may be open, or be comprised of a movable barrier, for example including a flexible barrier material, or strips of barriers material that can move independently. The region 130 inside (or under) the arch-shaped air outlet 127 at (or near) the head of the bed may be a solid barrier material or a flexible material generally the same as inside the arch-shaped air inlet 128 over the body of the person 125. The air may flow from the head of the person 125 towards the feet of the person 125, as shown in FIG. 22 with arch-shaped air outlet 127 and arch-shaped air inlet 128, or the air inlet and the air outlet can be switched and air may flow from the feet of the person 125 towards the head of the person 125. In the example configuration shown in FIG. 22, the body of the person 125 extends through one of the arches (arch-shaped air inlet 128). There can be a barrier across the inside of the arch (e.g., a flexible material, a textile material, or strips of material), but the other arch (arch-shaped air outlet 127 in FIG. 22) can, in some cases, include a more effective barrier material (e.g., a rigid material) since the body of the person 125 does not need to extend through it. In such cases, it may be more effective for containment to have the air move in a direction from the legs of the person 125 towards the head of the person 125. Not to be limited by theory, air moving in the air curtain towards an arch may tend to entrain air to move through the arch if no barrier (or an insufficient barrier) is present. Air that passes through the arch would not be collected by the arch-shaped air inlet and would not be contained. In some cases, the arch that is positioned between the head of the bed and the foot of the bed (arch-shaped air inlet 128 in FIG. 22) may be positioned at or below a patient's waist, so that it doesn't interfere with their hand and arm movements.

The barriers across the inside of the arch-shaped air inlet 128 can also be movable barriers that are advantageously used to allow a part of a body of person 125 to extend through the inside of the arch-shaped air inlet 128 while an effective isolation space is maintained. For example, the movable barrier can be a strip curtain (made from plastic strips, textile strips, or a combination or materials), a flexible plastic material, or a textile material that can block air flow from moving through the inside of the arch-shaped air outlet past the body of person 125.

Figure 23A:
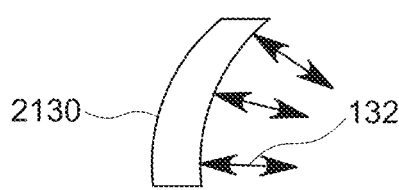
FIGS. 23A-23E show schematics of examples of arches that are curved or angled out of a vertical plane, in accordance with some embodiments.
Figure 23B:
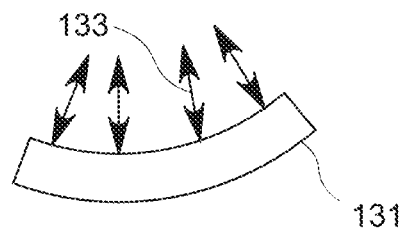
Figure 23C:
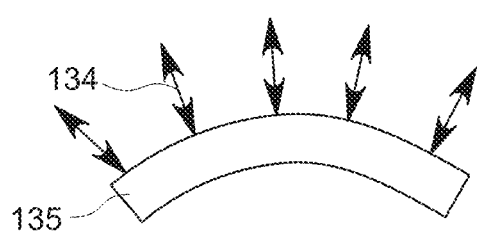
Figure 23D:
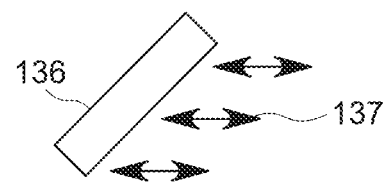
Figure 23E:
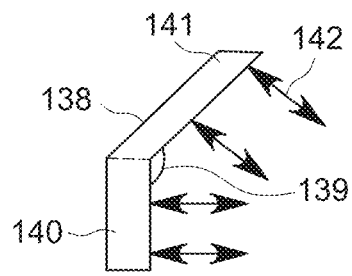

FIGS. 23A-23E show schematics of examples of arches that are curved or angled out of a vertical plane, in accordance with some embodiments. FIG. 23A illustrates a side view of an arch 130 with airflow 132 either in or out, where the arch generally bends inwards over the person or patient in an arcuate fashion or a combination of linear or arcuate segments. FIG. 23E shows a side view of an example arch 138 with segments 140 and 141 with air 142 going in or out which meet at an angle 139 less than 180 degrees, where there may be two or more segments. The profile of the arches in the systems and methods described herein can be any curvilinear form. The arch may curved or bent away from the vertical plane as well. For example, the arch can be bent or curved (at least partially) around a vertical axis that is generally convex towards the patient, as shown in FIG. 23B which is a top view of an arch 131 with air 133 either going in or out. The curve of the arch 131 may contain one or more arcuate and/or linear segments. The curve may also be generally concave towards the patient, as shown in FIG. 23C that shows a schematic of a top view of an arch 135 and air 134 either going in or out of the arch. The arch may also bend inwards or outwards to the patient, as shown in FIG. 23D with a side view of an arch 136 angled towards a patient with air 137 going in or out. The angled-in arch may include linear or arcuate segments, as exemplified in FIG. 23E with an arch 138 with generally linear segments 140 and 141 meeting at an angle 139 which is less than 180 degrees, with air 142 going either in or out. The segments 140 and 141 may be arcuate or linear, and may be a combination of linear and arcuate, where there may be a plurality of segments, or the profile may follow any trajectory.

Figure 24:
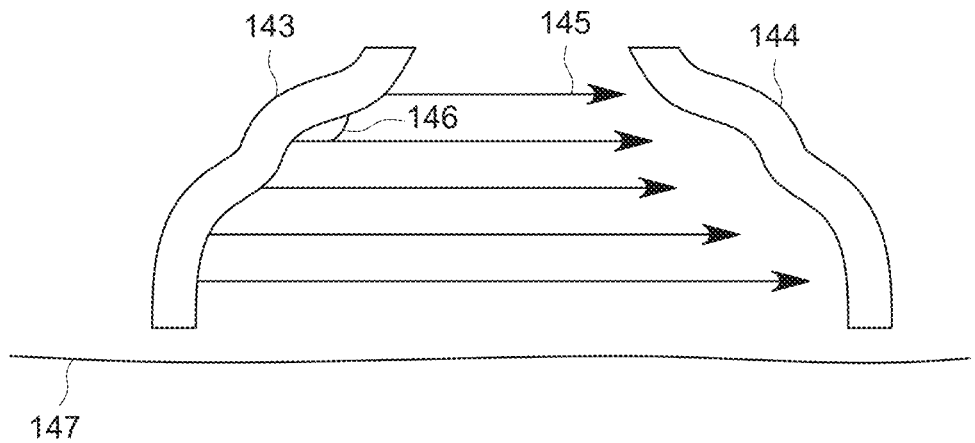
FIG. 24 shows a schematic of an example where arches shown in a side view have an arcuate form, yet the air is configured to travel generally parallel to a surface, in accordance with some embodiments.

The angle at which the air leaves or enters the arch may be such that the air is parallel to a surface defined by a plane below the arches, such as a bed, while the surface of the arch where the air enters or exits may or may not be perpendicular to this plane. This is exemplified in FIG. 24, which shows an example where arches 143 and 144 shown in a side view have an arcuate form yet the air 145 is configured (e.g., by a suitable arrangement of vents or louvers within the arches) to travel (or leave or enter the arches at angles that are) generally parallel to a surface 147, in accordance with some embodiments.

An arcuate arch, or an arch with linear segments, that bend toward one another (e.g., towards an apex or top of an arch), may have the advantage of reducing the distance between arches which may increase the capture efficiency of the system or afford reduced airflow while having a comparable capture efficiency to planar arches. The capture efficiency is the amount of particulates either contained or excluded by the air curtain. Such an arch may yet afford an open feel for patients and open access for caregivers.

In some embodiments, a single arch delivering air may be employed to provide an air flow, or air curtain. For example, a patient may not have a communicable respiratory disease, and it may not be necessary to isolate their exhaled air, but it may be desirable to protect said patient from pathogens in their immediate environment. Thus, it can be desirable to create a shield of air (or air flow, or air curtain) that protects the patient from pathogens in the environment. Such a shield may be accomplished by using an arch to deliver air, generally in the form of an air curtain. The air curtain may form a shield over the patient such that pathogens in the air are blown past the patient and back into the environment.

Figure 25A:
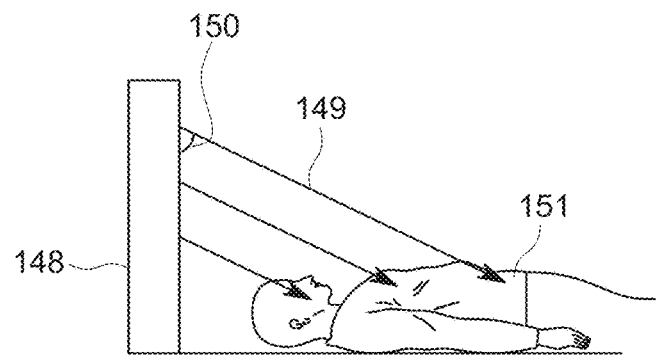
FIGS. 25A and 25B show schematic examples of a single arch delivering an air curtain to form an air shield over a person, in accordance with some embodiments.
Figure 25B:
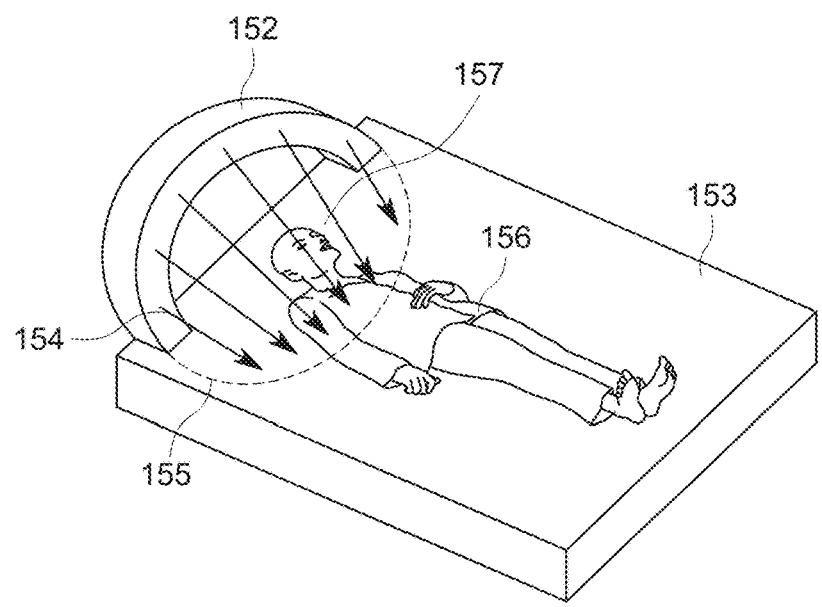

FIGS. 25A and 25B show schematic examples of an arch delivering an air curtain to form an air shield over a person or patient, in accordance with some embodiments. In FIG. 25A, a sideview of a person 151 lying on a bed is shown with an arch 148 delivering air 149 at an angle 150 which is less than 90 degrees and configured by suitable vents in the arch to angle the air down to the bed, thus forming a curved layer of moving air (with an arch-shaped cross-section) over the patient that connects the arch and the bed so as to form a closed environment. The inside of the arch can be of an air-impenetrable material, such as a solid material, or a flexible material. Any of the arch-shaped outlets described herein can be used in such a single-arch application. FIG. 25B illustrates a three-dimensional view of such a system, where an arch 152 is disposed generally at the head of a bed 153 with air 154 angled to hit the bed 153 along a line 155 (dashed line) over a person 156. The air layer can have a thickness of about 1 inch to about 6 inches. Thus, a region 157 is formed between the air curtain, the bed and the person, and the arch including the inner closed surface of the arch, that is isolated from pathogens in the environment. The arch 152 may have any of the configurations or shapes described elsewhere herein.

The arch may preferably contain light sources that illuminate a pattern on the bed surface that is generally the same as the location where the air from the air curtain touches the surface, thus indicating where the edge of the contained region is located. This may be advantageous for users so that they know if a person is within the safe region.

Figure 26:
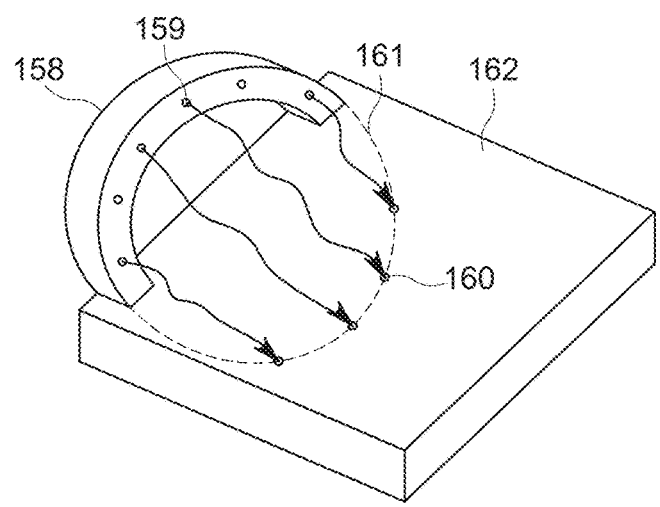
FIG. 26 illustrates an embodiment, where an arch (similar to the arches in FIGS. 25A and 25B) contains light sources that illuminate regions generally on a line that is generally the same as where the air curtain lands on the bed and person, in accordance with some embodiments.

FIG. 26 illustrates an embodiment, where an arch 158 (similar to arch 148 and 152 in FIGS. 25A and 25B) contains light sources 159 that illuminate regions 160. The combination of such illuminated regions falling generally on a line 161 that is generally the same as where the air curtain lands on the bed 162 and person (not shown), in accordance with some embodiments. The light sources may be LEDs, lasers, or other lamps. Lasers may be low-powered Class I lasers (less than 5 mW as used in laser pointers). The light sources may form illumination regions that are spots or lines configured to generally lie along the path 161. In some cases, light sources 159 can include lasers with suitable optics to focus the light into a line. Further, a laser source may contain a system of optics to scan a beam such that a single source may repeatably trace a line 161 at a rate that is sufficiently rapid to appear as a continuous illumination. The system may contain a single such source, or a plurality of sources. A control system may have an interface that allows an operator to turn on or off the illumination system.

The system illustrated in FIGS. 25A and 25B may further contain a subsystem for configuring the position of the air curtain. Such a subsystem may include subsystems to direct the air exiting the outlet ports such as movable conduits or louvers that are adjustable such that the line 155 may be adjusted. The line 155 generally indicates a region where air 157 impinges upon a surface such as bed 153 and person 156 and may have a width generally perpendicular to the line 155, and a length consisting of all or a portion of the dashed line 155. Such a subsystem may have multiple manual adjustment points, a single adjustment point that adjusts all air control subsystems, or a system of actuators that adjust the air control subsystems such that the air curtain position may be configured from a control interface. For example, a smaller person may only require a smaller isolation region, which may be advantageous as when the air travels a shorter distance, the isolation efficiency may be improved.

A system with a single arch such as in FIGS. 25A and 25B may be combined with other arch features indicated herein, including those in FIGS. 23A-23E and 24, and other arch features mentioned in this application, such as arch shape.

Figure 27:
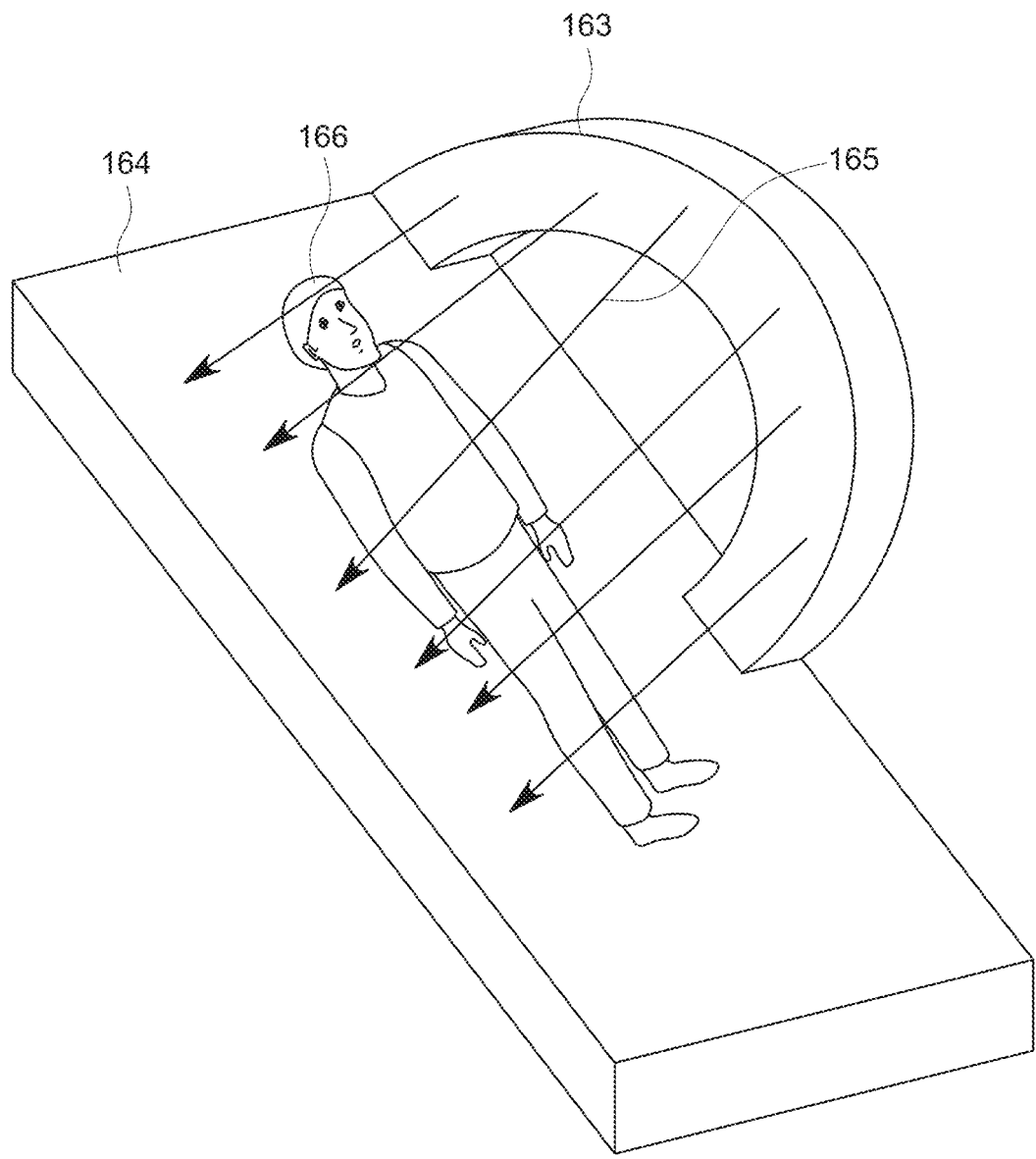
FIG. 27 shows a schematic of an example including an arch positioned generally on the side of a bed, or in close proximity to, the edge of a bed, in accordance with some embodiments.

FIG. 27 shows a schematic of an example including an arch 163 positioned generally on the side of a bed 164, or in close proximity to the edge of a bed 164, in accordance with some embodiments. Air curtain 165 may be directed toward the bed over a patient 166 generally enclosing them, or a portion of them, for example their head.

In a further embodiment, an air curtain may be disposed to be generally vertical above a bed and generally form a wall around a patient in the bed.

Figure 28:
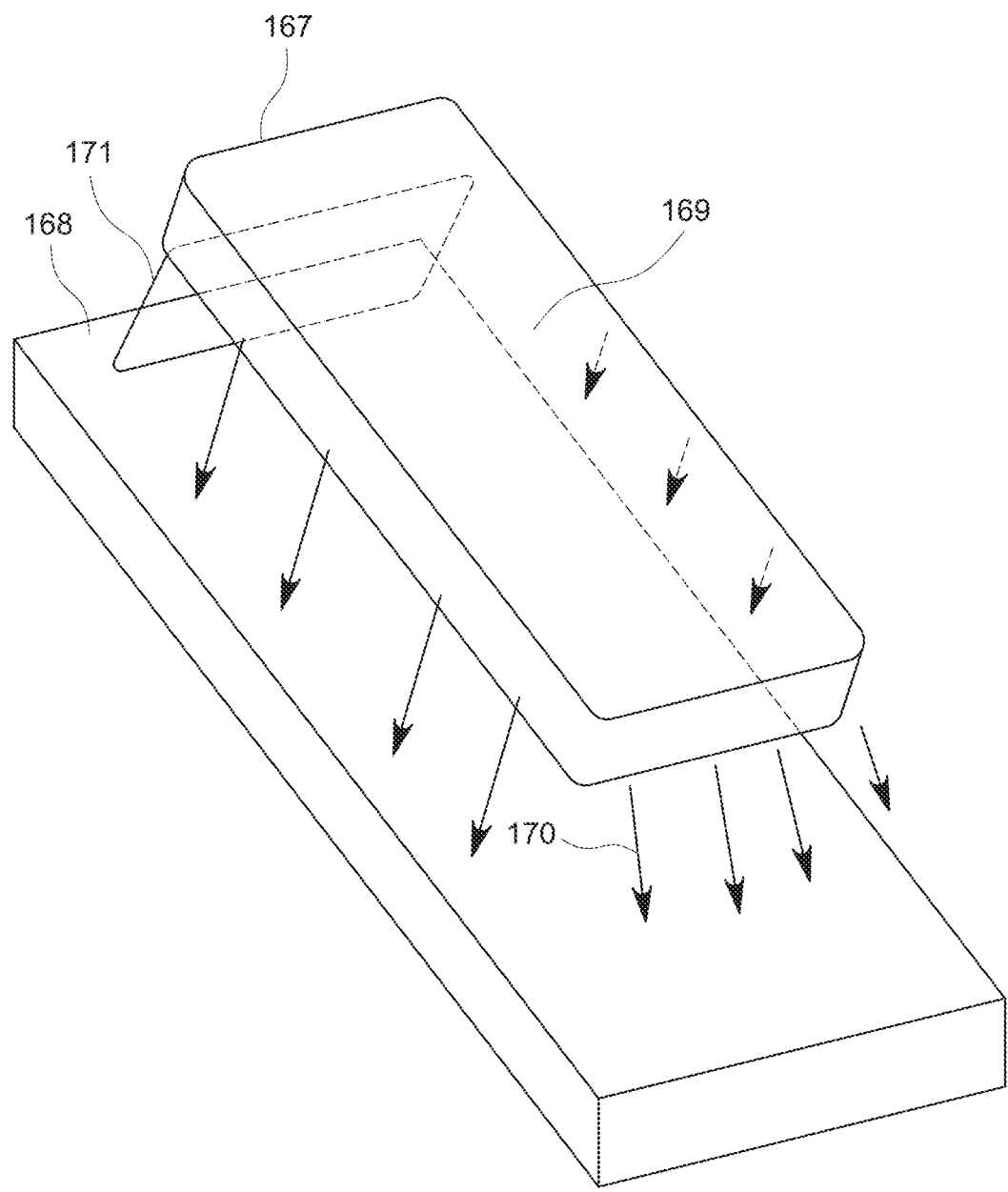
FIG. 28 shows a schematic of an example including a subsystem for delivering air to form an air curtain with generally downward flowing air, in accordance with some embodiments.

FIG. 28 shows a schematic of an example including a subsystem 167 for delivering air to form an air curtain 170 with generally downward flowing air, in accordance with some embodiments. In some cases, the air is angled (e.g., from a few degrees to as much as 45 degrees) outward from a center of the bed towards an edge of the bed, such that particles entrained in the air flow are generally pushed off of the bed instead of potentially back onto the bed. In this example, subsystem 167 is disposed above a bed 168 by a support subsystem (not shown) (e.g., 1 foot, 2 feet, 3 feet, or 4 feet, or from 1-4 feet above the bed). The subsystem 167 delivers air generally around its perimeter and is impermeable to air along generally continuous surface 169.

In some embodiments, a subsystem 171 containing an air-impermeable material may be disposed between a lower edge of the air delivery subsystem 167 and the bed 168 so as to form an air-impermeable wall along a certain region. The material may be rigid or flexible, and is preferably flexible and/or transparent. The material of subsystem 171 may be a curtain slidably mounted on the subsystem 167 so as to be easily positioned by an operator. There may be none or a plurality of such wall subsystems, such as a curtain at the head and foot of a patient, thus conserving air and improving isolation efficiency.

The general width and length of the air delivery subsystem 167 in the plane of the bed may be greater than, equal to, or less than that of the bed. For example, in some embodiments, the width of the subsystem 167 is less than that of the bed, where the air is directed straight down to the bed to form an enclosed region having a width less than the bed, or directed in an outward angle to generally impact the edge of the bed thus forming an enclosed region having width approximately equal to that of the bed. The perimeter of the subsystem 167 may be rectangular, ovoid, or a combination of shapes, so as to optimize for different use cases accessibility, patient comfort and mobility, and isolation effectiveness.

Figure 29A:
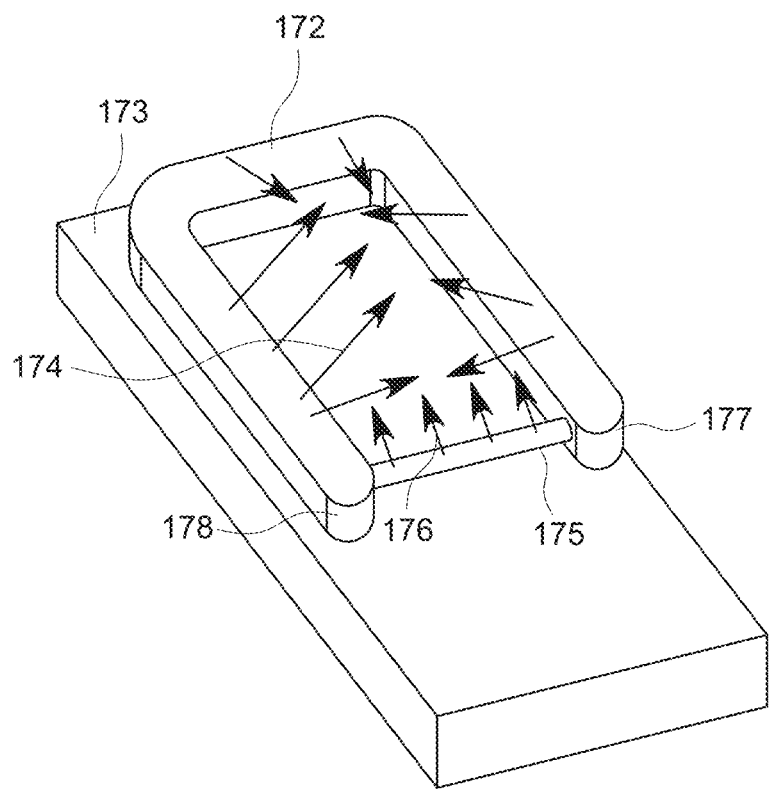
FIGS. 29A and 29B show schematics of an example wherein a source of air is generally in the plane (or in proximity to the plane) of a bed and moves air upwards and inwards to form a shielded region over a patient, in accordance with some embodiments.
Figure 29B:
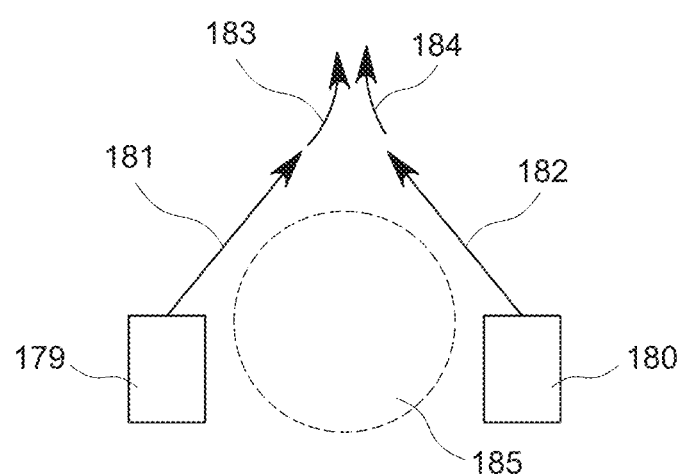

FIGS. 29A and 29B show schematics of an example where a source of air is generally in the plane (or in proximity to the plane) of a bed and moves air upwards and inwards to form a shielded region over a patient. A subsystem 172 that delivers air 174 can be coupled to (or mounted on) a bed, or can be arranged near the edge of a bed 173. A subsystem may also be implemented to complete the shield across a patient's body, where a subsystem 175 is a means for transmitting air such as a tube that can preferably flexibly conform to a surface containing a patient where an air curtain 176 is generally emitted upwards (above the patient). The air-transmitting subsystem (e.g., a conduit or duct containing one or more devices that motivate air flow) may be connected to the subsystem 172 such as at region 177 to supply air to the subsystem 172, or subsystem 172 can have its own source of air flow (e.g., one or more fans). The air curtain generated can generally lie along a path between the ends of the subsystem 172, from region 177 to region 178, which can form a perimeter around a patient, or a portion of a patient (e.g., their head). The air 174 is generally aimed upwards (away from the bed) and inwards (towards the patient). FIG. 29B shows a cross section of 172, where the air-carrying conduits 179 and 180 have air-emitting subsystems that emit air in a generally continuous curtain 181 and 182 whose flows meet in a region proximal to 183 and join flows in an upward direction 184, thus forming a generally isolated region 185. The air emitted proximal to the ends of the conduit 172 at regions 178 and 177 may be aimed generally along the bed surface, and gradually aim more upwards along the conduit away from the ends 177 and 178. Such an arrangement can obviate the need for the subsystem 175, since the air aimed along the bed surface can be sufficient for particle isolation. The air delivery subsystem 172 may be rigid or flexible, and may lie on a bed or proximal to the edge of bed, such as supported off the edge of a bed.

In yet another embodiment, a ring (or arch) of air may be formed in proximity to a patient's face, with air moving upward to join and form an isolated region. In this manner, the materials required may be reduced as compared to the subsystem in FIGS. 29A and 29B, and the efficiency of isolation may be increased, and the amount of air may be reduced.

Figure 30:
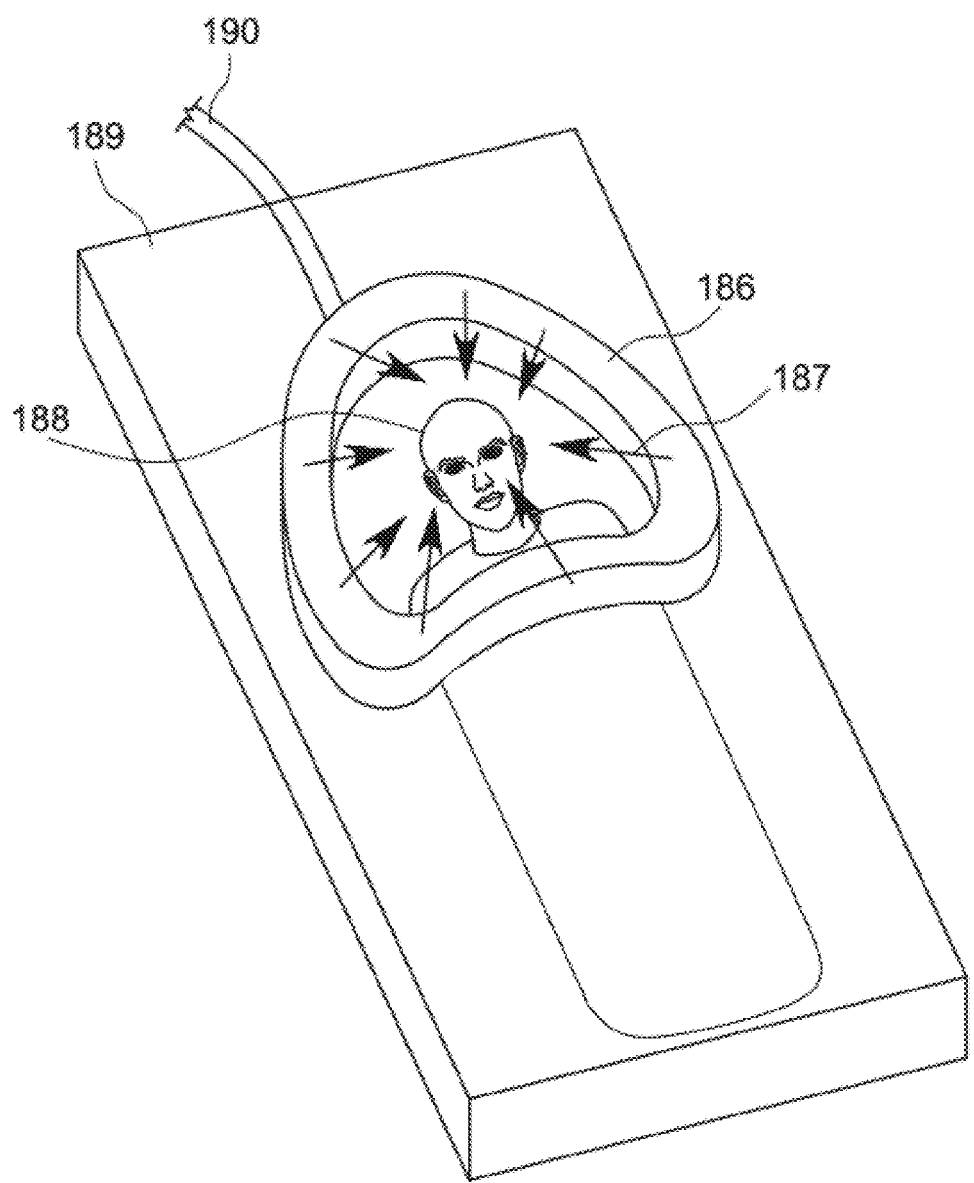
FIG. 30 shows a schematic of an example where an air-delivery subsystem, including an air conduit and air-directing subsystem, delivers an air curtain over a face and head of a patient on a bed, in accordance with some embodiments.

FIG. 30 shows a schematic of an example where an air-delivery subsystem 186 including an air conduit and air-directing subsystems, deliver an air curtain 187 over the face and head of a patient 188 on a bed 189. The air may be delivered to subsystem 186 by a conduit 190 from one or more devices that motivate air flow or an air-delivery source, such as a pump or a fan. The subsystem 186 may contain flexible regions so as to conform to a non-planar topology such as over the chest and pillow of a patient. The subsystem 186 may have subsystems to direct air in a desired direction, such as adjustable louvers, or a plurality of adjustable air direction subsystems. The air-directing subsystems may be coupled to light sources such as LEDs, or lasers that are generally aimed in a direction coincident with the air flow, so as to indicate the direction of air flow, where lasers may be low-powered Class I lasers (less than about 5 mW as used in laser pointers, or less than about 1 mW, or less than 0.5 mW, with lower power being less of a risk to eye damage). Laser color may be green which is the most sensitive color for the eye to see, so that a laser may be viewable at about 0.1 mW or about 0.25 mW or about 0.5 mW. Such a laser may have controls that limit the time the laser is on, such as an intermittent switch on a control panel generally inaccessible to a person (or patient) in a bed, or a switch that turns on when pressed and automatically turns off after a preset time, such as after about 1 second or about 5 seconds. The subsystem 186 in FIG. 30 can include of a plurality of air-delivery subsystems, forming segments. The air from such segments may be configured to form a generally contiguous dome of air over a patient. In some embodiments, an air segment is positioned on either side of a patient's head, with air directed as described herein in a set of directions so as to form a dome of air over the patient. In another embodiment, the subsystem 186 generally forms an arch that may sit around the head of a patient, the ends in proximity to the shoulders.

FIGS. 31A-31D show schematics of beds, with a person or patient and some examples of regions to which the systems described herein can couple to a bed, in accordance with some embodiments. The bed in these examples includes four sides comprising the head 202, the foot 204, a first side 206 extending from the head 202 to the foot 204, and a second side 208, opposite the first side 206, extending from the head 202 to the foot 204. The outlet or inlet can be coupled to the bed, for example, by mounting the outlet or inlet to the bed at the region, or by mounting the outlet or inlet to a base (or a wall, or another structure) and arranging the outlet or inlet in the proximity of the region (e.g., 210a or 212a).

Figure 31A:
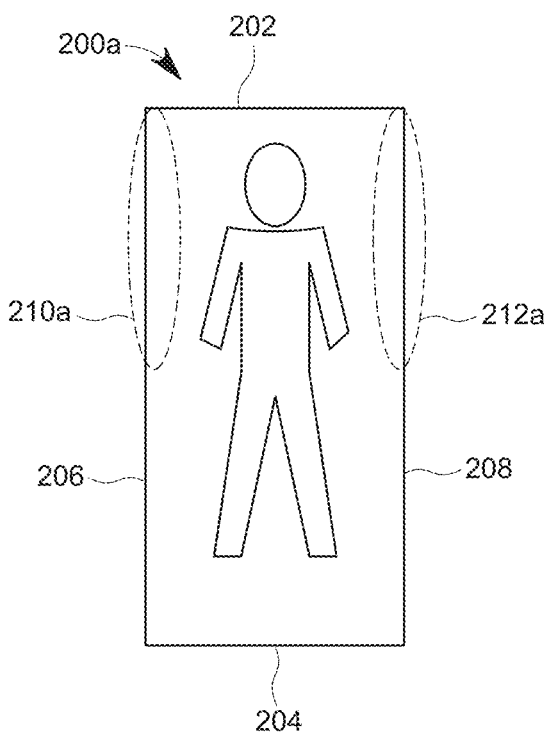
FIGS. 31A-31D show schematics of examples of regions to which the systems described herein can couple to a bed, in accordance with some embodiments.

FIG. 31A shows an example where a first outlet or inlet (e.g., an arch-shaped outlet or inlet like that shown in FIGS. 18-27) is coupled to a region 210a, and a second outlet or inlet (e.g., an arch-shaped outlet or inlet like that shown in FIGS. 18-27) is coupled to a region 212a. Region 210a is along a portion of side 206 of the bed, and region 212a is along a portion of side 208 of the bed, such that the outlet and inlet couple to the opposite sides 206 and 208 of the bed. The example in FIG. 31A is similar to that shown in FIG. 18, where the air flow of the air curtain moves across a person's body, and the air outlet and air inlet are located on the sides 206 and 208 of the bed. A portion of region 210a is between the head 202 and the foot 204 of the bed, and a portion of region 212a is between the head 202 and the foot 204 of the bed, in this example. Therefore, the outlet and inlet both couple to regions of the bed between the head 202 and the foot 204 of the bed.

Figure 31B:
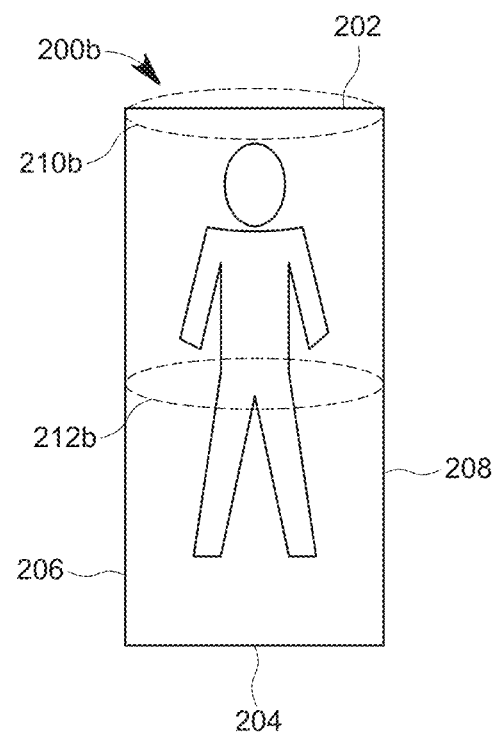

FIG. 31B shows an example where a first outlet or inlet (e.g., an arch-shaped outlet or inlet like that shown in FIGS. 18-27) is coupled to a region 210b, and a second outlet or inlet (e.g., an arch-shaped outlet or inlet like that shown in FIGS. 18-27) is coupled to a region 212b. The example in FIG. 31B is similar to that shown in FIG. 22. Region 210b is along the head 202 of the bed, and region 212b is at a location between the head 202 and the foot 204 of the bed. Region 212b is approximately at the waist of the person in FIG. 31B, but in other examples, region 212b can be at a location between the head 202 and the foot 204 of the bed, for example, approximately at the person's chest, or approximately at the person's knees. The second outlet or inlet couples to a location on the bed between the head 202 and the foot 2004 of the bed, in this example. For example, the second outlet or inlet can be arch-shaped, and the person's body can extend through the arch-shaped outlet or inlet.

Figure 31C:
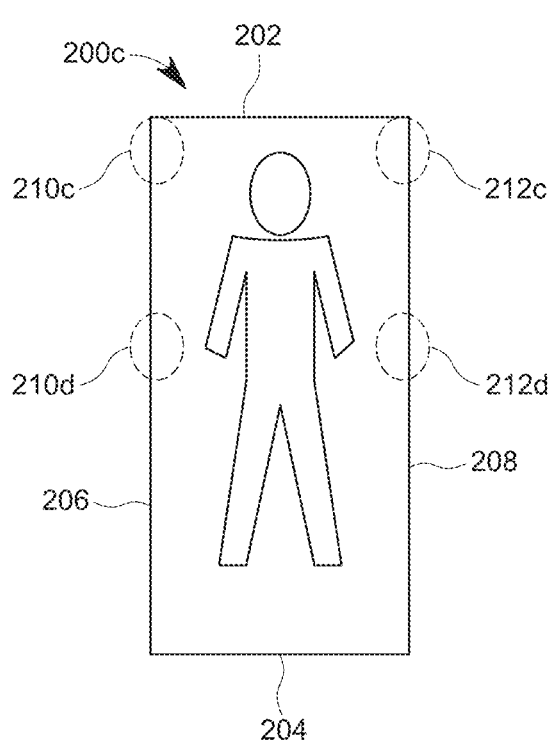
Figure 31D:
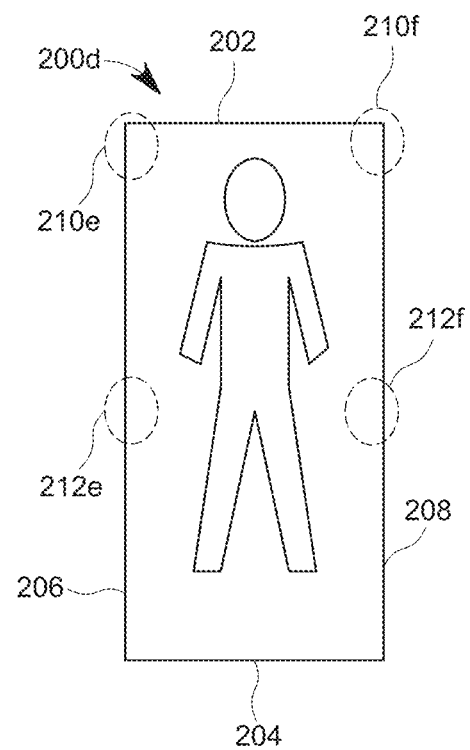

FIGS. 31C and 31D show examples where an arch-shaped air outlet is coupled to a bed in two regions, and an arch-shaped air inlet is coupled to the bed at two other regions. In these examples, the arch-shaped outlet or arch-shaped air inlet can be coupled to the bed, for example, by mounting the outlet or inlet to the bed, or by mounting the outlet or inlet to a base (or a wall, or another structure) and arranging the outlet or inlet in the proximity of the coupling regions (e.g., 210c and 210d, and 212c and 212d).

FIG. 31C shows an example where a first outlet or inlet (e.g., an arch-shaped outlet or inlet like that shown in FIGS. 18-27) is coupled to regions 210c and 210d, and a second outlet or inlet (e.g., an arch-shaped outlet or inlet like that shown in FIGS. 18-27) is coupled to regions 212c and 212d. Region 210c is at or near a corner of the bed where the head 202 and the side 206 meet, and region 210d is on the same side 206 between the head 202 and the foot 205 of the bed, such that the first outlet or inlet couples along a portion of the side 206 of the bed, along a portion of side 206 of the bed, and region 212*a* is along a portion of side 208 of the bed. Region 212*c* is at or near a corner of the bed where the head 202 and the side 208 meet, and region 212*d* is on the same side 208 between the head 202 and the foot 205 of the bed, such that the second outlet or inlet couples along a portion of the side 208 of the bed. The example in FIG. 31C is similar to that shown in FIG. 18, where the air flow of the air curtain moves across a person's body, and the air outlet and air inlet are located on the sides of the bed. Regions 212*e* and 212*f* are both between the head 202 and the foot 204 of the bed, in this example.

FIG. 31D shows an example where a first outlet or inlet (e.g., an arch-shaped outlet or inlet like that shown in FIGS. 18-27) is coupled to regions 210*e* and 210*f*, and a second outlet or inlet (e.g., an arch-shaped outlet or inlet like that shown in FIGS. 18-27) is coupled to regions 212*e* and 212*f*. The example in FIG. 31D is similar to that shown in FIG. 22. Region 210*e* is at or near a corner of the bed where the head 202 and the side 206 meet, and region 210*f* is at or near a corner of the bed where the head 202 and the side 208 meet, such that the first outlet or inlet is at or near the head 202 of the bed. Regions 212*e* and 212*f* are on the sides of the bed 206 and 208 respectively, between the head 202 and the foot 205 of the bed, such that the second outlet or inlet couples to a location on the bed between the head 202 and the foot 2004 of the bed. For example, the second outlet or inlet can be arch-shaped, and the person's body can extend through the arch-shaped outlet or inlet.

In some cases, an air curtain as described herein has substantially the same flow rate along the length of the air curtain. It may be generally advantageous for an air curtain as described herein to have generally the same flow rate along the length of the air curtain to improve the isolation efficiency of the air curtain. In other cases, it may be advantageous to have increased flow in one area, such as a section at the top of an arch for a patient that is coughing.

Figure 32A:
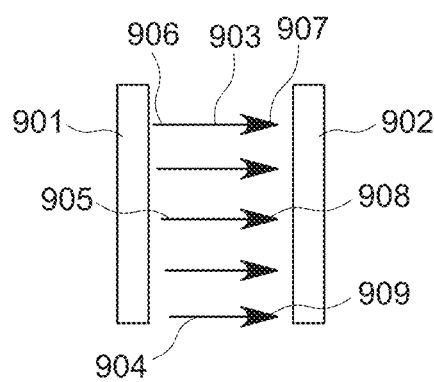
FIG. 32A shows a schematic of an example of an outlet and an air inlet, which can produce an air curtain, where the flow rates at points within the air curtain in close proximity to the air inlet and/or outlet are generally the same, in accordance with some embodiments.

FIG. 32A shows a schematic of an example of an outlet 901 (e.g., in the shape of an arch) and an air inlet 902, which can produce an air curtain 903, where the flow rates at points within the air curtain 903 along the air inlet 902 and/or outlet 901 are uniform, have a low amount of variation, or are substantially the same. In some cases, the flow rates at points within the air curtain 903 along the air inlet 902 and/or outlet 901 that are in close proximity to the air inlet 902 and/or outlet 901 are uniform, have a low amount of variation, or are substantially the same. In some cases, in close proximity to the air inlet and/or outlet may include distances approximately equal to dimensions of openings or ports of the inlets and outlets. In the example shown in FIG. 32A, flow rates 904, 905 and 906 at different positions in air curtain 903 that are in close proximity to the outlet 901 may be uniform, have a low amount of variation, or be substantially the same. Similarly, flow rates 907, 908 and 909 at different positions in air curtain 903 that are in close proximity to the inlet 902 may be uniform, have a low amount of variation, or be substantially the same. For example, a flow rate at 904 may have a velocity of 1 m/s and a volumetric flow rate of 100 cc/s per square centimeter, with a flow rate at 905 and 906 within 10% or 20% of these values. The flow rates 907, 908 and 909 in close proximity to the inlet may also be within 10%, or 20%, or 30% of one another, however, they may have significantly different values than those of the flows 904, 905 and 906 in close proximity to the outlet. In some cases, the air curtain (e.g., an arch-shaped air curtain) includes a plurality of flow rates in a vicinity of the air outlet and/or air inlet. In such cases, the respective air outlet and/or air inlet can be further configured to generate the air curtain such that the plurality of flow rates is within about 20% of one another along the respective arch-shaped air outlet and/or inlet.

To even out the flow through the conduits, inlets, outlets, and in the air curtain of the systems and methods described herein, air resistance subsystems may be included in the conduits, inlets, outlets of the systems and methods described herein to introduce resistance to the flow. For example, a subsystem could cause the resistance to increase, or decrease, or change in another way, along the length of a conduit, which can result in evening out the flow though the conduit, or of air exiting ports of the conduit at different locations along the conduit. In some cases, air may enter the conduits of the systems described herein at one or multiple points, and the pattern of resistance change along the conduit may be changed using the air resistance subsystems to create a desired outlet or inlet flow pattern depending on the placement and flows of the sources or sinks in the conduit. For example, the resistance may increase monotonically from one end to the other for flow introduced at one end, or alternately decrease from both ends towards the center (farthest from the ends) for a conduit configured as an air inlet with air being drawn out of both ends to enter the inlet conduits coupled to the air inlet.

FIGS. 32B-32I show different embodiments of air resistance subsystems that can be used to even out the flow through a conduit, to produce improved uniformity of outlets, inlets, and air curtains for the systems and methods described herein. The examples shown in FIGS. 32B-32I may show only one air source (for an outlet) or sink (for an inlet), but it is understood that in all embodiments a plurality of air sources and sinks for a single conduit shall be considered to be disclosed.

Figure 32B:
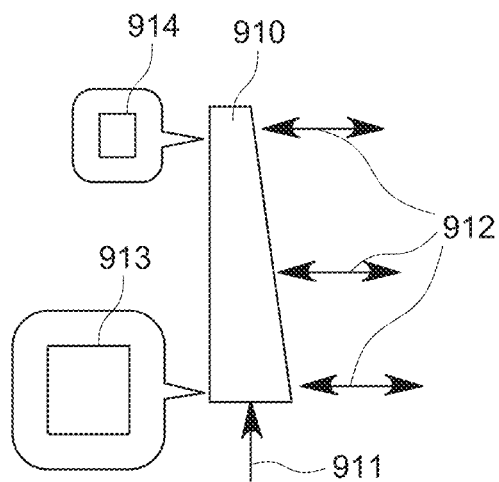
FIG. 32B shows a schematic of an example of an air conduit that may form an arch as disclosed herein, which has a non-uniform cross-section, in accordance with some embodiments.

FIG. 32B shows a schematic of an example of an air conduit 910 that may form an arch as disclosed herein, which has a non-uniform cross-section, in accordance with some embodiments. In this example, the air enters the conduit 910 generally an end of the conduit 910 to produce and air inlet or outlet with a flow of air 912 exiting conduit 910 at locations along the conduit 910. Air flow 912 can in some cases be approximately perpendicular to a direction along the length of conduit 910. The cross section 913 at one end of conduit 910 may be larger than a cross-section 914 at the opposite end. For air entering at end 911, the configuration will produce a flow 912 exiting at location along the conduit 910 that is more even or uniform than that of a conduit with a constant cross-section, as the resistance to flow of the conduit increases towards the distal end with the distal end closed (away from flow entrance). Not to be limited by theory, it is generally known that in a constant-cross-section conduit, with air outlets along its length, flow will be greater at the distal end (closed), thus increasing the resistance along the conduit will tend to increase flow at the proximal end and decrease it at the distal end. For flow exiting at an end of the conduit 911 (e.g., for an inlet instead of an outlet), the opposite is true, such that reducing the cross-section at the proximal end (compared to constant cross-section) and increasing it at the distal end, will tend to reduce the flow at the proximal end and increase it at the distal end, so as to create a more even flow from end to end. The drawing of conduit 910 is not drawn to scale, and the relationship of the change in cross section along the conduit, can be linear, exponential, quadratic, other power law, or other form in different embodiments.

Figure 32C:
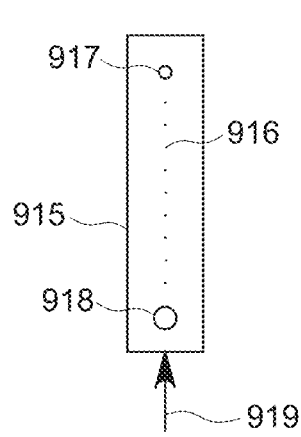
FIG. 32C shows a schematic of an example of a conduit with a port including openings for air inlet or outlet, in accordance with some embodiments.

FIG. 32C shows a schematic of an example of a conduit 915 with a port including openings 916, 917, and 918 for air inlet or outlet, in accordance with some embodiments. The dots and circles in FIG. 32C indicate a series of openings of the port including openings 916, 917, and 918, which make up a port of an inlet or an outlet. Openings 916, 917, and 918 have varying size along the length of the conduit 915 in this example, which can advantageously make flow of air into or out of the port more uniform along the length of the conduit 915. Opening 917 is towards one end of the conduit 915 and is smaller in area than opening 918 at the opposite end of the conduit, with openings in between generally smoothly and or monotonically varying in size between them. The current example shows an outlet where air is supplied at 919, and exits the ports though openings 916, 917, and 918. Alternatively, as described above with respect to the conduit with a varying cross-section, the conduit 915 can be configured as an air inlet (draws air in) with 919 drawing air at one end. In such cases, the opening 918 would be smaller in area compared to the opening 917 to effect a more even inlet flow along the conduit 915. The openings 917 and 918 are round in FIG. 32C, but openings of ports of the systems and methods described herein can have other cross-section shapes, such as rectangles, squares, honeycomb, or slots or form a continuous port such as a slot running the length of the conduit. In the case of a continuous slot, the width of the slot could be varied along the length of the conduit.

Figure 32D:
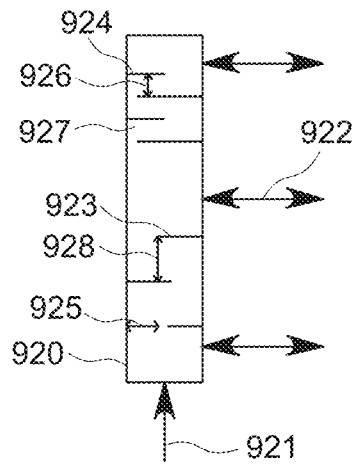
FIG. 32D shows a schematic of an example of a conduit where an air resistance change along the conduit is created by a series of baffles, in accordance with some embodiments.

FIG. 32D shows a schematic of an example of a conduit where an air resistance change along the conduit is created by a series of baffles, in accordance with some embodiments. In this example, a series of baffles 923 and 924 are arranged inside or internal to the conduit 920. Conduit 920 has an air source or sink 921, with an air inflow or outflow 922 along the length of the conduit 920. The baffles 923 and 924 are structures that protrude from walls of the conduit that create a resistance to flow. When multiple baffles 923 and 924 are used together, the resistance along the conduit 920 can be changed to make the air flow 922 along conduit 920 more uniform. For example, baffles 923 and 924 are generally flat surfaces in contact with the walls of the conduit that partially fill the cross-section of the conduit, and are offset from each other so as to create a tortuous path for the air flow, thus creating resistance to flow. The resistance is dependent upon the spacing of the baffles 923 and 924 with inter-baffle spacing 926 and 928, and baffle-wall opening spacings 925 and 927.

FIG. 32D shows a schematic of an example of a conduit 929 in cross-section with a baffle region 930 and an open region 931, in accordance with some embodiments. Flow resistance increases with decreasing inter-baffle spacing and baffle-wall spacing. In the example illustrated, two sets of baffles 923 and 924 have different resistances. There may be multiple baffles continuously along the conduit with generally monotonically varying spacings in order to create a generally monotonically varying flow resistance. Baffles may be of other shapes such as curved or scooped or generally cylindrical. Generally cylindrical baffles may be disposed to create Karman vortices which may create resistance to flow.

Figure 32E:
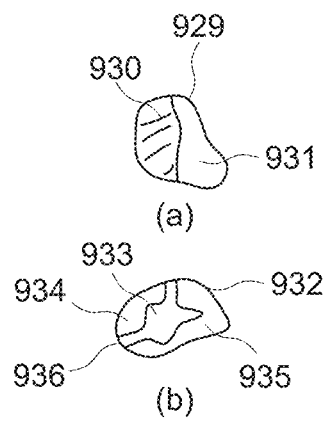
FIG. 32E shows a schematic of an example where baffles are in contact with the walls of a conduit along a part or sections of their perimeters, in accordance with some embodiments.

FIG. 32E shows a schematic of an example where baffles 933 are in contact with the walls of a conduit 932 along a part or sections of their perimeters, in accordance with some embodiments. In this example, the baffle 933 is a disk suspended within a conduit. Conduit 932 of non-specific shape has a baffle 933 generally separated from the conduit walls creating unobstructed spaces 934 and 935. The baffle 933 is coupled to the wall of the conduit 932, using two supports 936. In other cases, one or multiple supports or contacts points can be used.

In yet another embodiment, resistance to flow may be created by filters at the ports or openings of the conduits of the systems described herein, for example systems comprising arch-shaped air inlets and outlets. The filters can have varying air resistance, for example, by being made of a porous material with varying density. In one case such a material may be a foam with varying pore size. In another case, fiber or textile filters can have varying resistance to air flow by using more or fewer fibers per area, having a different thickness, and/or by changing the fiber diameters. In another example, the filters can be made of a porous mixture of filler particles in a housing, and the air resistance through the housing can be varying by varying the sizes of the housing and filler particles.

Figure 32F:
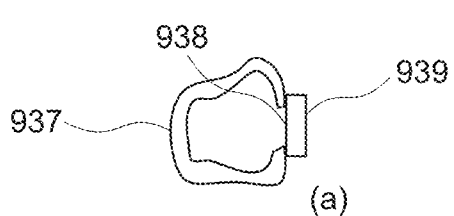
FIG. 32F shows a schematic of an example of a cross-section of a conduit an air inlet or outlet port, that is covered or substantially sealed with a filter, in accordance with some embodiments.

FIG. 32F shows a schematic of an example of a cross-section of a conduit 937 an air inlet or outlet port 938, that is covered or substantially sealed with a filter 939, in accordance with some embodiments.

Figure 32G:
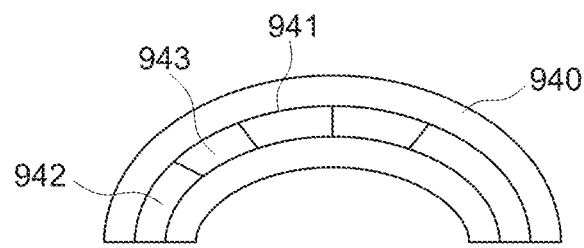
FIG. 32G shows a schematic of an example of a face of an inlet or outlet port of a conduit, with a region of filter, in accordance with some embodiments.

FIG. 32G shows a schematic of an example of a face (inlet of outlet port) of a conduit 940, with a region of filter 941, in accordance with some embodiments. The filter 941 may be generally continuous, or may cover generally all of the ports which may have individual openings or have a continuous opening, where the filter 941 may change along the length of the conduit 940, as described above to create a change in resistance. The resistance of the filter 941 can change generally monotonically along the conduit. Filter 941 may have a generally continuous or monotonic change in resistance to flow along the length of the conduit, such as by a change in thickness of a material within filter 941. In some cases, there may be a plurality of regions such as filter 942 and filter 943 wherein each region has a filter with a different resistance.

In yet another embodiment, resistance to flow may be created by adjustable openings at the ports of a conduit or arch. For example, the adjustable opening may be a valve, or a louver.

Figure 32H:
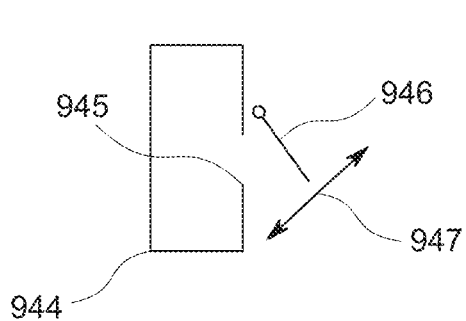
FIG. 32H shows a schematic of an example of an adjustable opening for an outlet or an inlet port that has a louver, in accordance with some embodiments.

FIG. 32H shows a schematic of an example of an adjustable opening for an outlet or an inlet port that has a louver, in accordance with some embodiments. A cross-section of conduit 944 is shown with a port 945, and a louver 946. The louver 946 may be adjusted over a range of positions 947 indicated by the arrow in the figure. The louver 946 may be manually adjusted or can be adjustable using an actuator subsystem that can be controlled by a controller or processor of the system.

Figure 32I:
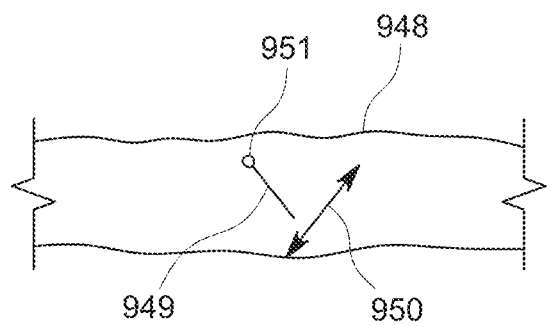
FIG. 32I shows a schematic of an example where the flow within a conduit may be adjusted by dampers disposed internal to the conduit, in accordance with some embodiments.

FIG. 32I shows a schematic of an example where the flow within a conduit may be adjusted by dampers disposed internal to the conduit, in accordance with some embodiments. A section of a conduit 948 is shown with a flap 949 that may be rotated about an axis 951 with a range of positions 950 indicated by the arrow in the figure. The flap 949 forms a damper which creates a variable resistance to air flow within the conduit 948. The conduit 948 may have a plurality of dampers within it, and can be adjusted such that the positions change continuously or monotonically along the length of the conduit 948. As described above, the variable resistance along the length of the conduit 948 can be beneficial to flow exiting the conduit 948 at openings along the conduit 948. The dampers may be manually adjusted or by an actuator subsystem that can be controlled by a controller in the system.

In some embodiments, it may be desirable to create uniform flow across the length of the conduit which may afford uniform air curtain isolation efficiency (e.g., to isolate particulates within a region, or to isolate a region from particulates). In some cases, however, it may be desirable to have non-uniform flow across the air curtains of the systems and methods described herein, where the air curtain has regions of higher and lower flow. For example, certain regions of a space may be subject to a greater influx of particulates, or a greater speed of particulates than other regions of an air curtain in some applications. An example may be in isolating a patient on a bed that is sneezing or coughing, which may generally eject particulates upwards away from the bed, and generally more than towards the edges of the bed. In such a case, it may be effective to create higher flow over the patient to increase efficiency of capturing the ejected particles, instead of creating higher flow over the whole arch. Reducing the flow of the air curtain in certain regions can be beneficial, for example, to conserve power, and improve the efficiency of the whole system. Efficiency can be an important consideration, for example, since some systems have constrained power budgets, such as the power available from a 110V AC 1500 W wall socket.

Described in this application is a system for creating a curtain of air with a subsystem of arched conduits (simply referred to as an arch) for delivering and in some cases receiving a flow of air. Herein is disclosed subsystems and structures for arches that are inflatable.

It is desirable to have arches in the air isolation system that have the following characteristics. First, the arches may be disposable. Second, the arches may move out of the way of clinicians. To accomplish this, subsystems are disclosed that support an arch that is inflatable, and deflatable (that is, an arch that has been inflated, may have the air inside generally removed so that the arch deflates).

Figure 33A:
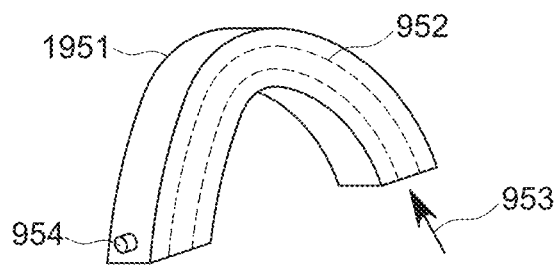
FIG. 33A shows a schematic example wherein an arch has an opening connected to an air supply conduit and a region on a surface of the arch that is an air outlet including ports or nozzles that are a source of air, in accordance with some embodiments.

FIG. 33A shows a schematic example wherein an arch 1951 has an opening connected to an air supply conduit 953 and a region on a surface of the arch that is an air outlet 952 including ports or nozzles that are a source of air, in accordance with some embodiments. The arch 1951 may inflate due to the higher pressure inside the arch conduit than in the atmosphere around the arch 1951. In some cases, a separate vent 954 is also included, which can be used to inflate a separately inflatable section of the arch 1951, for example, using a fan, a pump, or a pressurized air tank.

The arch 1951 may be coupled via a plurality of conduits to air sources and air sinks and air vents. To deflate the arch 1951, an air source may be turned off, such that air escapes from the air outlet 952 until pressure equalizes. Additionally, one or more manually or electromechanically operated vents 954 may be part of the arch 1951 to allow for deflation.

In another embodiment, the arch may be deflated by reversing the flow in a plurality of conduits that were sources of air for inflation, such that these conduits then suck air such as via a fan that is reversed in rotation so that the arch deflates more rapidly than by only turning off the source air.

In another embodiment, an arch may have separately inflatable subsystems to provide mechanical support.

Figure 33B:
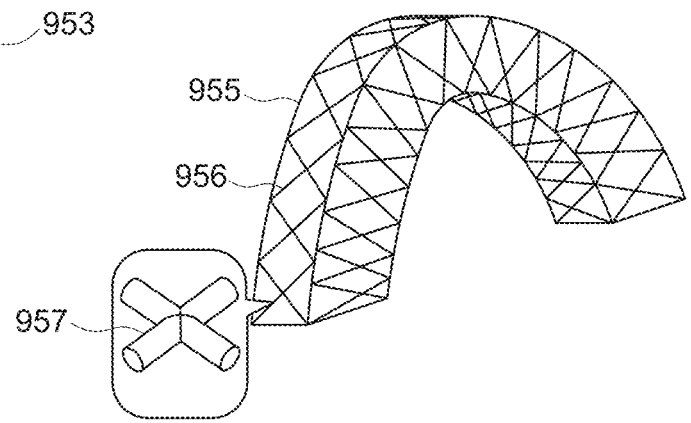
FIG. 33B shows a schematic example of an arch with conduits connected to the arch that are separately inflatable by an air source subsystem, in accordance with some embodiments.
Figure 33C:
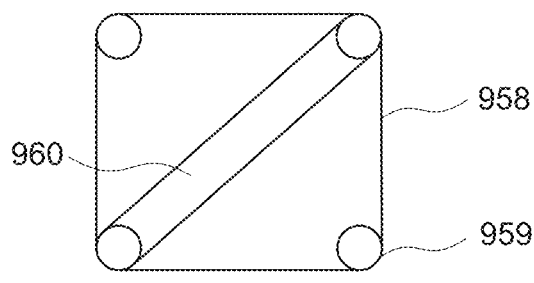
FIG. 33C shows a schematic example where a conduit viewed in cross-section has support conduits along its length, as well as supports internal to the arch conduit, in accordance with some embodiments.

FIG. 33B shows a schematic example of an arch 955 with conduits 956 connected to the arch that are separately inflatable by an air source subsystem, in accordance with some embodiments. For example, the air source subsystem can include a fan, a pump, or a pressurized air tank, that is different than the air source subsystem which provides air to the air curtain. The additional conduits 956, which can also be referred to as supports, may form a structure that gives mechanical stability to the arch, whether the arch is an inlet or outlet. While such supports may not be needed to inflate an air outlet arch as described above and illustrated in FIG. 33A, an air inlet arch will generally have a lower pressure inside the conduit than the atmosphere, thus requiring an additional structure to support it during operation. An example of such a support structure is shown in FIG. 33B, where a system of conduits 957 form a truss structure. The support pattern is not limited by that shown in FIG. 33B, but may be any pattern that provides sufficient strength to maintain the arch in an inflated state during operation, especially when the arch is an inlet drawing air into the arch. In another embodiment, the support conduits may be internal to the arch conduit. FIG. 33C shows a schematic example where a conduit 958 viewed in cross-section has support conduits 959 along its length, as well as supports 960 internal to the arch conduit.

The materials of the inflatable conduits disclosed herein may generally be flexible membranes, such as polyurethane sheets, or other plastic sheet material. The material may be transparent, opaque, translucent, or have a color.

Rigid components may also be incorporated into the inflatable arches, such as conduit connectors, air nozzles, vents, and mechanical supports. Such mechanical components may or may not be mechanically coupled to each other. In some cases, the rigid mechanical components, if included, are not coupled to form a rigid structure, which would prevent the arch from fully collapsing.

The supports of the inflatable arches and conduits described herein may themselves be conduits, such as tubes, or other air-containing structures. In some cases, the arch may have an outer support structure comprising two layers of flexible materials intermittently joined together.

Figure 33D:
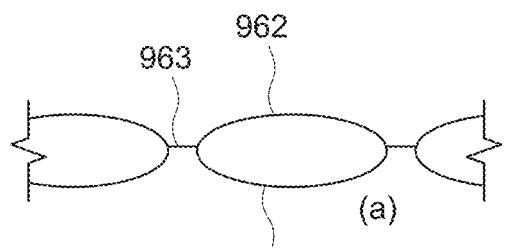
FIG. 33D shows a schematic of an example of a material of an arch or other inlet or outlet described herein, in accordance with some embodiments.
Figure 33D:
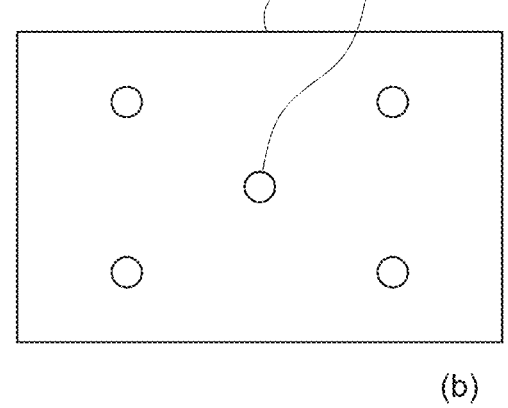

FIG. 33D shows a schematic of an example of a material of an arch or other inlet or outlet described herein, in accordance with some embodiments. View (a) shows the material in cross-section, and view (b) shows the material from a side view, where layers of flexible material 962 are mechanically joined at multiple positions such as 963.

The air support system of the inflatable components described herein may have a separate air supply such as a plurality of fans or pumps, connected via air conduits to the supports, the generate a pressure inside the supports greater than atmospheric pressure. In some cases, the pressure inside the supports is sufficiently high to overcome the force of suction on an air inlet arch in order to maintain the air outlet arch in an inflated state. This air supply may also be configured as an air sink in order to deflate the arch.

FIGS. 34A-34D show schematic examples of outlets and inlets forming an air curtain using air-directing subsystems, in accordance with some embodiments.

Figure 34A:
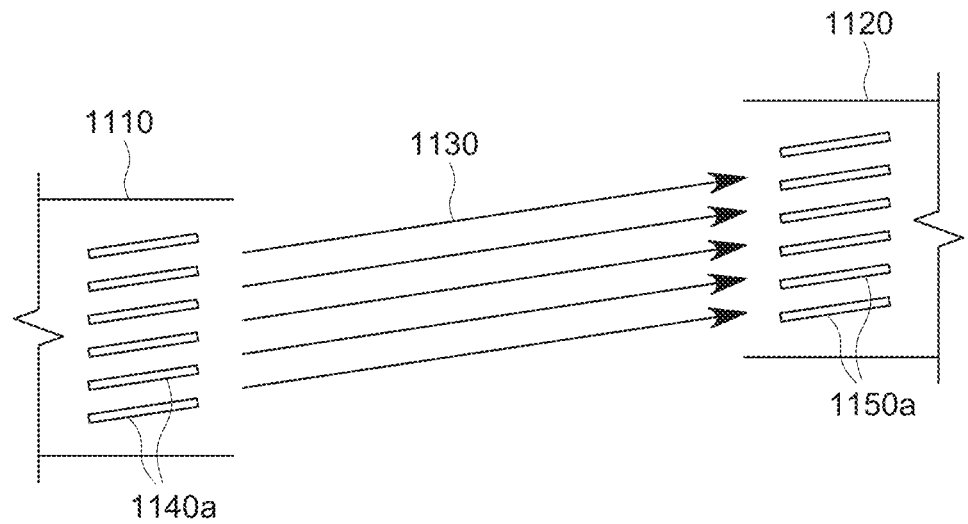
FIGS. 34A-34D show schematic examples of outlets and inlets forming an air curtain using air-directing subsystems, in accordance with some embodiments.
Figure 34B:
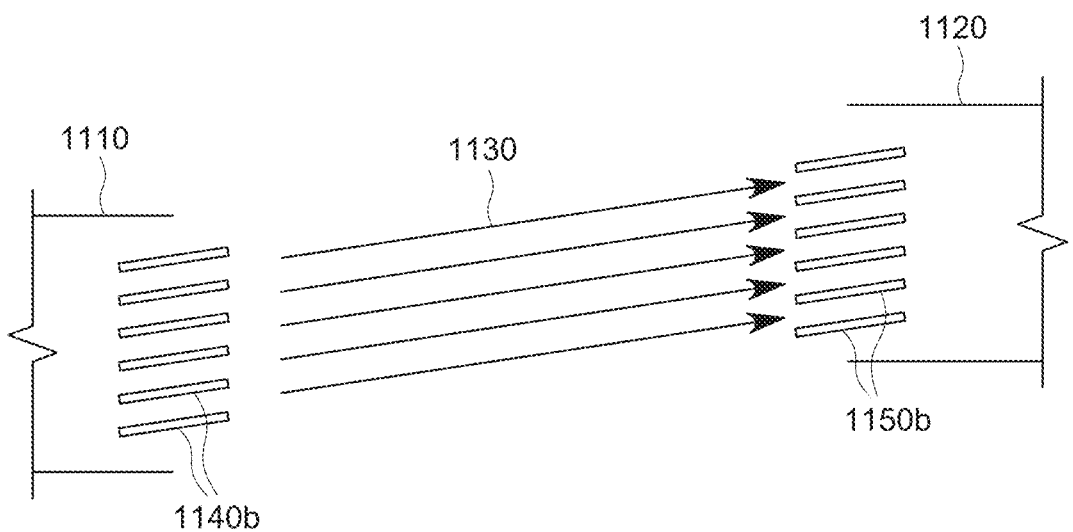

FIGS. 34A and 34B show examples where outlet 1110 and inlet 1120 are used to form air curtain 1130 using air-directing subsystems that are louvers 1140*a*, 1140*b*, 1150*a*, and 1150*b*. FIG. 34A shows an example where the louvers 1140*a* and 1150*a* are inside the outlet 1110 and inlet 1120 respectively. FIG. 34B shows an example where the louvers 1140*b* and 1150*b* extend outside of the outlet 1110 and inlet 1120 respectively. Louvers 1140*a*, 1140*b*, 1150*a*, and 1150*b* can be movable, and can be manually movable, or can be moved using an electromechanical actuation system (not shown).

Figure 34C:
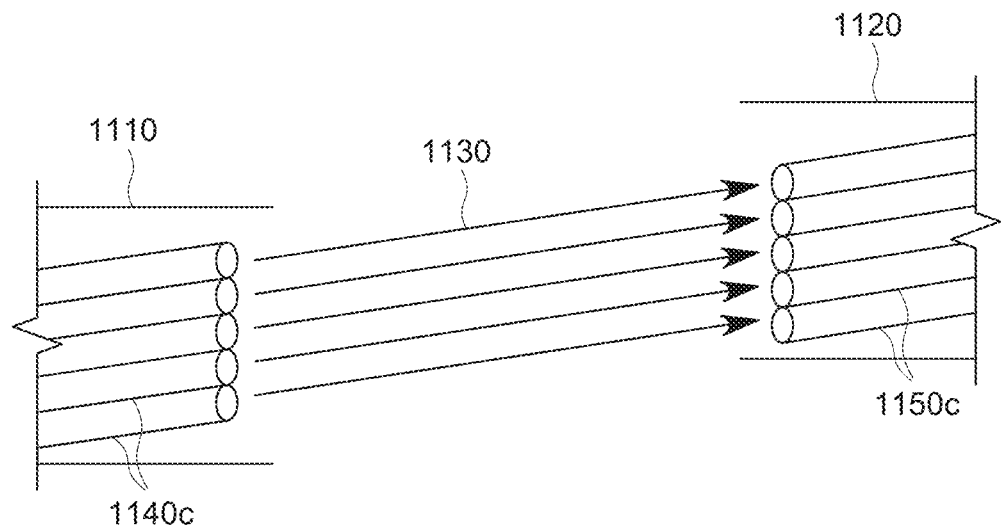
Figure 34D:
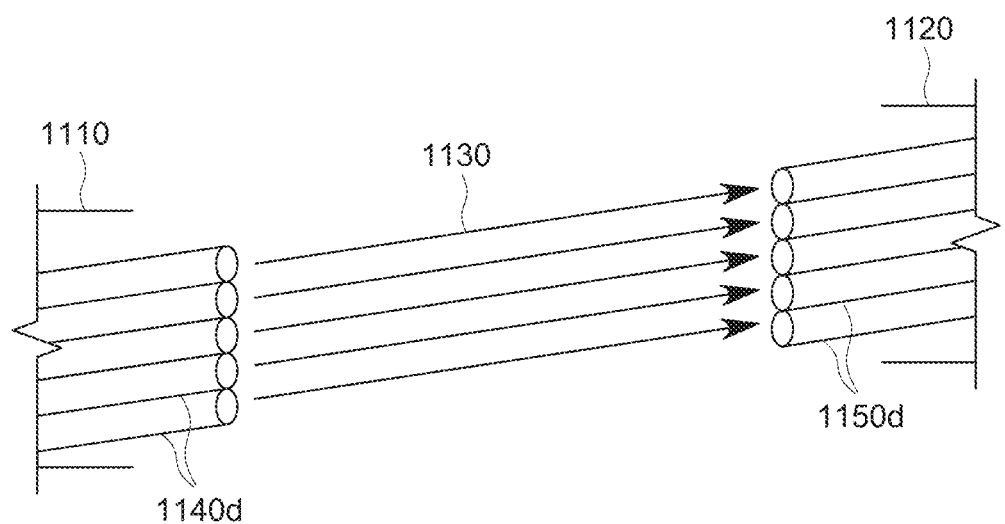

FIGS. 34C and 34D show examples where outlet 1110 and inlet 1120 are used to form air curtain 1130 using air-directing subsystems that are movable tubes or conduits 1140*c*, 1140*d*, 1150*c*, and 1150*d*. FIG. 35A shows an example where the moveable tubes or conduits 1140*c* and 1150*c* are inside the outlet 1110 and inlet 1120 respectively. FIG. 35B shows an example where the movable tubes or conduits 1140*d* and 1150*d* extend outside of the outlet 1110 and inlet 1120 respectively. Moveable tubes or conduits 1140*c*, 1140*d*, 1150*c*, and 1150*d* can be manually movable, or can be moved using an electromechanical actuation system (not shown). The movable tubes or conduits 1140*c*, 1140*d*, 1150*c*, and 1150*d* can have circular or oval cross-sections, or can have square, rectangular, hexagonal, or other shaped cross-sections. In some cases, the movable tubes or conduits 1140*c*, 1140*d*, 1150*c*, and 1150*d* can be arranged in an array. For example, an array of tubes with hexagonal cross-sections can form a honeycomb structure, which can be movable to direct air flow out of the port of an outlet or into the port of an inlet.

Figure 35:
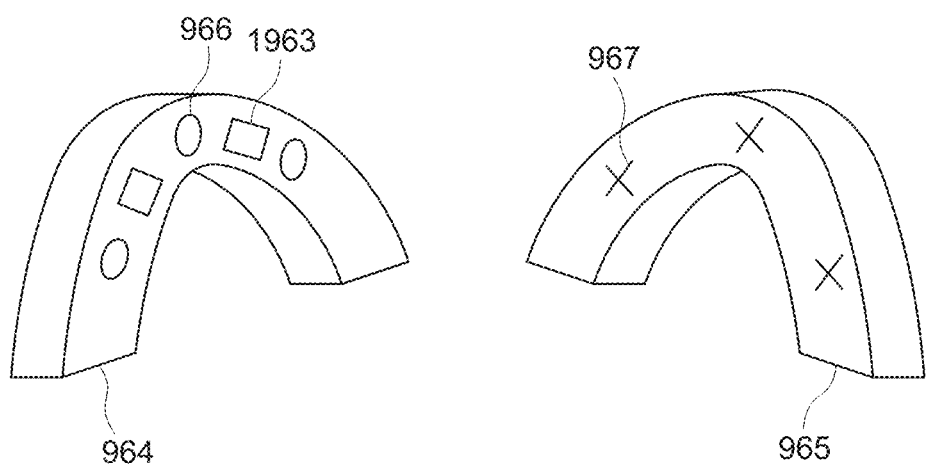
FIG. 35 shows a schematic example of a subsystem for ensuring alignment of two arch-shaped air inlets/outlets, in accordance with some embodiments.

FIG. 35 shows a schematic example of a subsystem for ensuring alignment of two arch-shaped air inlets/outlets, in accordance with some embodiments. An arch-shaped outlet or inlet 964 and an arch-shaped inlet or outlet 965 have subsystems that together can have an output that is indicative of relative positions. For example, arch-shaped outlet or inlet 964 can include an optical source 966 such as a laser, an LED, or a camera, shown by a plurality of circles. Arch-shaped outlet or inlet 964 can also include a sensor 1963 may be a sensor to detect light, such as a split sensor, or a CMOS sensor, indicated by the squares of which there may be a plurality. Arch-shaped inlet or outlet 965 may have subsystems 967 which may be reflectors such as retroreflectors, or fiducial marks. Each arch may have a combination of all of the aforementioned, which can be used to align and/or adjust a position of the arch-shaped outlet or inlet 964 and the arch-shaped inlet or outlet 965. For example, the optical source 966 can shine light which is reflected by the subsystems 967 and detected by sensor 1963 to determine if the arch-shaped outlet or inlet 964 and the arch-shaped inlet or outlet 965 are aligned. In another example, the optical source 966 can be a camera which images the subsystems 967 which are fiducial marks to determine if the arch-shaped outlet or inlet 964 and the arch-shaped inlet or outlet 965 are aligned. In some cases, the arch-shaped outlet or inlet 964 and the arch-shaped inlet or outlet 965 can be manually aligned using the optical source 966, sensors 1963, and subsystems 967. In some cases, the arch-shaped outlet or inlet 964 and the arch-shaped inlet or outlet 965 can be mounted to electromechanical systems to automatically align the arch-shaped outlet or inlet 964 and the arch-shaped inlet or outlet 965 based on the feedback from the optical source 966, sensors 1963, and subsystems 967.

FIGS. 36A-36D show schematics of examples, where an outlet and an inlet are mounted, for example to couple to a bed, and the outlet and/or inlet can be moved, in accordance with some embodiments. In these figures, arch-shaped air outlet 1220*a* and arch-shaped air inlet 1220*b* are coupled to a bed 1210, using a mounting system. In other cases, the flow direction can be reversed and arch-shaped air outlet 1220*a* can be an inlet and arch-shaped air inlet 1220*b* can be an outlet. The mounting system includes a base 1240 and supports 1250*a* and 1250*b*. In other cases, the mounting system can include elements to couple the arch-shaped air outlet 1220*a* and arch-shaped air inlet 1220*b* to the bed, for example, by coupling the supports 1250*a* and 1250*b* to a frame of the bed. FIGS. 36A-36D each only show the movement of the arch-shaped air inlet 1220*b* for clarity, but the arch-shaped air outlet 1220*a*, can also move in some cases. Such movement can be advantageous for access to the bed 1210 or a person on the bed, or for a person on the bed 1210 to more easily get out of the bed.

Figure 36A:
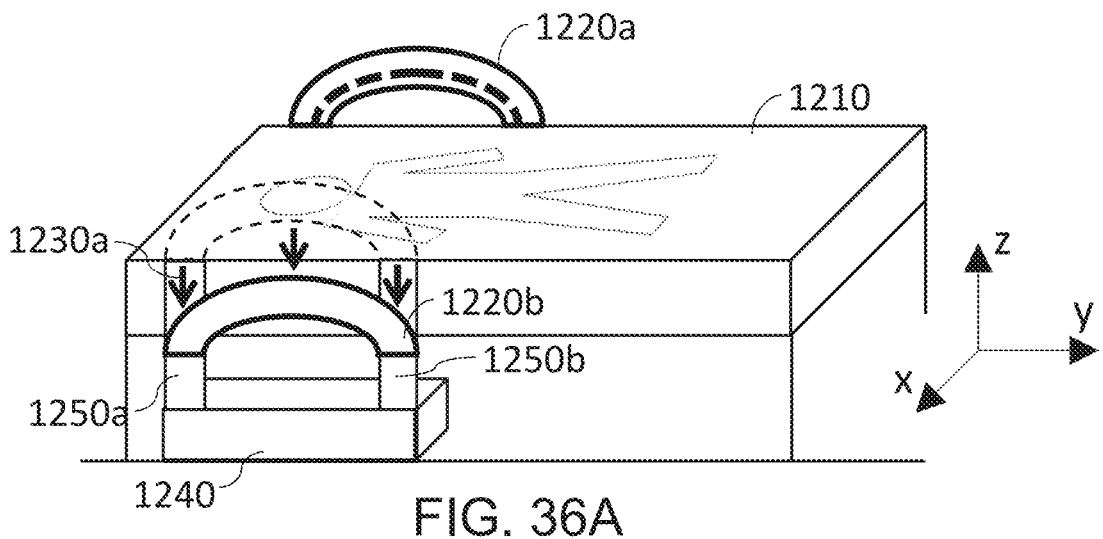
FIGS. 36A-36D show schematics of examples, where an outlet and an inlet are mounted, for example to couple to a bed, and the outlet and/or can be moved, in accordance with some embodiments.

FIG. 36A shows an example where the mounting system is configured such that the arch-shaped air outlet 1220*a* and/or arch-shaped air inlet 1220*b* retracts below the surface of the bed (like the movement shown by arrows 1230*a*). For example, the supports 1250*a* and/or 1250*b* of the mounting system could include guiding elements (e.g., rails, or tracks, or linear gears, or screws, or any linear movement mechanism), and the arch-shaped air outlet 1220*a* and/or arch-shaped air inlet 1220*b* could be moveably coupled to the guiding elements, for example, using one or more mating elements (e.g., protruding tabs, rails, wheels, and/or gears) that are guided by the guiding elements. Additionally, in some cases, the mounting system can include supports and guiding elements to allow the arch-shaped air outlet 1220*a* and/or arch-shaped air inlet 1220*b* to translate horizontally or slide in the y-direction and/or in the x-direction.

Figure 36B:
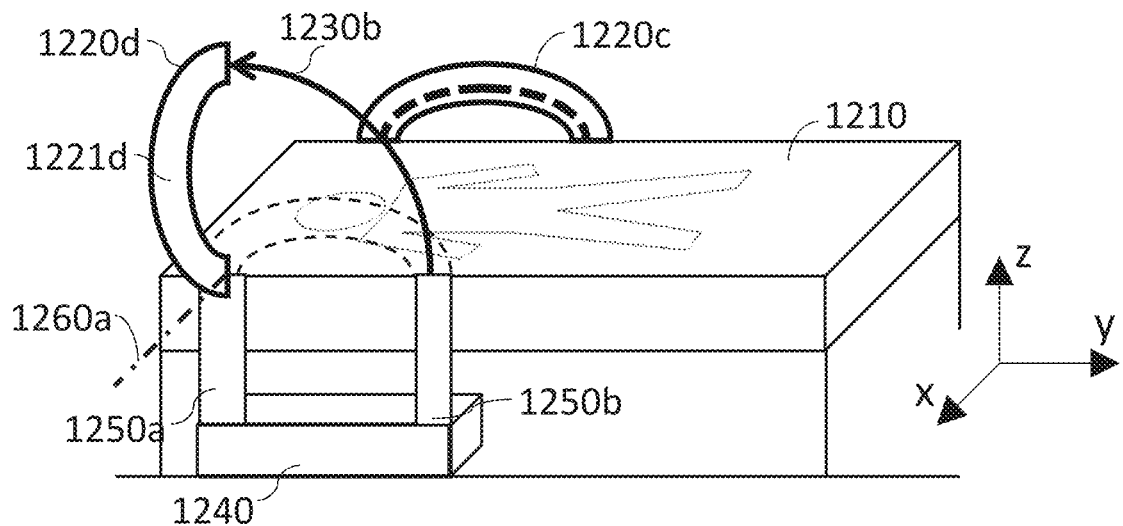
Figure 36C:
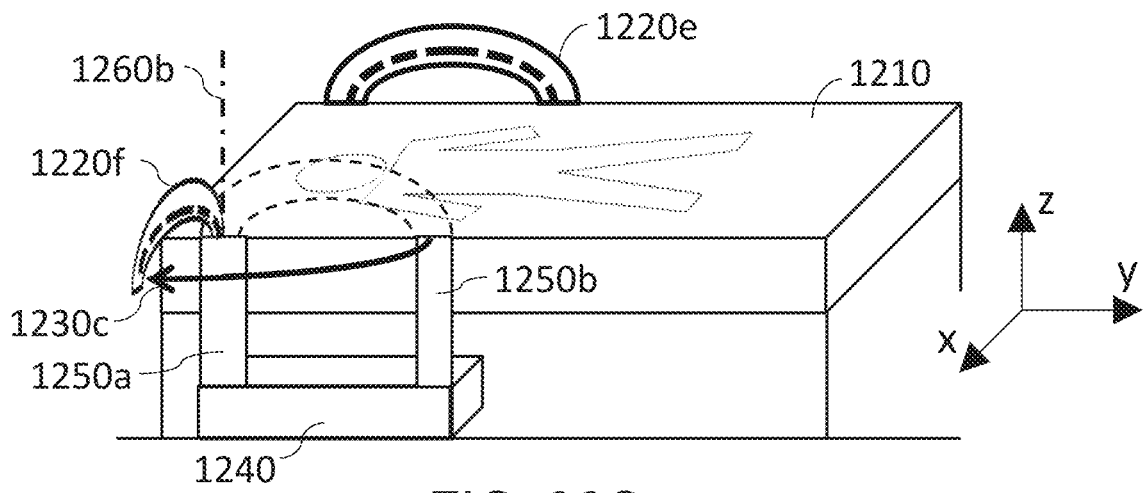
Figure 36D:
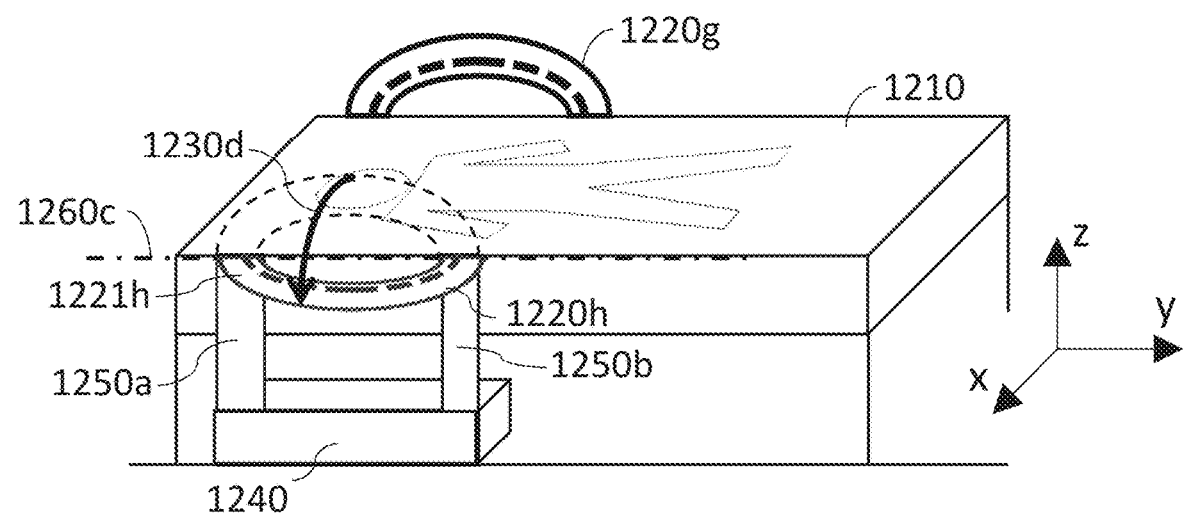

FIGS. 36B-36D show examples where the mounting system is configured such that the arch-shaped air outlet 1220*a* and/or arch-shaped air inlet 1220*b* can rotate with respect to the bed. For example, supports 1250*a* and/or 1250*b* could include one or more rotation elements (e.g., a hinge, a pivot, a swivel joint, a slotted ball joint, a universal ball joint, or any rotating movement mechanism) coupled to the arch-shaped air outlet 1220*a* and/or arch-shaped air inlet 1220*b* to enable them to rotate with respect to the bed.

FIG. 36B shows an example where the arch-shaped air outlet 1220*a* and/or arch-shaped air inlet 1220*b* could rotate along a horizontal rotation axis 1260*a* perpendicular to a major surface 1221*d* of the arch (in the x-direction as shown in FIG. 36B) and rotate orientation so that one side moves up away from the bed (like motion 1230*b* shown in FIG. 36B).

FIG. 36C shows an example where the arch-shaped air outlet 1220*a* and/or arch-shaped air inlet 1220*b* could rotate along a vertical rotation axis 1260*b* (in the z-direction as shown in FIG. 36C) and one side of the arch-shaped air outlet 1220*a* and/or arch-shaped air inlet 1220*b* can swing out from the edge of the bed (like motion 1230*c* shown in FIG. 36C).

FIG. 36D shows an example where the arch-shaped air outlet 1220*a* and/or arch-shaped air inlet 1220*b* could rotate along a horizontal rotation axis 1260*c* parallel to a major surface 1221*h* of the arch (in the y-direction as shown in FIG. 36C) and the top of the arch-shaped air outlet 1220*a* and/or arch-shaped air inlet 1220*b* can fold down from the edge of the bed (like motion 1230*d* shown in FIG. 36D).

Figure 37:
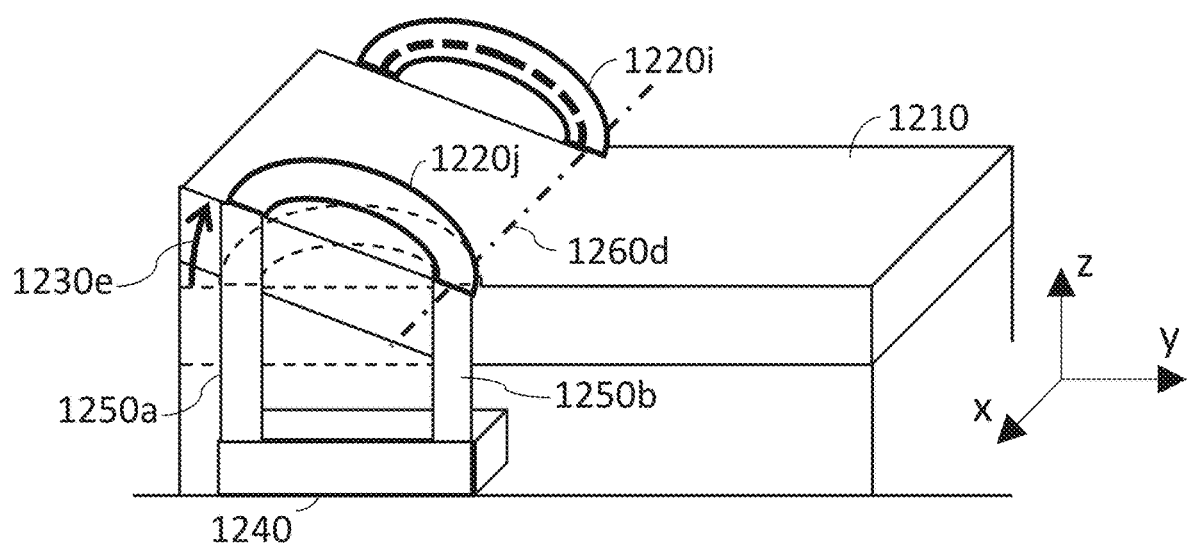
FIG. 37 shows a schematic of an example where the air outlets and/or air inlets of the systems described herein are movable such their positions with respect to a bed is maintained, even when the bed itself is movable, in accordance with some embodiments.

FIG. 37 shows a schematic of an example where the air outlets and/or air inlets of the systems described herein are movable such their positions with respect to a bed 1210 is maintained, even when the bed 1210 itself is movable, in accordance with some embodiments. The example in FIG. 37 includes a similar mounting system as the systems shown in FIGS. 36A-36D. The mounting system in this example is configured to couple the outlet and inlet to a bed 1210 that is adjustable or moveable in this example. The adjustable bed 1210 in this example can recline, by approximately half of the bed rotating along an axis or rotation 1260*d* that is horizontal and across the bed (in the x-direction as shown in FIG. 37). Direction 1230*e* shows the movement of the bed 1210 and the movement of the arch-shaped air outlet 1220*i* and the arch-shaped air inlet 1220*j*. Since the bed 1210 and the arch-shaped air outlet 1220*i* and the arch-shaped air inlet 1220*j* move with the bed when the bed is adjusted, the air curtain generated by the arch-shaped air outlet 1220*i* and the arch-shaped air inlet 1220*j* also moves with the bed when the bed is adjusted. In some cases, the arch-shaped air outlet and the arch-shaped air inlet maintain relative positions to each other when moving with the bed.

The mounting system in the system shown in FIG. 37 includes a base 1240 and supports 1250*a* and 1250*b* in this example. In other cases, the mounting system can be mounted to another object such as a wall, or a table, or the bed to which the system is coupled. The supports 1250a and 1250b can move the arches with the bed 1210 as the bed moves such that both arches may rotate. In some cases, both arches remain upright with respect to the bed, and remain in the same position relative to each other. In this case, the arch-shaped air outlet 1220i and/or arch-shaped air inlet 1220j can rotate along a horizontal rotation axis 1260d perpendicular to a major surface of the arch (in the x-direction as shown in FIG. 37) and rotate orientation so that one side moves up with the bed 1210 as it moves. In some embodiments, the supports 1250a and 1250b are configured to move the arch-shaped air outlet 1220i and/or arch-shaped air inlet 1220j in other directions, for example translating them up or down (in the positive or negative z-direction in the figure), as needed to move them with an adjustable bed 1210 as it moves.

The air curtain generating systems and methods described herein can include one or more air-delivery subsystems that have a plurality of segments that are mechanically connected so that the relation of one segment to the next is flexible or adjustable while the segments form a generally contiguous conduit. Segments of the air-delivery systems may contain adjustable air-directing subsystems such as louvers. In other cases, the air direction from a segment may be fixed and the segment itself can be fixedly adjustable, so the generally complete segment may be positioned to adjust the direction of airflow. wherein some cases, the segment has a subsystem that allows the segment to generally be fixed in position after repositioning. This may improve the efficiency of the air delivery, including sound minimization, as the air conduit and air-aiming subsystem may be optimized prior to construction, and generally never adjusted so as to achieve improved performance.

The air curtain generating systems and methods described herein can include one or more subsystems that can detect light, such as a camera or a plurality of photo sensors. In such systems, light can be emitted by a subsystem (e.g., made visible by the emission of harmless particulates), and the light is detected and imaged to determine a pattern. The position of the light and the pattern can be used to indicate the position of the air curtain. In some cases, control systems can use information from such light sensors to further to indicate to an operator the position of the air curtain, or to indicate to an automation subsystem that can control the air-direction subsystems to create a pre-desired outcome such as a height or volume of an isolation region. In some cases, the systems and methods described herein can further include the use of one or more electromechanical systems (e.g., controlled by a processor, and including sensors) to automatically adjust the air curtain to a predetermined setting or in response to a detected condition. Additionally, the automated system may adjust to inputs in real time such as due to movement by a patient (e.g., as detected using a camera, or a motion sensor).

The air curtain generating systems and methods described herein may further include a system of visualization to determine the direction of air flow from an air outlet. For example, an air delivery system may have a source that can be controllably release particulates such as a smoke such as a disco fogger smoke or talcum powder, for a period of time (e.g., less than 30 seconds, or for several minutes), such that laser beams coupled to the outlets and/or inlets of the systems described herein can be made visible. This system of visualization may be employed with all systems and subsystems described herein.

It shall be considered as disclosed that any part of a subsystem disclosed herein may be combined with any part of any other system of subsystem described herein, such that all possible combinations are considered to be disclosed.

Generally in all embodiments of a single source delivering an air curtain to create an isolation volume, the air-delivery subsystem preferably has an air pump and an air-cleaning subsystem, so as to deliver purified air. In other embodiments, there may be no air cleaning system, however air may preferably be drawn through a conduit subsystem from a region of clean air, such as outside or from a building's clean air ventilation system.

Methods

Figure 38:
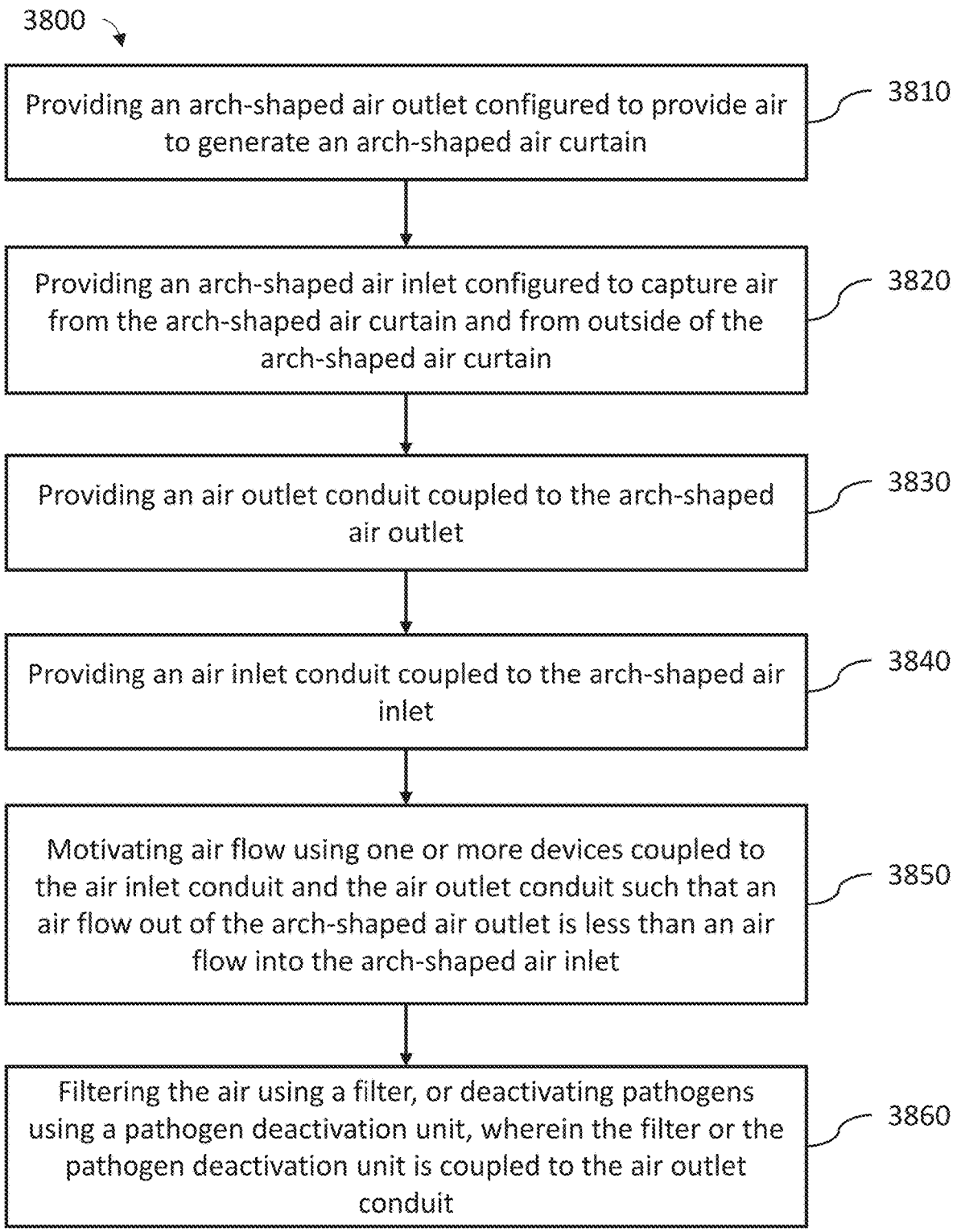
FIG. 38 shows a flowchart of a method to generate an arch-shaped air curtain includes the following steps, in accordance with some embodiments.

FIG. 38 shows a flowchart of a method 3800 to generate an arch-shaped air curtain includes the following steps, in accordance with some embodiments. The systems described herein, such as those shown in FIGS. 18-24 can be used to perform method 3800.

At block 3810, an arch-shaped air outlet is provided that is configured to provide air to generate an arch-shaped air curtain. In some cases, the arch-shaped air outlet can be configured to couple to a first region of a bed. The arch-shaped air outlet can include an air outlet port arranged along the arch-shaped air outlet. The arch-shaped air outlet can allow access to a space between the arch-shaped air curtain and the bed through an inside of the arch-shaped air outlet, as described herein (e.g., with respect to FIG. 18 or 22).

At block 3820, an arch-shaped air outlet is provided that captures air from the arch-shaped air curtain and from outside of the arch-shaped air curtain. In some cases, the arch-shaped air inlet can couple to a second region of a bed. The arch-shaped air outlet can include an air inlet port arranged along the arch-shaped air inlet. The arch-shaped air inlet can allow access to a space between the arch-shaped air curtain and the bed through an inside of the arch-shaped air inlet, as described herein (e.g., with respect to FIG. 18 or 22).

At block 3830, one or more air outlet conduits are provided that are coupled to the arch-shaped air outlet. At block 3840, one or more air inlet conduits are provided that are coupled to the arch-shaped air inlet.

At block 3850, air flow is motivated using one or more devices coupled to the air inlet conduit and the air outlet conduit such that an air flow out of the arch-shaped air outlet is less than an air flow into the arch-shaped air inlet. For example, a controller (e.g., controller 1010 of FIGS. 1A and 1B) can be used to control the one or more devices such that the air flow out of the arch-shaped air outlet is less than the air flow into the arch-shaped air inlet. In some cases, one or more sensors (e.g., flow meters) can be used to provide information about air flow rates within the system to the controller to control the one or more devices such that the air flow out of the arch-shaped air outlet is less than the air flow into the arch-shaped air inlet.

At block 3860, the air is filtered using a filter, or pathogens are deactivated using a pathogen deactivation unit, wherein the filter or the pathogen deactivation unit is coupled to the air outlet conduit. For example, the pathogen deactivation unit can include subsystems that deactivate pathogens such as UV lights, or a plasma generator. Filters can be used instead of or together with a pathogen deactivation device, for example, to reduce unwanted species (e.g., dust, pathogens, odors, or chemicals) in the air traveling through the air inlet conduit or duct. For example, the filters can be mechanical filters and/or electrostatic filters.

In other cases, a method like method 3800 can be used to generate an air curtain that is approximately flat, or planar, or otherwise not arch-shaped, for example, using the systems shown in FIG. 6, 13, or 16.

The systems used to perform method 3800 can include any of the embodiments described herein. For example, at least a portion of the first region of the bed or at least a portion of the second region of the bed can be between a head of the bed and a foot of the bed. In another example, any of the air-directing subsystems described herein (e.g., those shown in FIGS. 34A-34D) can be used with method 3800. In such examples, method 3800 could include an additional block where the air flow from the arch-shaped air outlet or the air flow into the arch-shaped air inlet is directed using an air-directing subsystem of the arch-shaped air outlet or the air flow into the arch-shaped air inlet. In another example, method 3800 can use the movable arch-shaped air outlets and/or the movable the arch-shaped air inlets, such as those shown in FIGS. 36A-36D and 37. In such examples, method 3800 could include an additional block where the movable arch-shaped air outlet and/or the movable the arch-shaped air inlet is moved in a direction shown in FIGS. 36A-36D and 37.

Embodiments

Clause 1. A system comprising: an arch-shaped air outlet configured to couple to a first region of a bed and to provide air to generate an arch-shaped air curtain, the arch-shaped air outlet comprising an air outlet port arranged along the arch-shaped air outlet, wherein the arch-shaped air outlet is configured to allow access to a space between the arch-shaped air curtain and the bed through an inside of the arch-shaped air outlet; an arch-shaped air inlet configured to couple to a second region of a bed and capture air from the arch-shaped air curtain and from outside of the arch-shaped air curtain, the arch-shaped air inlet comprising an air inlet port arranged along the arch-shaped air inlet, wherein the arch-shaped air inlet is configured to allow access to a space between the arch-shaped air curtain and the bed through the inside of the arch-shaped air inlet; one or more air outlet conduits coupled to the arch-shaped air outlet; one or more air inlet conduits coupled to the arch-shaped air inlet; one or more devices that motivate air flow, coupled to the air inlet conduit and the air outlet conduit; and a filter or pathogen deactivation unit coupled to the air outlet conduit configured to reduce pathogens in the air flowing through the air outlet conduit; wherein an air flow out of the arch-shaped air outlet is less than an air flow into the arch-shaped air inlet; wherein at least a portion of the first region of the bed or at least a portion of the second region of the bed is between a head of the bed and a foot of the bed, wherein the bed comprises four sides comprising the head, the foot, a first side extending from the head to the foot, and a second side, opposite the first side, extending from the head to the foot.

Clause 2. The system of clause 1, wherein: the arch-shaped air outlet further comprises a first material arranged across the arch-shaped air outlet; the arch-shaped air inlet further comprises a second material arranged across the arch-shaped air inlet; and wherein the first or second material is configured to be movable and to allow the access to the space between the arch-shaped air curtain and the bed through the inside of the arch-shaped air outlet or the arch-shaped air inlet, respectively.

Clause 3. The system of clause 2, wherein the first, the second, or the first and the second materials are non-rigid materials that are configured to be movable and to allow access to the space between the arch-shaped air curtain and the bed when moved.

Clause 4. The system of clause 3, wherein the first, the second, or the first and the second materials comprise one or more of: a stretchable material, a plastic sheet, a strip curtain, or an elastomeric material.

Clause 5. The system of clause 2, wherein the first or second material arranged across the arch-shaped air outlet or the arch-shaped air inlet, respectively, is configured to be movable and to allow a body of a person to extend through the arch-shaped air outlet or the arch-shaped air inlet.

Clause 6. The system of clause 2, wherein the first or second material arranged across the arch-shaped air outlet or the arch-shaped air inlet, respectively, is a rigid material.

Clause 7. The system of clause 1, wherein the air outlet port, the air inlet port, or both the air outlet and the air inlet ports, comprise one or more holes or slots, or one or more tubes.

Clause 8. The system of clause 1, wherein the air outlet port, the air inlet port, or both the air outlet and the air inlet ports, comprise a set of movable tubes configured to direct the air to generate the arch-shaped air curtain.

Clause 9. The system of clause 1, wherein the first region of the bed is at or near the head of the bed and the second region of the bed is a region between the head of the bed and the foot of the bed.

Clause 10. The system of clause 1, wherein the arch-shaped air inlet is adjustably coupled to the bed, such that a position of the arch-shaped air inlet with respect to the bed can be adjusted.

Clause 11. The system of clause 10, wherein the arch-shaped air outlet is coupled to the bed using a mounting system, wherein the mounting system is configured to move the arch-shaped air outlet such that the arch-shaped air outlet can be translated or rotated with respect to the bed.

Clause 12. The system of clause 1, wherein the first region is on the first side of the bed and the second region is on the second side of the bed.

Clause 13. The system of clause 12, wherein the arch-shaped air outlet or the arch-shaped air inlet is adjustably coupled to the bed, such that the arch-shaped air outlet or the arch-shaped air inlet can be translated or rotated with respect to the bed.

Clause 14. The system of clause 1, wherein the arch-shaped air outlet and the arch-shaped air inlet each comprises an asymmetric shape such that a first side of the arch-shaped air outlet is farther away from a top surface of the bed than a second side of the arch-shaped air outlet.

Clause 15. The system of clause 1, wherein the air inlet conduit and the air outlet conduit are coupled together into an air recycling loop, wherein the one or more devices that motivate air flow are configured to move air through the air recycling loop, and wherein some of the air in the air recycling loop is directed out of the air recycling loop such that the air flow into the arch-shaped air inlet is greater than the air flow out of the arch-shaped air outlet.

Clause 16. The system of clause 1, further comprising a controller configured to control a first device that motivates air flow of the one or more devices that motivate air flow and a second device that motivates air flow of the one or more devices that motivate air flow, wherein the air inlet conduit is coupled to the first device that motivates air flow, and the air outlet conduit is coupled to the second device that motivates air flow, and wherein the first device that motivates air flow and the second device that motivates air flow are configured to move air through the air outlet conduit and the air inlet conduit such that the air flow into the arch-shaped air inlet is greater than the air flow out of the arch-shaped air outlet.

Clause 17. The system of clause 1, wherein the bed is an adjustable bed, and wherein the arch-shaped air outlet and the arch-shaped air inlet are configured to be coupled to the bed such that the arch-shaped air outlet, the arch-shaped air inlet, or both, move with the bed when the bed is adjusted, such that the arch-shaped air curtain also moves with the bed when the bed is adjusted.

Clause 18. The system of clause 17, wherein the arch-shaped air outlet and the arch-shaped air inlet maintain relative positions to each other when moving with the bed.

Clause 19. The system of clause 1, wherein the arch-shaped air curtain comprises a plurality of flow rates in a vicinity of the arch-shaped air outlet, and wherein either the arch-shaped air outlet is further configured to generate the arch-shaped air curtain such that the plurality of flow rates are within 20% of one another along the arch-shaped air outlet, or the arch-shaped air inlet is further configured to generate the arch-shaped air curtain such that the plurality of flow rates are within 20% of one another along the arch-shaped air inlet.

Clause 20. A system comprising: an arch-shaped air outlet configured to provide air for an arch-shaped air curtain, the arch-shaped air outlet comprising: an air outlet port arranged along the arch-shaped air outlet; and a movable material arranged across the arch-shaped air outlet, wherein the movable material is configured to be movable and to allow access to a space within the arch-shaped air curtain when moved; at least one air outlet conduit coupled to the arch-shaped air outlet; and at least one device that motivates air flow coupled to the air outlet conduit; wherein the arch-shaped air outlet is configured to couple to a first region of a bed, and wherein the arch-shaped air curtain is configured to be aimed downwards towards the bed, such that the arch-shaped air curtain blocks particles from an environment from reaching a head of a patient on the bed.

Clause 21. A method for generating an arch-shaped air curtain comprising: providing an arch-shaped air outlet configured to couple to a first region of a bed and to provide air to generate an arch-shaped air curtain, the arch-shaped air outlet comprising an air outlet port arranged along the arch-shaped air outlet, wherein the arch-shaped air outlet is configured to allow access to a space between the arch-shaped air curtain and the bed through an inside of the arch-shaped air outlet; providing an arch-shaped air inlet configured to couple to a second region of a bed and capture air from the arch-shaped air curtain and from outside of the arch-shaped air curtain, the arch-shaped air inlet comprising an air inlet port arranged along the arch-shaped air inlet, wherein the arch-shaped air inlet is configured to allow access to a space between the arch-shaped air curtain and the bed through the inside of the arch-shaped air inlet; providing one or more air outlet conduits coupled to the arch-shaped air outlet; providing one or more air inlet conduits coupled to the arch-shaped air inlet; motivating air flow using one or more devices coupled to the air inlet conduit and the air outlet conduit such that an air flow out of the arch-shaped air outlet is less than an air flow in to the arch-shaped air inlet; and filtering the air using a filter, or deactivating pathogens using a pathogen deactivation unit, wherein the filter or the pathogen deactivation unit is coupled to the air outlet conduit, wherein at least a portion of the first region of the bed or at least a portion of the second region of the bed is between a head of the bed and a foot of the bed, wherein the bed comprises four sides comprising the head, the foot, a first side extending from the head to the foot, and a second side, opposite the first side, extending from the head to the foot.

Embodiments of the disclosed invention have been referenced in detail, and one or more examples of the disclosed invention have also been illustrated in the accompanying figures. Each of the embodiments and examples herein have been provided to explain the present technology, not as limitations of the present technology. Furthermore, while particular embodiments of the invention have been described in detail, it will be appreciated that alterations to, variations of, and equivalents to these embodiments may be readily conceived of by those skilled in the art, upon attaining an understanding of the foregoing. For instance, features illustrated or described with respect to one embodiment may be used with another embodiment to yield an additional embodiment. It is intended that the present subject matter covers all such modifications and variations within the scope of the appended claims and their equivalents. Those of ordinary skill in the art may practice these and other modifications and variations to the present invention without departing from the scope of the present invention, which is more particularly set forth in the appended claims. Furthermore, the foregoing description is by way of example only, and is not intended to limit the invention, as will be appreciated by those of ordinary skill in the art.

What is claimed is:

1. A system comprising:
   an arch-shaped air outlet configured to couple to a first region of a bed and to provide air to generate an arch-shaped air curtain, the arch-shaped air outlet comprising an air outlet port arranged along the arch-shaped air outlet, wherein the system further comprises a space between the arch-shaped air curtain and the bed, wherein the arch-shaped air curtain and the bed form a substantially complete enclosure, and wherein the arch-shaped air outlet is configured to allow access to the space between the arch-shaped air curtain and the bed through an inside of the arch-shaped air outlet;
   an arch-shaped air inlet configured to couple to a second region of a bed and capture air from the arch-shaped air curtain and from outside of the arch-shaped air curtain, the arch-shaped air inlet comprising an air inlet port arranged along the arch-shaped air inlet, wherein the arch-shaped air inlet is configured to allow access to the space between the arch-shaped air curtain and the bed through the inside of the arch-shaped air inlet;
   one or more air outlet conduits coupled to the arch-shaped air outlet;
   one or more air inlet conduits coupled to the arch-shaped air inlet;
   one or more devices that motivate air flow, coupled to the air inlet conduit and the air outlet conduit; and
   a filter or pathogen deactivation unit coupled to the air outlet conduit configured to reduce pathogens in the air flowing through the air outlet conduit;
   wherein an air flow out of the arch-shaped air outlet is less than an air flow into the arch-shaped air inlet;
   wherein one or more of a portion of the first region of the bed and a portion of the second region of the bed is between a head of the bed and a foot of the bed, wherein the bed comprises four sides comprising the head, the foot, a first side extending from the head to the foot, and a second side, opposite the first side, extending from the head to the foot.

2. The system of claim 1, wherein:
the arch-shaped air outlet further comprises a first material arranged across the arch-shaped air outlet;
the arch-shaped air inlet further comprises a second material arranged across the arch-shaped air inlet; and
wherein the first or second material is configured to be movable and to allow the access to the space between the arch-shaped air curtain and the bed through the inside of the arch-shaped air outlet or the arch-shaped air inlet, respectively.

3. The system of claim 2, wherein the first, the second, or the first and the second materials are non-rigid materials that are configured to be movable and to allow access to the space between the arch-shaped air curtain and the bed when moved.

4. The system of claim 3, wherein the first, the second, or the first and the second materials comprise one or more of: a stretchable material, a plastic sheet, a strip curtain, or an elastomeric material.

5. The system of claim 2, wherein the first or second material arranged across the arch-shaped air outlet or the arch-shaped air inlet, respectively, is configured to be movable and to allow a body of a person to extend through the arch-shaped air outlet or the arch-shaped air inlet.

6. The system of claim 2, wherein the first or second material arranged across the arch-shaped air outlet or the arch-shaped air inlet, respectively, is a rigid material.

7. The system of claim 1, wherein the air outlet port, the air inlet port, or both the air outlet and the air inlet ports, comprise one or more holes or slots, or one or more tubes.

8. The system of claim 1, wherein the air outlet port, the air inlet port, or both the air outlet and the air inlet ports, comprise a set of movable tubes configured to direct the air to generate the arch-shaped air curtain.

9. The system of claim 1, wherein the first region of the bed is at or near the head of the bed and the second region of the bed is a region between the head of the bed and the foot of the bed.

10. The system of claim 1, wherein the arch-shaped air inlet is adjustably coupled to the bed, such that a position of the arch-shaped air inlet with respect to the bed can be adjusted.

11. The system of claim 10, wherein the arch-shaped air outlet is coupled to the bed using a mounting system, wherein the mounting system is configured to move the arch-shaped air outlet such that the arch-shaped air outlet can be translated or rotated with respect to the bed.

12. The system of claim 1, wherein the first region is on the first side of the bed and the second region is on the second side of the bed.

13. The system of claim 12, wherein the arch-shaped air outlet or the arch-shaped air inlet is adjustably coupled to the bed, such that the arch-shaped air outlet or the arch-shaped air inlet can be translated or rotated with respect to the bed.

14. The system of claim 1, wherein the arch-shaped air outlet and the arch-shaped air inlet each comprises an asymmetric shape such that a first side of the arch-shaped air outlet is farther away from a top surface of the bed than a second side of the arch-shaped air outlet.

15. The system of claim 1, wherein the air inlet conduit and the air outlet conduit are coupled together into an air recycling loop, wherein the one or more devices that motivate air flow are configured to move air through the air recycling loop, and wherein some of the air in the air recycling loop is directed out of the air recycling loop such that the air flow into the arch-shaped air inlet is greater than the air flow out of the arch-shaped air outlet.

16. The system of claim 1, further comprising a controller configured to control a first device that motivates air flow of the one or more devices that motivate air flow and a second device that motivates air flow of the one or more devices that motivate air flow, wherein the air inlet conduit is coupled to the first device that motivates air flow, and the air outlet conduit is coupled to the second device that motivates air flow, and wherein the first device that motivates air flow and the second device that motivates air flow are configured to move air through the air outlet conduit and the air inlet conduit such that the air flow into the arch-shaped air inlet is greater than the air flow out of the arch-shaped air outlet.

17. The system of claim 1, wherein the bed is an adjustable bed, and wherein the arch-shaped air outlet and the arch-shaped air inlet are configured to be coupled to the bed such that the arch-shaped air outlet, the arch-shaped air inlet, or both, move with the bed when the bed is adjusted, such that the arch-shaped air curtain also moves with the bed when the bed is adjusted.

18. The system of claim 17, wherein the arch-shaped air outlet and the arch-shaped air inlet maintain relative positions to each other when moving with the bed.

19. The system of claim 1, wherein the arch-shaped air curtain comprises a plurality of flow rates in a vicinity of the arch-shaped air outlet, and wherein either the arch-shaped air outlet is further configured to generate the arch-shaped air curtain such that the plurality of flow rates are within 20% of one another along the arch-shaped air outlet, or the arch-shaped air inlet is further configured to generate the arch-shaped air curtain such that the plurality of flow rates are within 20% of one another along the arch-shaped air inlet.

20. A system comprising:
an arch-shaped air outlet configured to provide air for an arch-shaped air curtain, the arch-shaped air outlet comprising:
an air outlet port arranged along the arch-shaped air outlet; and
a movable material arranged across the arch-shaped air outlet, wherein the movable material is configured to be movable and to allow access to a space within the arch-shaped air curtain when moved;
at least one air outlet conduit coupled to the arch-shaped air outlet; and
at least one device that motivates air flow coupled to the air outlet conduit;
wherein the arch-shaped air outlet is configured to couple to a first region of a bed, and
wherein the arch-shaped air curtain is configured to be aimed downwards towards the bed, such that the arch-shaped air curtain forms a closed environment and blocks particles from an environment outside of the closed environment from reaching a head of a patient on the bed.

21. A method for generating an arch-shaped air curtain comprising:
providing an arch-shaped air outlet configured to couple to a first region of a bed and to provide air to generate an arch-shaped air curtain, the arch-shaped air outlet comprising an air outlet port arranged along the arch-shaped air outlet, wherein the arch-shaped air outlet is configured to allow access to a space between the arch-shaped air curtain and the bed through an inside of the arch-shaped air outlet;
providing an arch-shaped air inlet configured to couple to a second region of a bed and capture air from the arch-shaped air curtain and from outside of the arch-shaped air curtain, the arch-shaped air inlet comprising an air inlet port arranged along the arch-shaped air inlet, wherein the arch-shaped air inlet is configured to allow access to a space between the arch-shaped air curtain and the bed through the inside of the arch-shaped air inlet;

providing one or more air outlet conduits coupled to the arch-shaped air outlet;

providing one or more air inlet conduits coupled to the arch-shaped air inlet;

motivating air flow using one or more devices coupled to the air inlet conduit and the air outlet conduit such that an air flow out of the arch-shaped air outlet is less than an air flow into the arch-shaped air inlet; and filtering the air using a filter, or deactivating pathogens using a pathogen deactivation unit, wherein the filter or the pathogen deactivation unit is coupled to the air outlet conduit, wherein one or more of a portion of the first region of the bed and a portion of the second region of the bed is between a head of the bed and a foot of the bed, wherein the bed comprises four sides comprising the head, the foot, a first side extending from the head to the foot, and a second side, opposite the first side, extending from the head to the foot.

22. The system of claim 1, wherein the arch-shaped air outlet and the arch-shaped air inlet are inflatable.

23. A system comprising:

an arch-shaped air outlet configured to couple to a first region of a bed and to provide air to generate an arch-shaped air curtain, the arch-shaped air outlet comprising an air outlet port arranged along the arch-shaped air outlet, wherein the system further comprises a space between the arch-shaped air curtain and the bed, wherein the arch-shaped air curtain and the bed form a substantially complete enclosure, and wherein the arch-shaped air outlet is configured to allow access to the space between the arch-shaped air curtain and the bed through an inside of the arch-shaped air outlet;

an arch-shaped air inlet configured to couple to a second region of a bed and capture air from the arch-shaped air curtain and from outside of the arch-shaped air curtain, the arch-shaped air inlet comprising an air inlet port arranged along the arch-shaped air inlet, wherein the arch-shaped air inlet is configured to allow access to the space between the arch-shaped air curtain and the bed through the inside of the arch-shaped air inlet;

one or more air outlet conduits coupled to the arch-shaped air outlet;

one or more air inlet conduits coupled to the arch-shaped air inlet; and one or more devices that motivate air flow, coupled to the air inlet conduit and the air outlet conduit;

wherein the arch-shaped air outlet and the arch-shaped air inlet are inflatable.

24. The system of claim 23, further comprising an air source subsystem coupled to a vent of the arch-shaped air inlet.

25. The system of claim 24, wherein the arch-shaped air inlet comprises a separately inflatable section coupled to the vent, wherein the separately inflatable section forms a structure that provides mechanical stability to the arch-shaped air inlet when the separately inflatable section is inflated.

26. The system of claim 24, wherein the arch-shaped air inlet comprises a separately inflatable section coupled to the vent, wherein a pressure inside the separately inflatable section is sufficiently high to overcome a force of suction on the arch-shaped air inlet when the separately inflatable section is inflated.

* * * * *